(12) United States Patent
Davidson et al.

(10) Patent No.: US 11,406,781 B2
(45) Date of Patent: Aug. 9, 2022

(54) PATIENT INTERFACE

(71) Applicant: RESMED PTY LTD, Bella Vista (AU)

(72) Inventors: Aaron Samuel Davidson, Sydney (AU); Kam Man Law, Sydney (AU); Lemmy Nga, Sydney (AU); Rupert Christian Scheiner, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/269,928

(22) PCT Filed: Aug. 20, 2019

(86) PCT No.: PCT/AU2019/050873
§ 371 (c)(1),
(2) Date: Feb. 19, 2021

(87) PCT Pub. No.: WO2020/037359
PCT Pub. Date: Feb. 27, 2020

(65) Prior Publication Data
US 2021/0252241 A1 Aug. 19, 2021

Related U.S. Application Data

(60) Provisional application No. 62/764,992, filed on Aug. 20, 2018.

(51) Int. Cl.
*A61M 16/06* (2006.01)
*A61M 16/00* (2006.01)
*A61M 16/16* (2006.01)

(52) U.S. Cl.
CPC .... *A61M 16/0616* (2014.02); *A61M 16/0666* (2013.01); *A61M 16/0683* (2013.01);
(Continued)

(58) Field of Classification Search
CPC .............. A61M 16/06; A61M 16/0605; A61M 16/0611; A61M 16/0616; A61M 16/0622;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

WO WO 98/004310 A1 2/1998
WO WO 98/034665 A1 8/1998
(Continued)

OTHER PUBLICATIONS

"*Respiratory Physiology*", by John B. West, Lippincott Williams & Wilkins, 9$^{th}$ edition published 2012 (8 pages).
(Continued)

*Primary Examiner* — Joseph D. Boecker
(74) *Attorney, Agent, or Firm* — Nixon & Vanderhye P.C.

(57) ABSTRACT

A patient interface may include a plenum chamber pressurisable to a therapeutic pressure, a seal-forming structure constructed and arranged to form a seal with a region of the patient's face surrounding an entrance to the patient's airways, a positioning and stabilising structure to provide a force to hold the seal-forming structure in a therapeutically effective position on the patient's head, and a vent structure to allow a continuous flow of gases exhaled by the patient from an interior of the plenum chamber to ambient, wherein the patient interface is configured to leave the patient's mouth uncovered during therapy, wherein the seal-forming structure comprises two lateral support regions, each located at a lateralmost side of the seal-forming structure, and a medial region positioned between the lateral support regions, the hole passing through the medial region, and
(Continued)

wherein the lateral support regions are thicker than the medial region.

30 Claims, 66 Drawing Sheets

(52) U.S. Cl.
CPC ......... *A61M 16/0066* (2013.01); *A61M 16/16* (2013.01); *A61M 2016/003* (2013.01); *A61M 2016/0027* (2013.01)

(58) Field of Classification Search
CPC .......... A61M 16/0666; A61M 16/0672; A61M 16/0683; A62B 18/025
See application file for complete search history.

(56) References Cited

U.S. PATENT DOCUMENTS

| | | | |
|---|---|---|---|
| 6,532,959 | B1 | 3/2003 | Berthon-Jones |
| 6,581,594 | B1 | 6/2003 | Drew et al. |
| 7,178,525 | B2 | 2/2007 | Matula, Jr. et al. |
| 7,866,944 | B2 | 1/2011 | Kenyon et al. |
| 7,975,694 | B2 | 7/2011 | Ho |
| 8,025,057 | B2 | 9/2011 | Ging et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 9,517,319 | B2 | 12/2016 | Omura et al. |
| 2009/0044808 | A1 | 2/2009 | Guney et al. |
| 2009/0050156 | A1 | 2/2009 | Ng et al. |
| 2009/0065005 | A1 | 3/2009 | Ades |
| 2010/0000534 | A1 | 1/2010 | Kooij et al. |
| 2011/0000492 | A1* | 1/2011 | Veliss ............... A61M 16/0683 128/207.13 |
| 2012/0266890 | A1 | 10/2012 | Baecke et al. |
| 2013/0213400 | A1* | 8/2013 | Barlow ................ A61M 16/06 128/205.25 |
| 2015/0328423 | A1* | 11/2015 | Siew ................. A61M 16/0683 128/205.25 |
| 2016/0095996 | A1* | 4/2016 | Gusky ................ A61M 16/125 128/205.25 |
| 2016/0151597 | A1 | 6/2016 | Baecke et al. |
| 2016/0296720 | A1* | 10/2016 | Henry ............... A61M 16/0622 |
| 2017/0312466 | A1 | 11/2017 | Manning |
| 2017/0326320 | A1* | 11/2017 | Baigent ............. A61M 16/0616 |
| 2017/0326321 | A1 | 11/2017 | Grashow et al. |
| 2018/0099113 | A1 | 4/2018 | Bell et al. |
| 2018/0177965 | A1* | 6/2018 | Patel ................. A61M 16/0683 |
| 2019/0022343 | A1 | 1/2019 | Kooij et al. |
| 2019/0091428 | A1 | 3/2019 | Chodkowski et al. |
| 2019/0125996 | A1 | 5/2019 | Bentley et al. |
| 2021/0038848 | A1* | 2/2021 | Eves ................. A61M 16/0616 |

FOREIGN PATENT DOCUMENTS

| | | | | |
|---|---|---|---|---|
| WO | WO 2000/078381 | A1 | 12/2000 | |
| WO | WO 2004/073778 | A1 | 9/2004 | |
| WO | WO 2005/063328 | A1 | 7/2005 | |
| WO | WO 2006/074513 | A1 | 7/2006 | |
| WO | WO 2006/130903 | A1 | 12/2006 | |
| WO | 2008/011682 | | 1/2008 | |
| WO | WO 2009/052560 | A1 | 4/2009 | |
| WO | 2010/131189 | | 11/2010 | |
| WO | 2010/139014 | | 12/2010 | |
| WO | WO 2010/135785 | A1 | 12/2010 | |
| WO | 2011/059346 | | 5/2011 | |
| WO | 2012/154064 | | 11/2012 | |
| WO | WO 2012/171072 | A1 | 12/2012 | |
| WO | WO 2013/020167 | A1 | 2/2013 | |
| WO | 2014/077708 | | 5/2014 | |
| WO | 2014/110626 | | 7/2014 | |
| WO | 2016/108116 | A1 | 7/2016 | |
| WO | 2017/037638 | | 3/2017 | |
| WO | 2017/044392 | | 3/2017 | |
| WO | WO-2017049361 | A * | 3/2017 | ........ A61M 16/0633 |
| WO | 2017/124152 | | 7/2017 | |
| WO | 2017/185140 | | 11/2017 | |
| WO | 2018/176094 | | 10/2018 | |

OTHER PUBLICATIONS

International Search Report dated Nov. 14, 2019 issued in International Application No. PCT/AU2019/050873 (24 pages).
Written Opinion of the International Searching Authority dated Nov. 14, 2019 issued in International Application No. PCT/AU2019/050873 (8 pages).
Written Opinion of the International Searching Authority dated Jul. 15, 2020 issued in International Application No. PCT/AU2019/050873 (7 pages).
International Preliminary Report on Patentability dated Dec. 4, 2020 issued in International Application No. PCT/AU2019/050873 (26 pages).
Extended European Search Report dated Nov. 3, 2021 issued in European Application No. 19852699.8 (11 pages).
Examination Report dated Nov. 23, 2021 issued in New Zealand Application No. 772916 (4 pages).

* cited by examiner

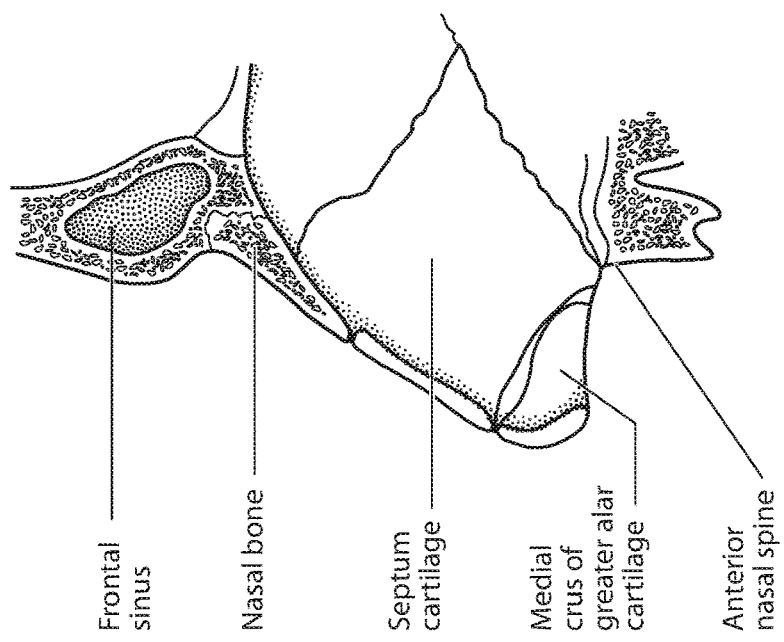
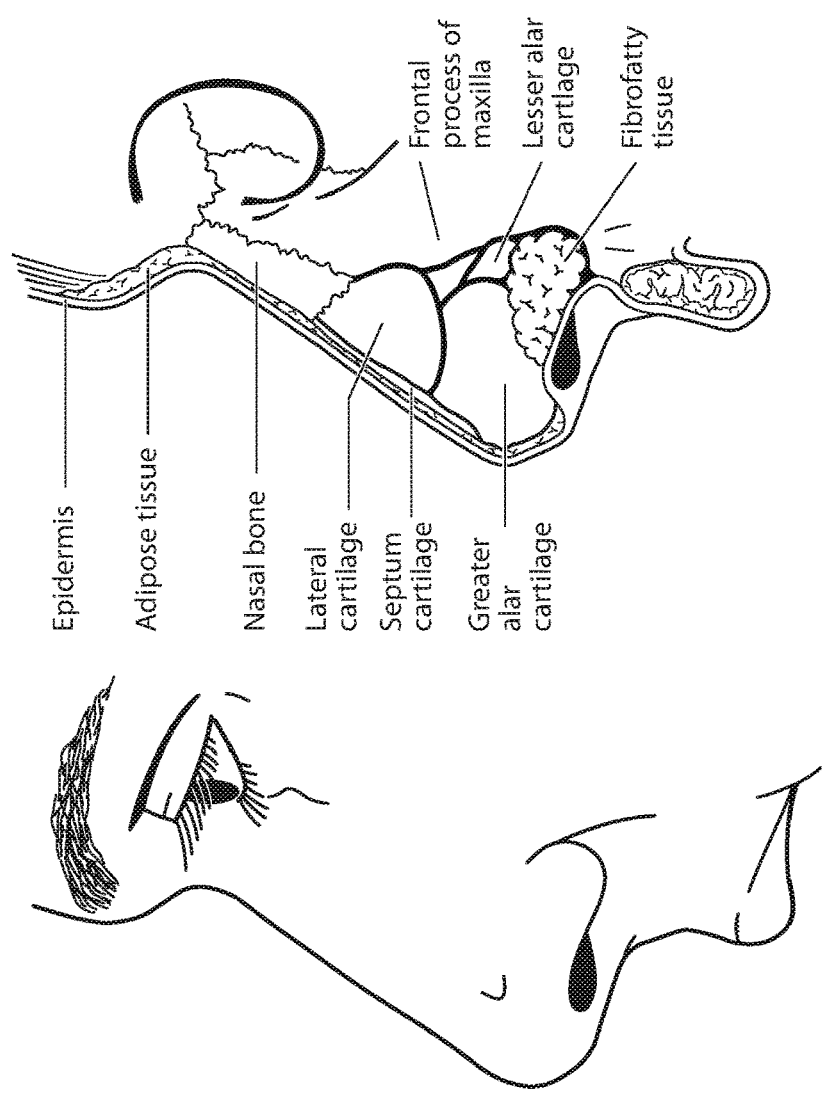
FIG. 2G  FIG. 2H  FIG. 2I

Relatively Large Positive Curvature

Relatively Small Positive Curvature

Zero Curvature

Relatively Small Negative Curvature

Relatively Large Negative Curvature

Left-hand rule

Right-hand rule

Left ear helix

Right-hand helix
Right-hand positive

Right ear helix

PATIENT INTERFACE

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 CROSS-REFERENCE TO RELATED APPLICATIONS

This application is the U.S. national phase of International Application No. PCT/AU2019/050873 filed Aug. 20, 2019 which designated the U.S. and claims priority to U.S. Provisional Application No. 62/764,992, filed Aug. 20, 2018, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients, CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/ or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NW) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004310; WO 2006/074513; WO 2010/135785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063328 and WO 2006/130903 (describing amongst other things aspects of the ResMed Limited MIRAGE LIBERTY™ full-face mask); International Patent Application WO 2009/052560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide ventilation support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034665; International Patent Application Publication No. WO 2000/078381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

Another aspect of the present technology is directed to a patient interface that may comprise: a plenum chamber; a seal-forming structure; and a positioning and stabilising structure. The patient interface may further comprise a vent structure. The patient may further be configured to leave the patient's mouth uncovered, or if the seal-forming structure is configured to seal around the patient's nose and mouth, the patient interface may be further configured to allow the patient to breath from ambient in the absence of a flow of pressurised air through the plenum chamber inlet port.

An aspect of the present technology is directed to a patient interface may include a plenum chamber pressurisable to a therapeutic pressure, a seal-forming structure constructed and arranged to form a seal with a region of the patient's face surrounding an entrance to the patient's airways, a positioning and stabilising structure to provide a force to hold the seal-forming structure in a therapeutically effective position on the patient's head, and a vent structure to allow a continuous flow of gases exhaled by the patient from an interior of the plenum chamber to ambient, wherein the patient interface is configured to leave the patient's mouth uncovered during therapy, wherein the seal-forming structure comprises two lateral support regions, each located at a lateralmost side of the seal-forming structure, and a medial region positioned between the lateral support regions, the hole passing through the medial region, and wherein the lateral support regions are thicker than the medial region.

In examples of any of the aspects of any of the preceding paragraphs, (a) the seal-forming structure may comprise two mid-lateral regions that are each laterally outward from and adjacent to the medial region and medially inward from and adjacent to the lateral support regions, the mid-lateral regions being thicker than the medial region and thinner than the lateral support regions, (b) the seal-forming structure may comprise two corner regions configured to engage the patient's face at the subalare region, the corner regions being located where the medial region, the mid-lateral regions, and the lateral support regions converge, (c) the hole may be divided into two naris openings by a bridge portion, the bridge portion being slack in an undeformed state, (d) the bridge portion may be thicker than the medial region, (e) the naris openings may be surrounded by the medial region and the bridge portion, (f) the seal-forming structure may be constructed of a flexible material, (g) the flexible material may be silicone, (h) the plenum chamber may comprise an inside surface and an outside surface, and the inside surface may be arranged to be at said therapeutic pressure in use, and shell outside surface is arranged to be at ambient pressure in use, (h) the plenum chamber may be structured to be rigid when subject to an internal pressure of less than about 30 cmH2O above ambient pressure, (i) the plenum chamber may be constructed from a hard plastic material, (j) the plenum chamber may be constructed from a transparent material, (k) the vent structure may comprise a plurality of vent holes formed in the plenum chamber, (l) the medial region may extend to an anterior side of the seal-forming structure that does not contact the patient during use, (m) the medial region may extend to the anterior side of the seal-forming structure on a superior portion of the seal-forming structure, (n) the medial region may extend to the anterior side of the seal-forming structure on an inferior portion of the seal-forming structure, (o) the mid-lateral regions may extend to an anterior side of the seal-forming structure that does not contact the patient during use, (p) the mid-lateral regions may extend to the anterior side of the seal-forming structure on a superior portion of the seal-forming structure, (q) the mid-lateral regions may extend to the anterior side of the seal-forming structure on an inferior portion of the seal-forming structure, (r) the bridge portion may be curved towards the plenum chamber to avoid contact with the patient's columella during use, (s) the medial region may be positioned between the mid-lateral regions such that the mid-lateral regions are separate from one another, (t) the medial region and the mid-lateral regions may be positioned between the lateral support regions such that the lateral support regions are separate from one another, and/or (u) the seal-forming structure may be shaped and dimensioned not to engage the patient's nose superior to the pronasale.

Another aspect of the present technology is directed to a patient interface comprising: a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient; a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure to allow a continuous flow of gases exhaled by the patient from an interior of the plenum chamber to ambient, said vent structure being sized and shaped to maintain the therapeutic pressure in the plenum chamber in use; wherein the patient interface is configured to leave the patient's mouth uncovered during therapy, wherein the plenum chamber further comprises a pair of plenum chamber connectors, each of the plenum chamber connectors positioned on a respective lateral side of the plenum chamber, wherein the positioning and stabilising structure further comprises a tube having a pair of ends, wherein the positioning and stabilising structure further comprises a clip joined to a clip overmold at each of the ends, the clip overmold being joined to the tube at a corresponding one of the ends, and wherein each of the ends is removably connected to a corresponding plenum chamber connector by engagement of the clip with the corresponding plenum chamber connector.

In examples of any of the aspects of any of the preceding paragraphs, (a) the tube may be constructed from a first silicone material, each of the clip overmolds may be constructed from a second silicone material that is different from the first silicone material, and each of the clips may be constructed from a first plastic material that is relatively more rigid than the first silicone material and the second silicone material, (b) the first silicone material may be unable to bond with the first plastic material, (c) the first silicone material may be unable to chemically bond with the first plastic material, (d) the second silicone material may be chemically bondable to the first silicone material and to the first plastic material, (e) the tube may be constructed from a single, homogenous piece of the first silicone material, (f) each of the clip overmolds may be constructed from a single, homogeneous piece of the second silicone material, (g) each of the clips may be constructed from a single, homogeneous piece of the first plastic material, (h) the plenum chamber may be constructed from a second plastic material, (i) the second plastic material and the first plastic material may be the same, (j) the second plastic material and the first plastic material may be different, (k) each of the plenum chamber connectors may comprise a pair of slots such that the plenum chamber connectors are deformable to a reduced cross-section, (l) each of the plenum chamber connectors may be configured to be connected to a corresponding one of the clips with a snap-fit, (m) each of the clips and each of the clip overmolds may be positioned completely internally of a corresponding end of the tube, (n) when the ends of the tube are connected to corresponding ones of the plenum chamber connectors, the plenum chamber connectors may be positioned completely internally of a corresponding end of the tube, and/or (o) each of the plenum chamber connectors may comprise a chamfered edge and each of the clips may comprise a notch, and the chamfered edge and the corresponding notch being configured to engage with a snap-fit.

Another aspect of one form of the present technology is a patient interface that is moulded or otherwise constructed with a perimeter shape which is complementary to that of an intended wearer.

An aspect of one form of the present technology is a method of manufacturing.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
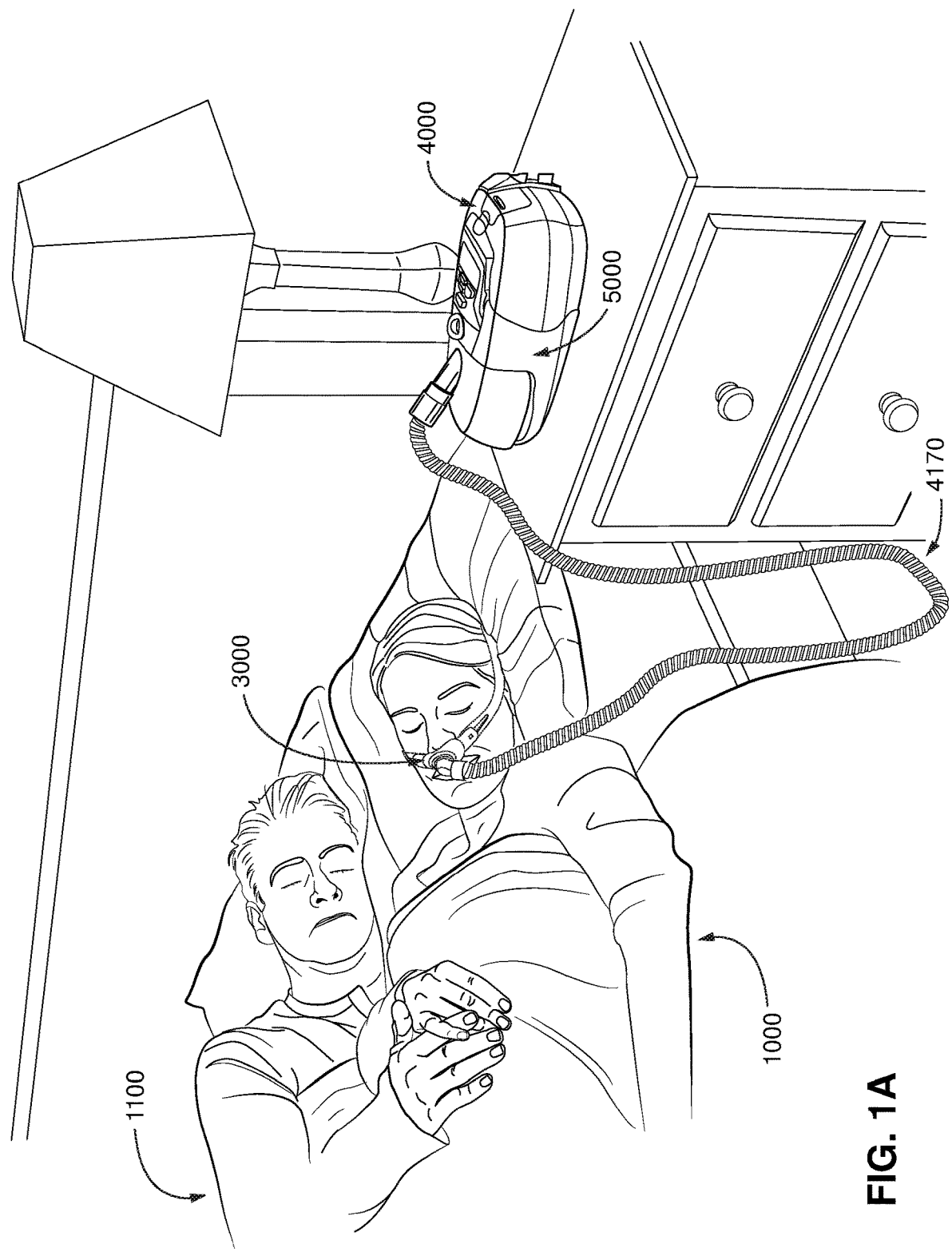
Figure 1B:
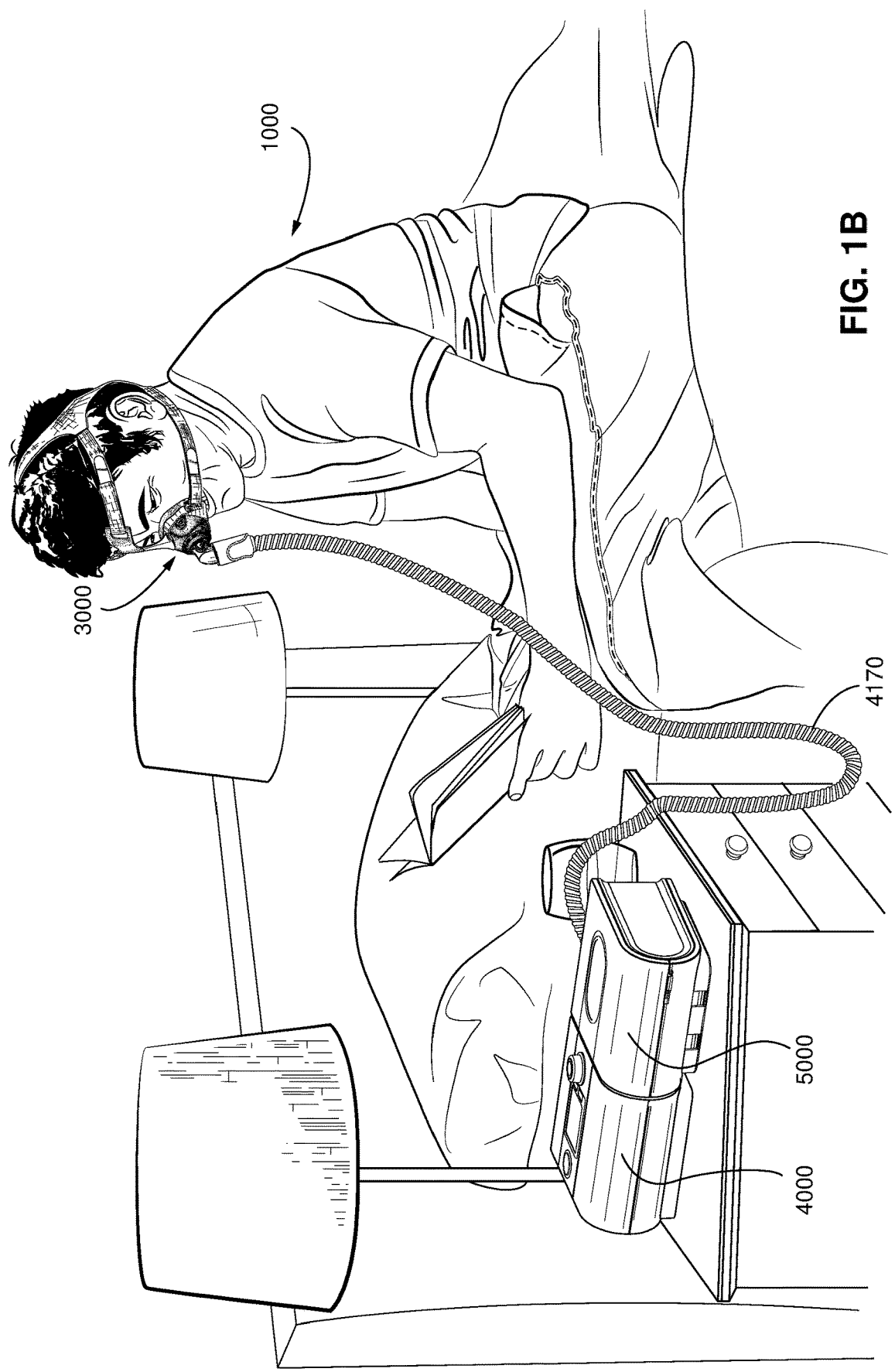
Figure 1C:
Figure 2A:
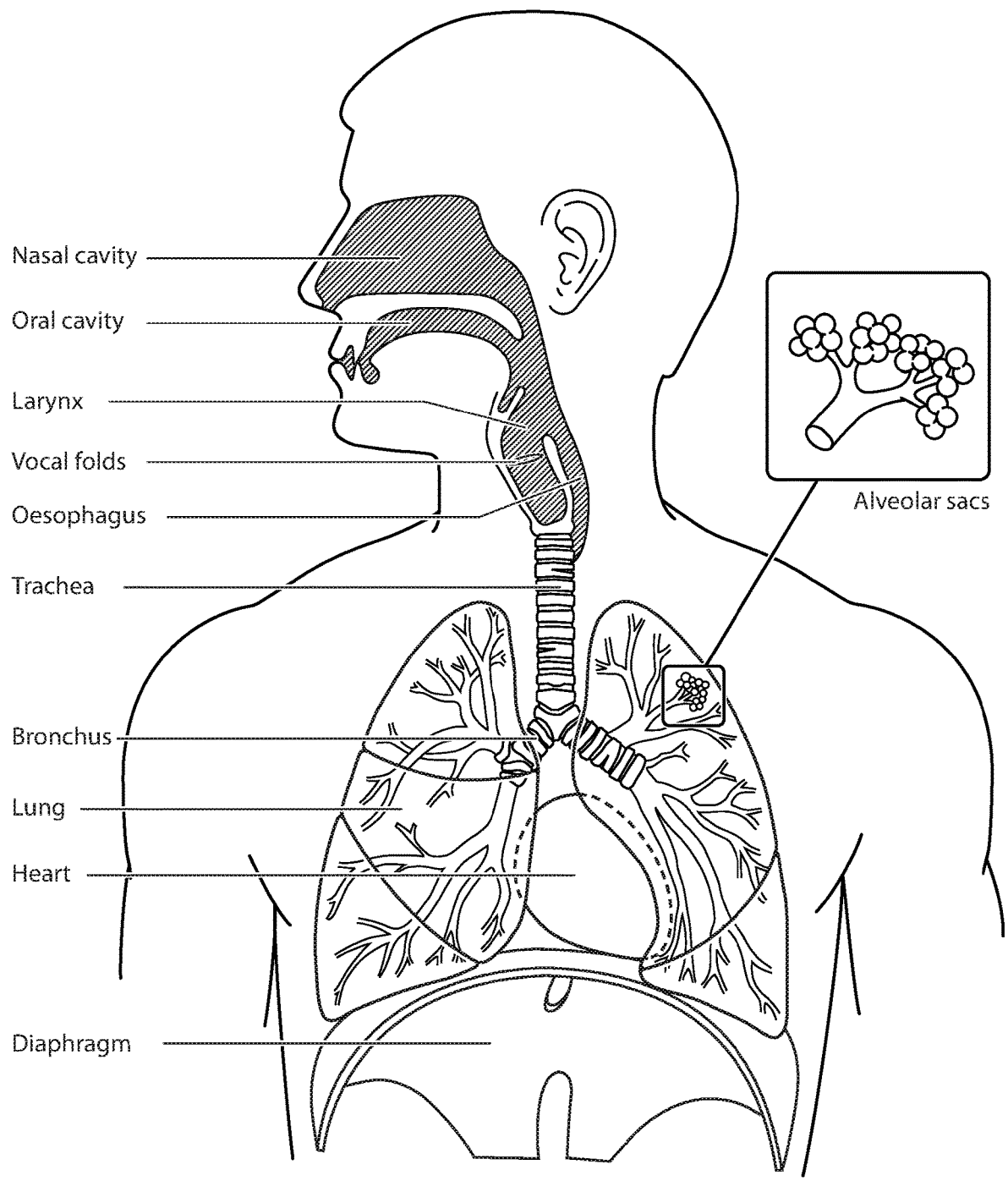
FIG. 2A shows an overview of a human respiratory system including the nasal and oral cavities, the larynx, vocal folds, oesophagus, trachea, bronchus, lung, alveolar sacs, heart and diaphragm.
Figure 2B:
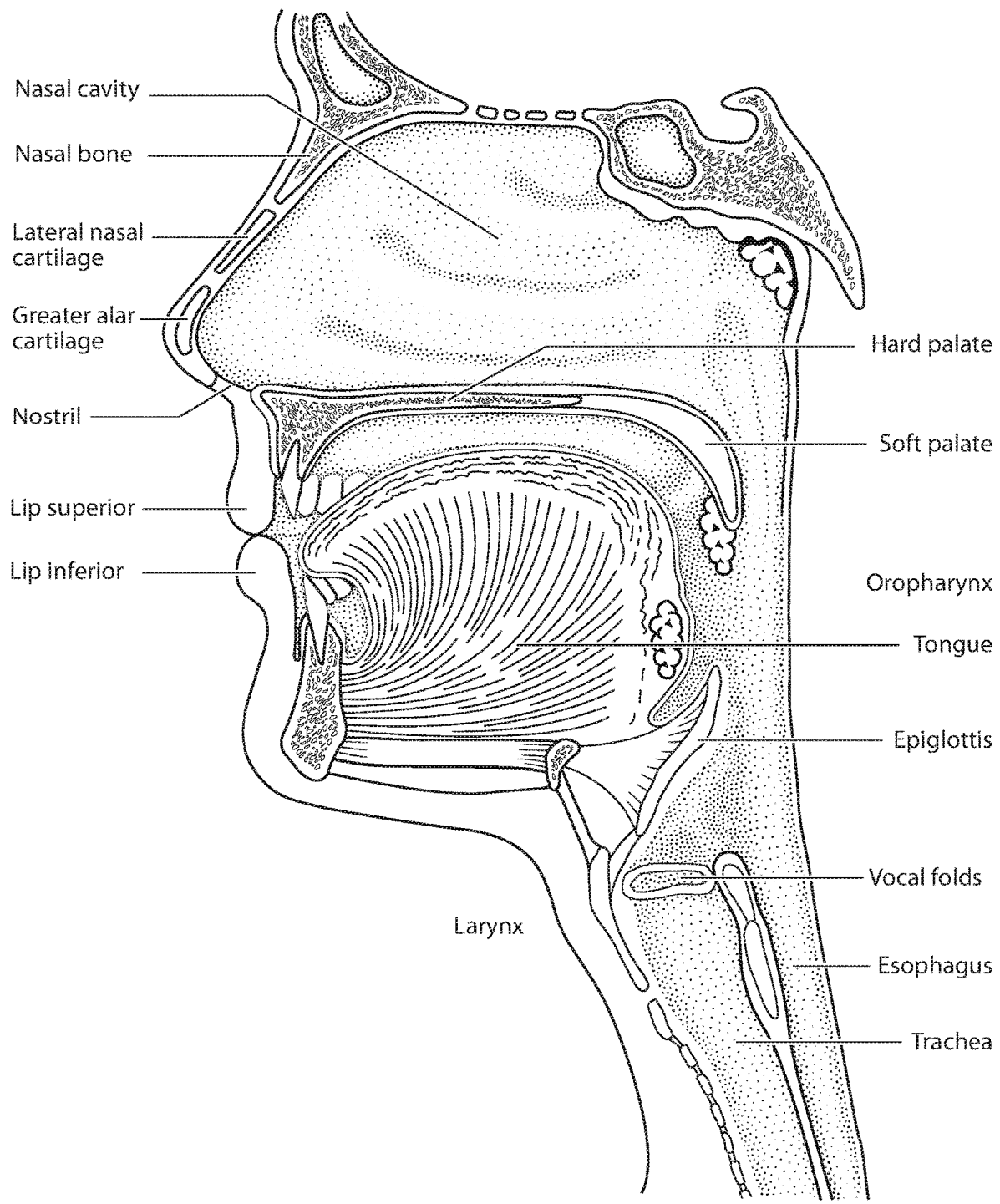
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
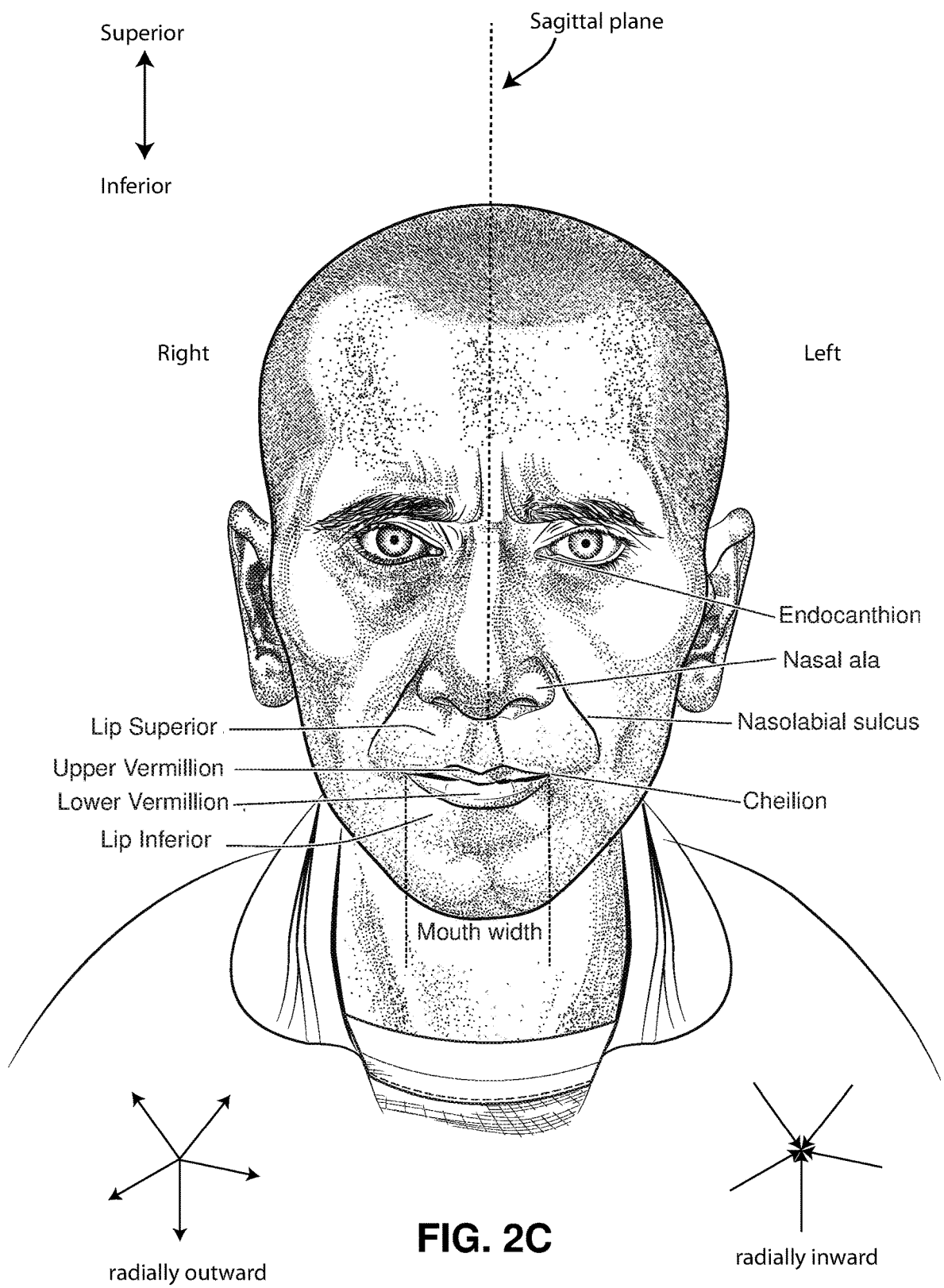
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
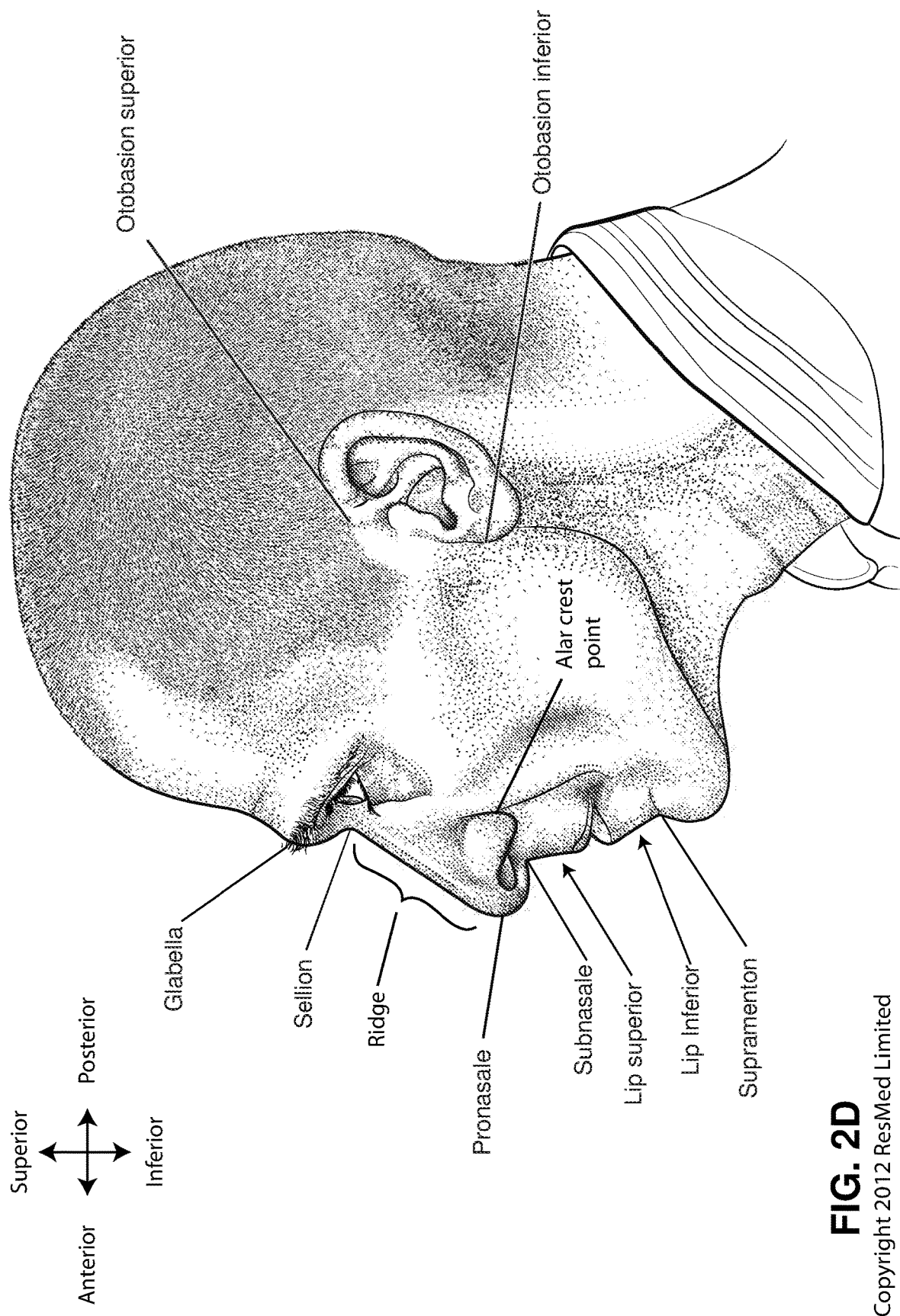
FIG. 2D is a side view of a head with several features of surface anatomy identified including *glabella*, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
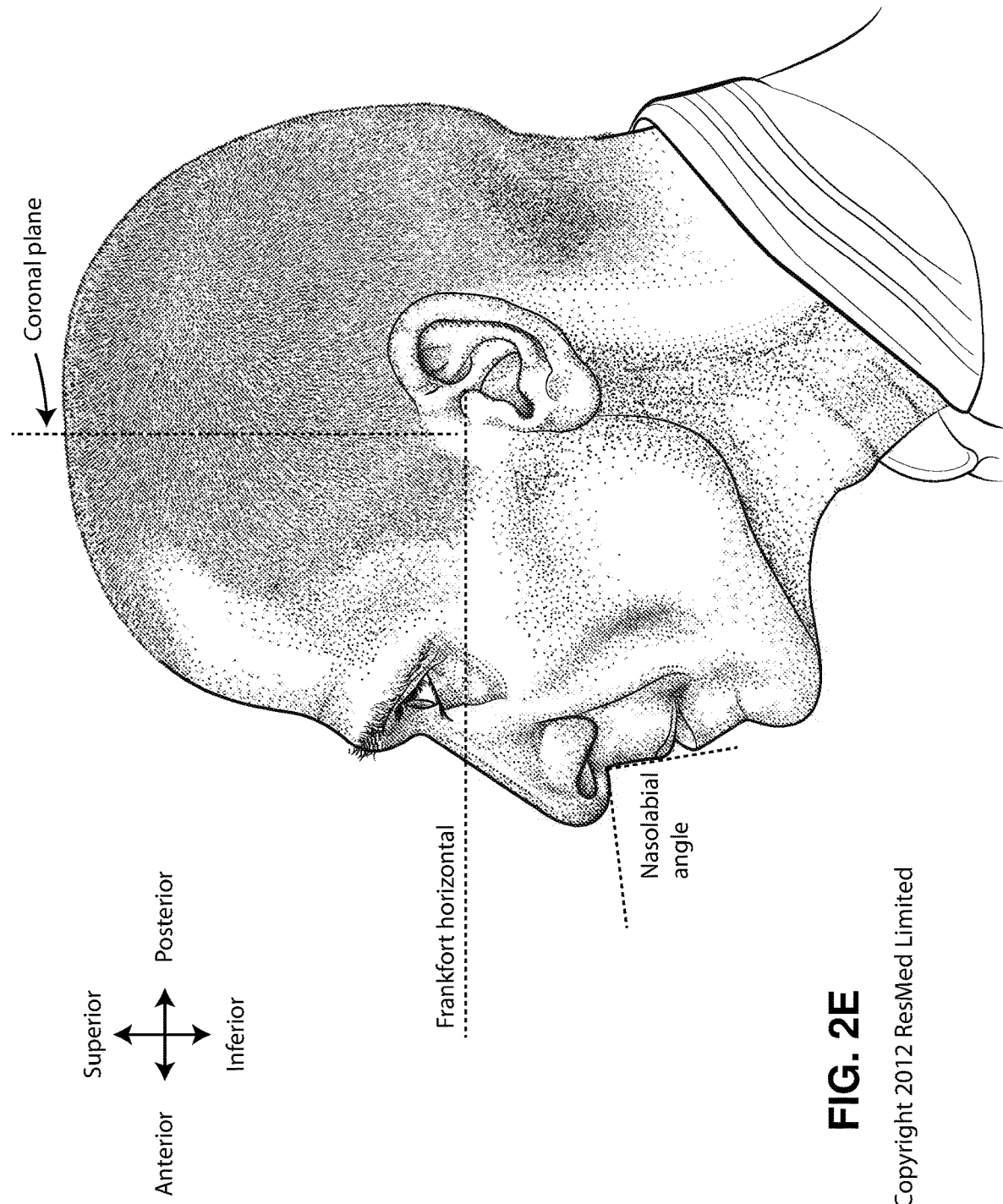

FIG. 2E is a further side view of a head. The approximate locations of the Frankfort horizontal and nasolabial angle are indicated. The coronal plane is also indicated.

Figure 2F:
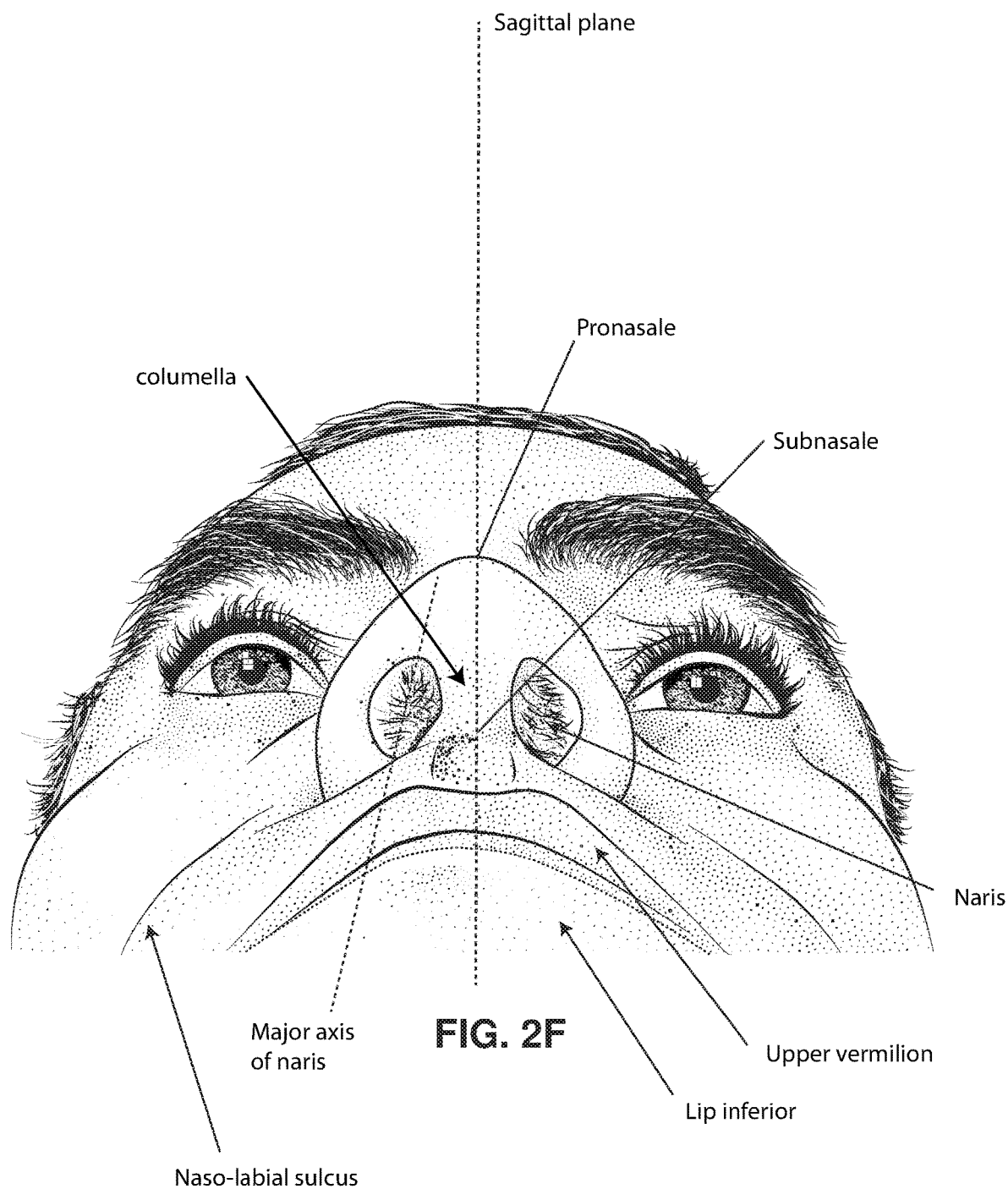

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
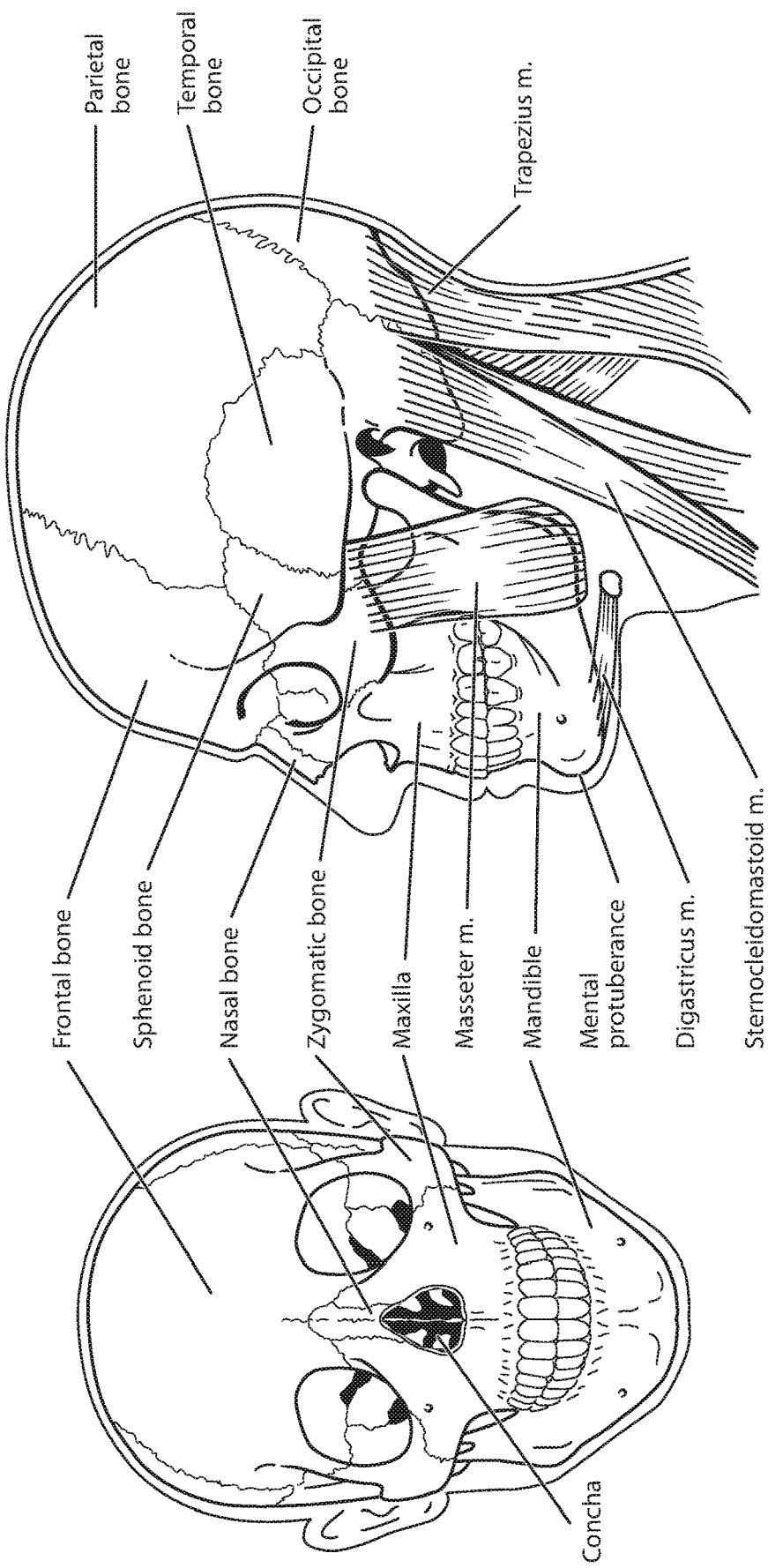

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
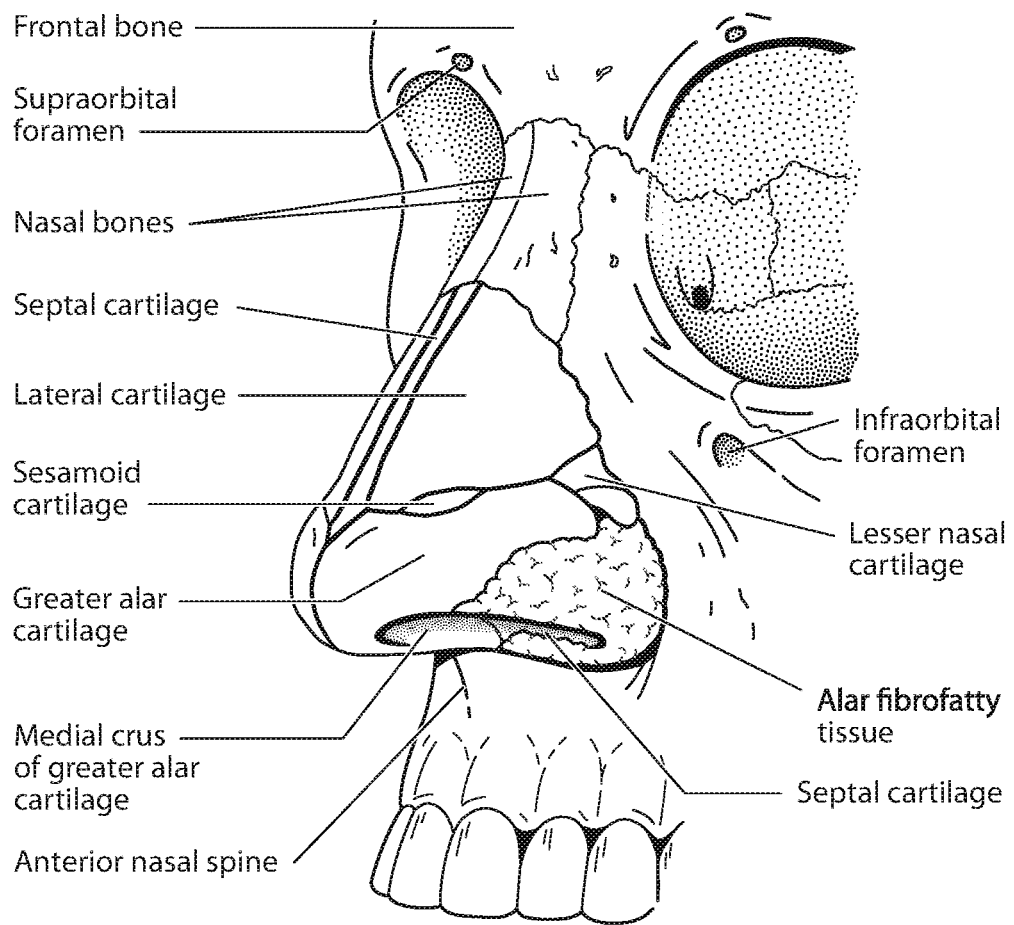

FIG. 2L shows an anterolateral view of a nose.

4.3 Patient Interface

Figure 3A:
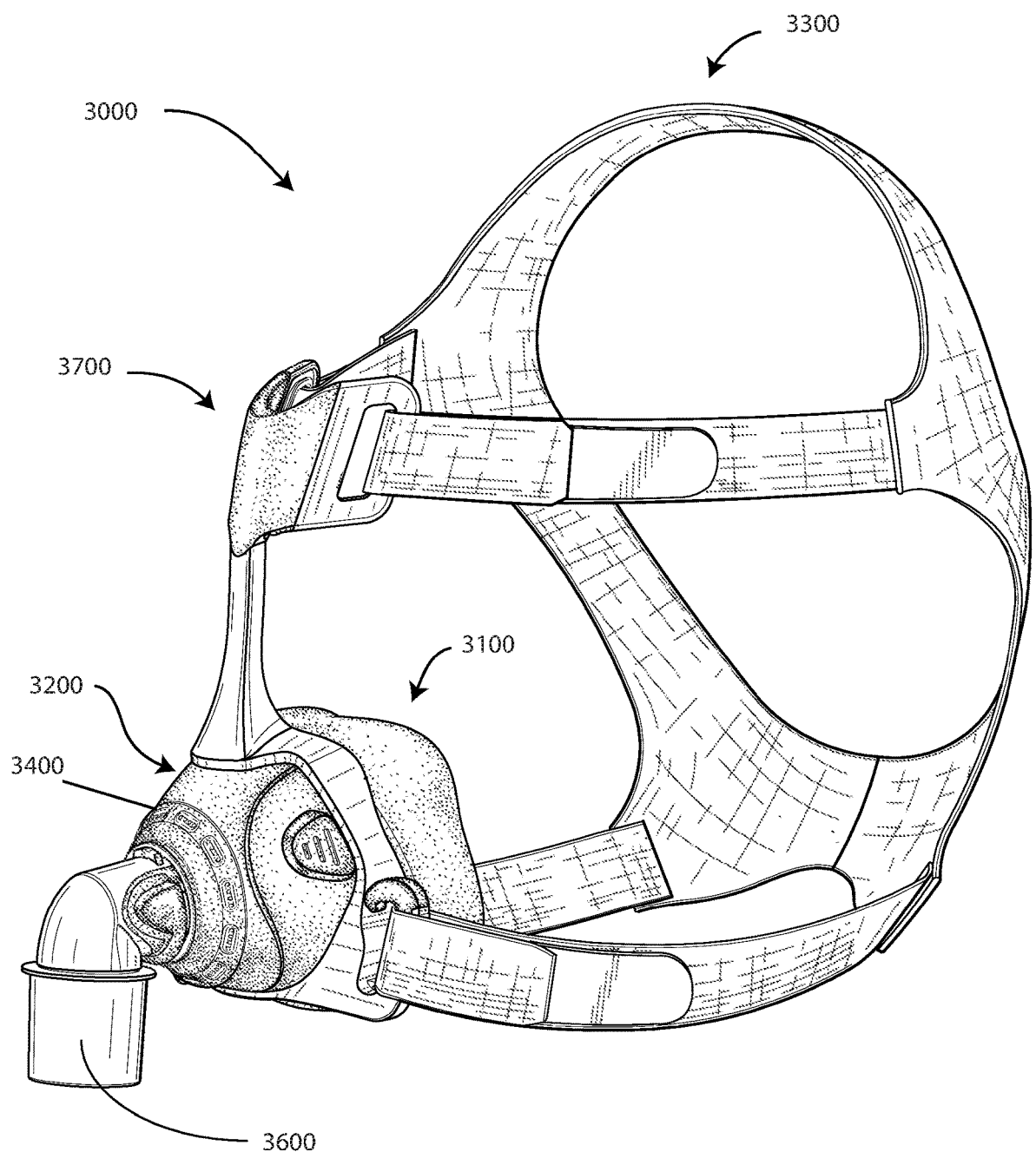

FIG. 3A shows a patient interface in the form of a nasal mask in accordance with one form of the present technology.

Figure 3B:
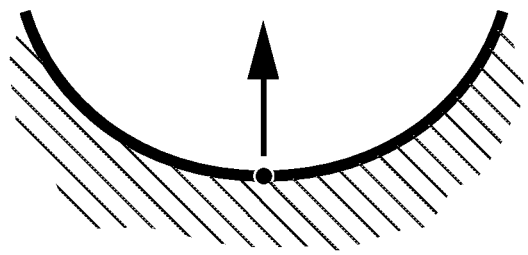

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
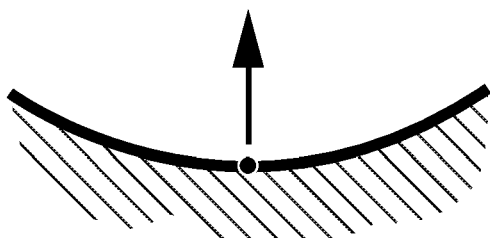

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
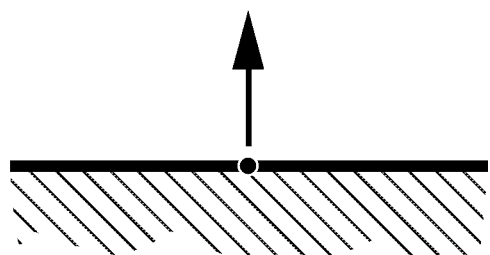

FIG. 3D shows a schematic of a cross-section through a structure at a point. An outward normal at the point is indicated. The curvature at the point has a value of zero.

Figure 3E:
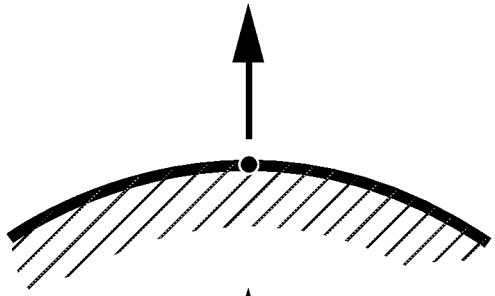

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
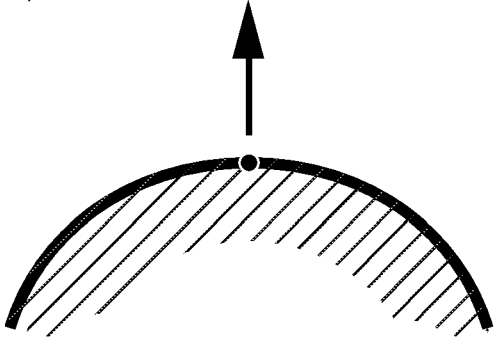

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
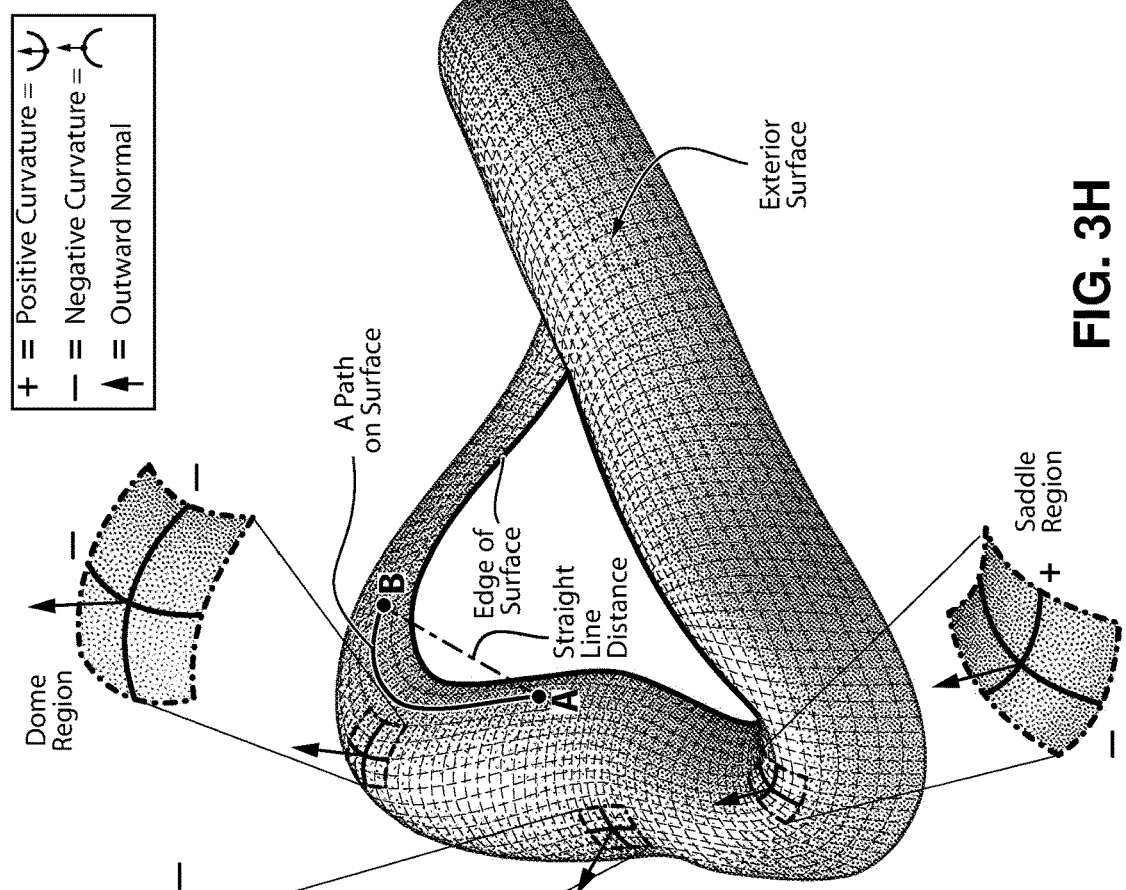
Figure 3G:
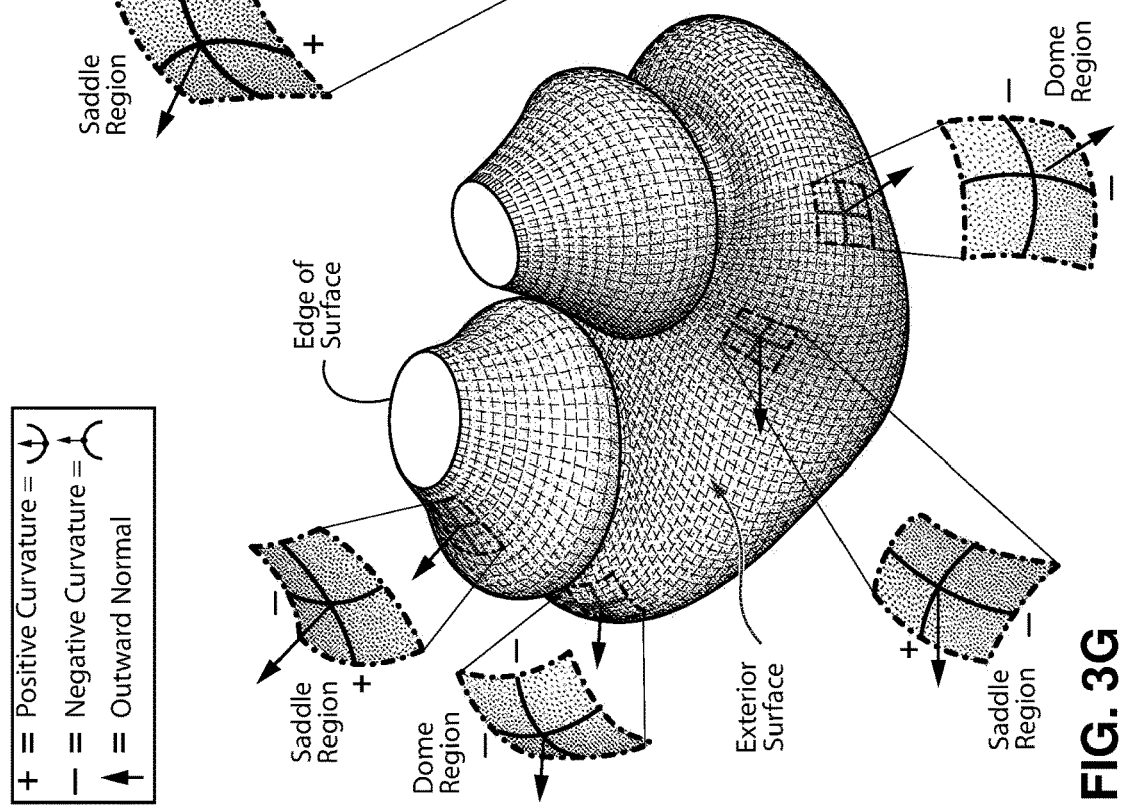

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
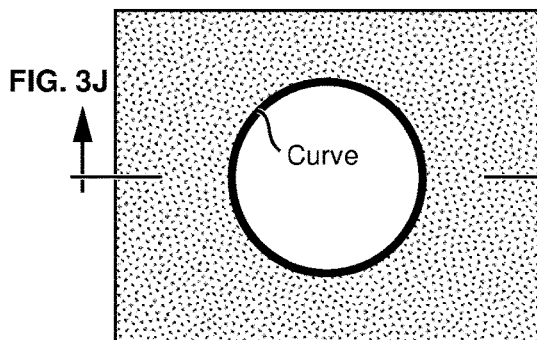

FIG. 3I shows the surface of a structure, with a one dimensional hole in the surface. The illustrated plane curve forms the boundary of a one dimensional hole.

Figure 3K:
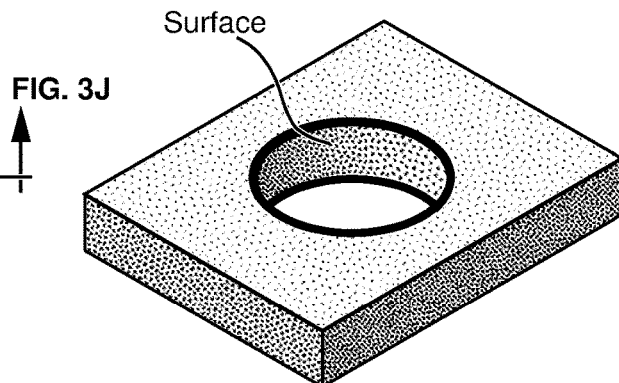
Figure 3J:
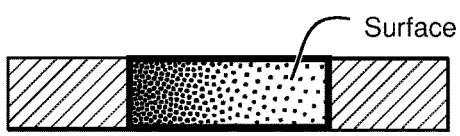

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
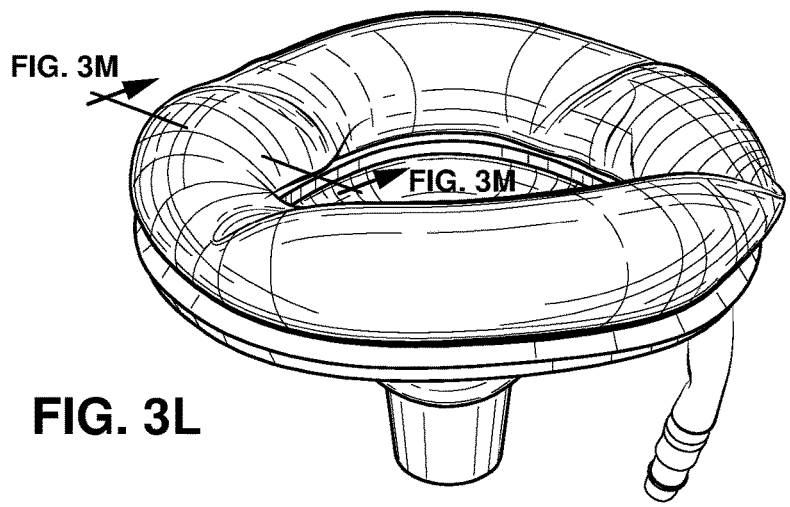

FIG. 3L shows a mask having an inflatable bladder as a cushion.

Figures 3M, 3N:
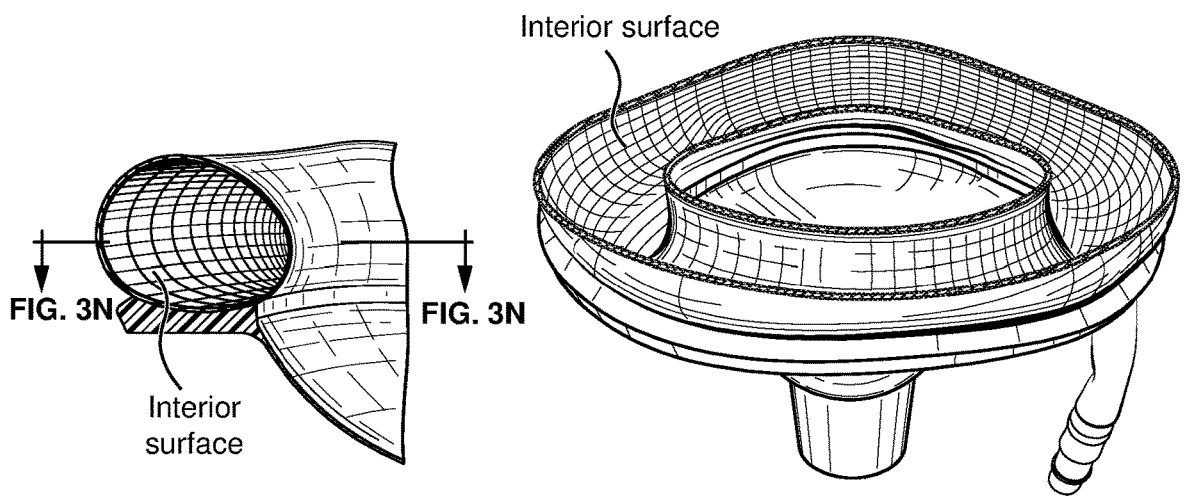

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

Figure 3O:
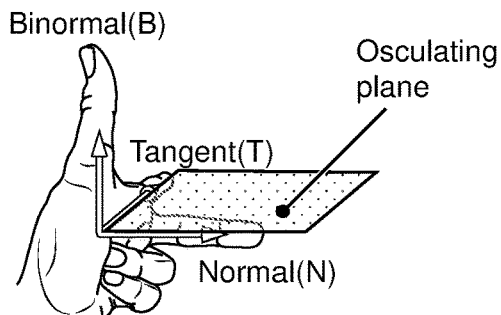

FIG. 3O illustrates a left-hand rule.

Figure 3P:
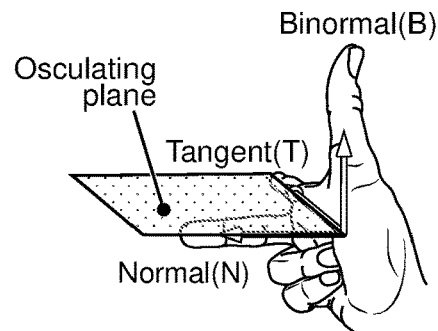

FIG. 3P illustrates a right-hand rule.

Figure 3Q:
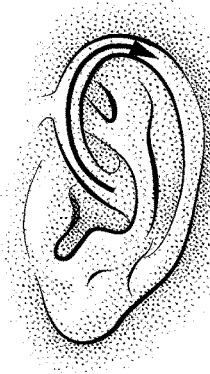

FIG. 3Q shows a left ear, including the left ear helix.

Figure 3S:
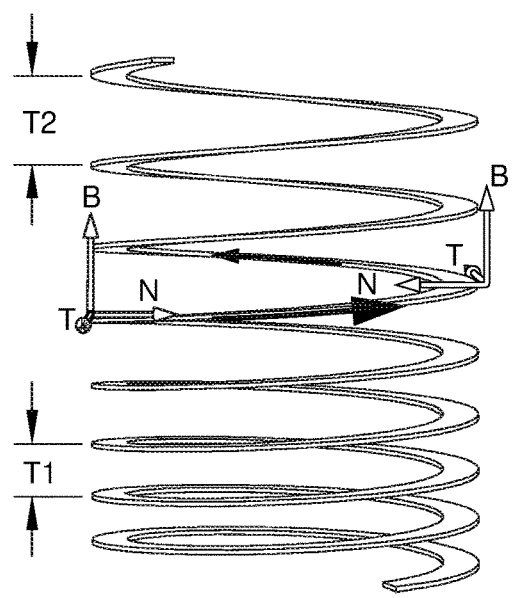
Figure 3R:
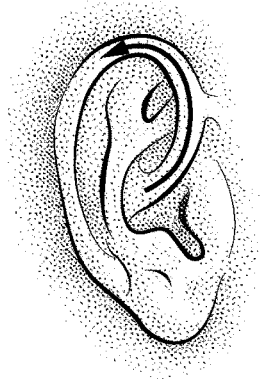

FIG. 3R shows a right ear, including the right ear helix.

FIG. 3S shows a right-hand helix.

Figure 3T:
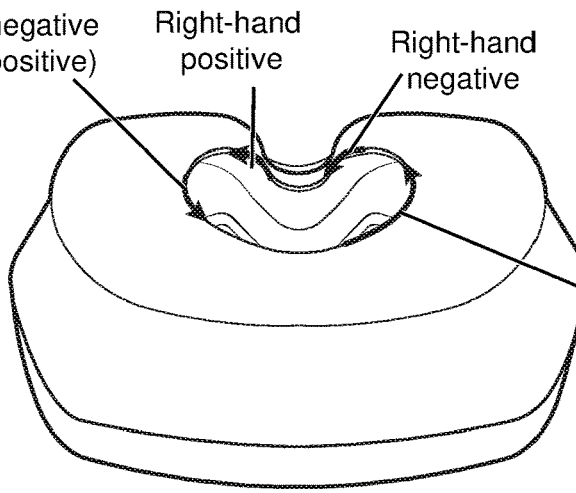

FIG. 3T shows a view of a mask, including the sign of the torsion of the space curve defined by the edge of the sealing membrane in different regions of the mask.

Figure 3U:
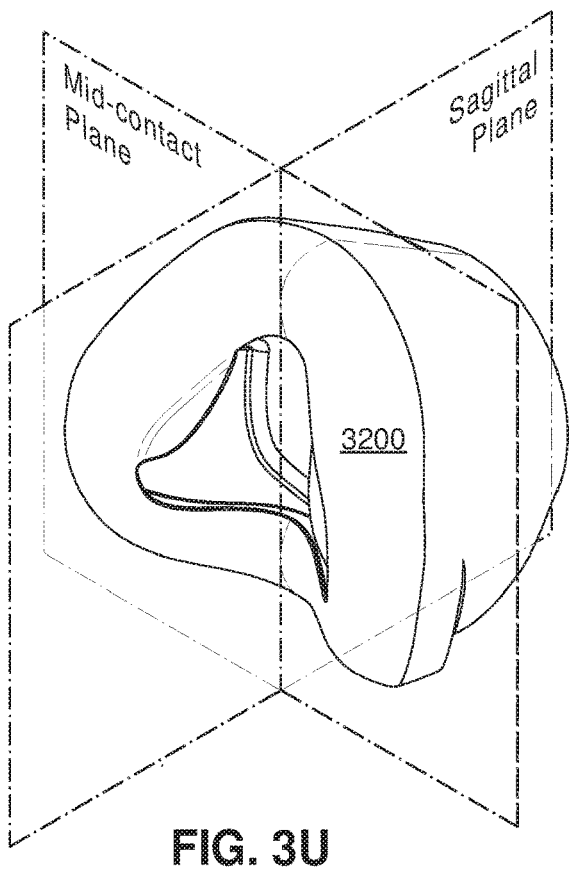

FIG. 3U shows a view of a plenum chamber 3200 showing a sagittal plane and a mid-contact plane.

Figure 3V:
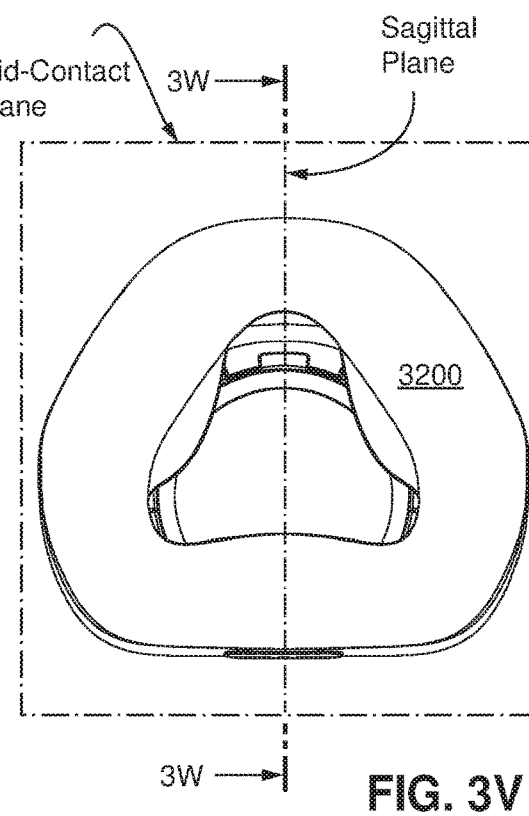

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
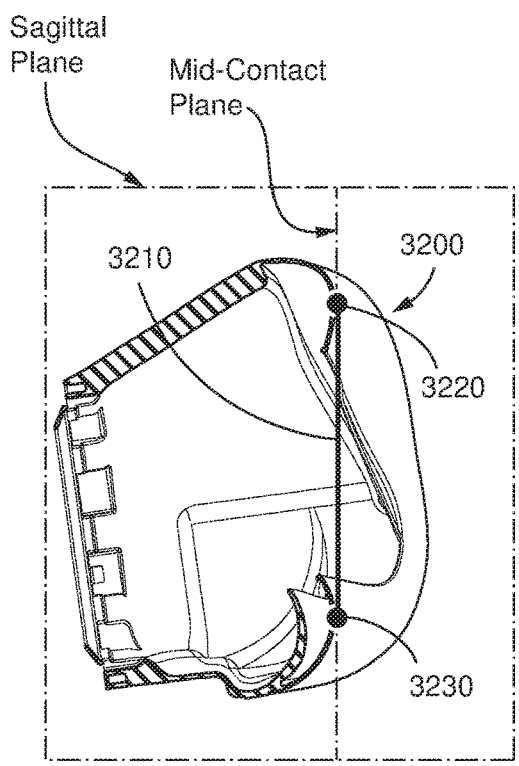

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
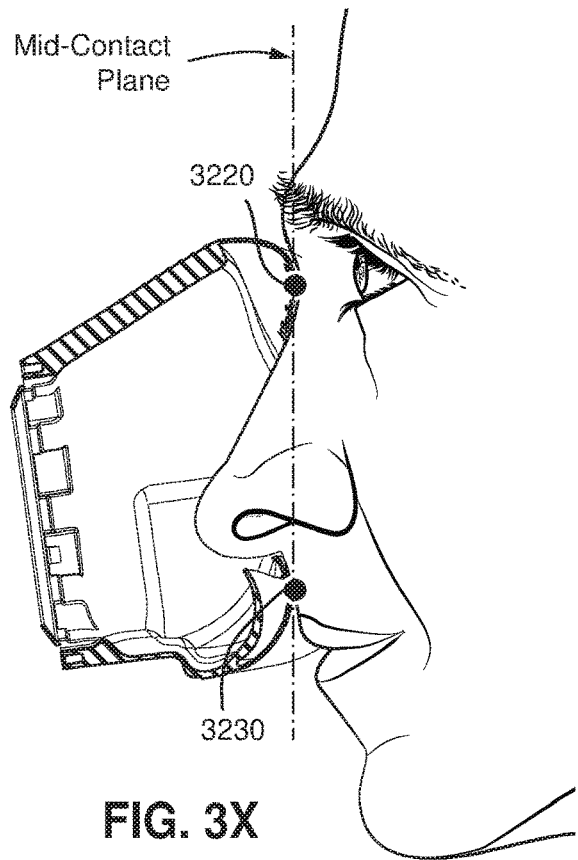

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
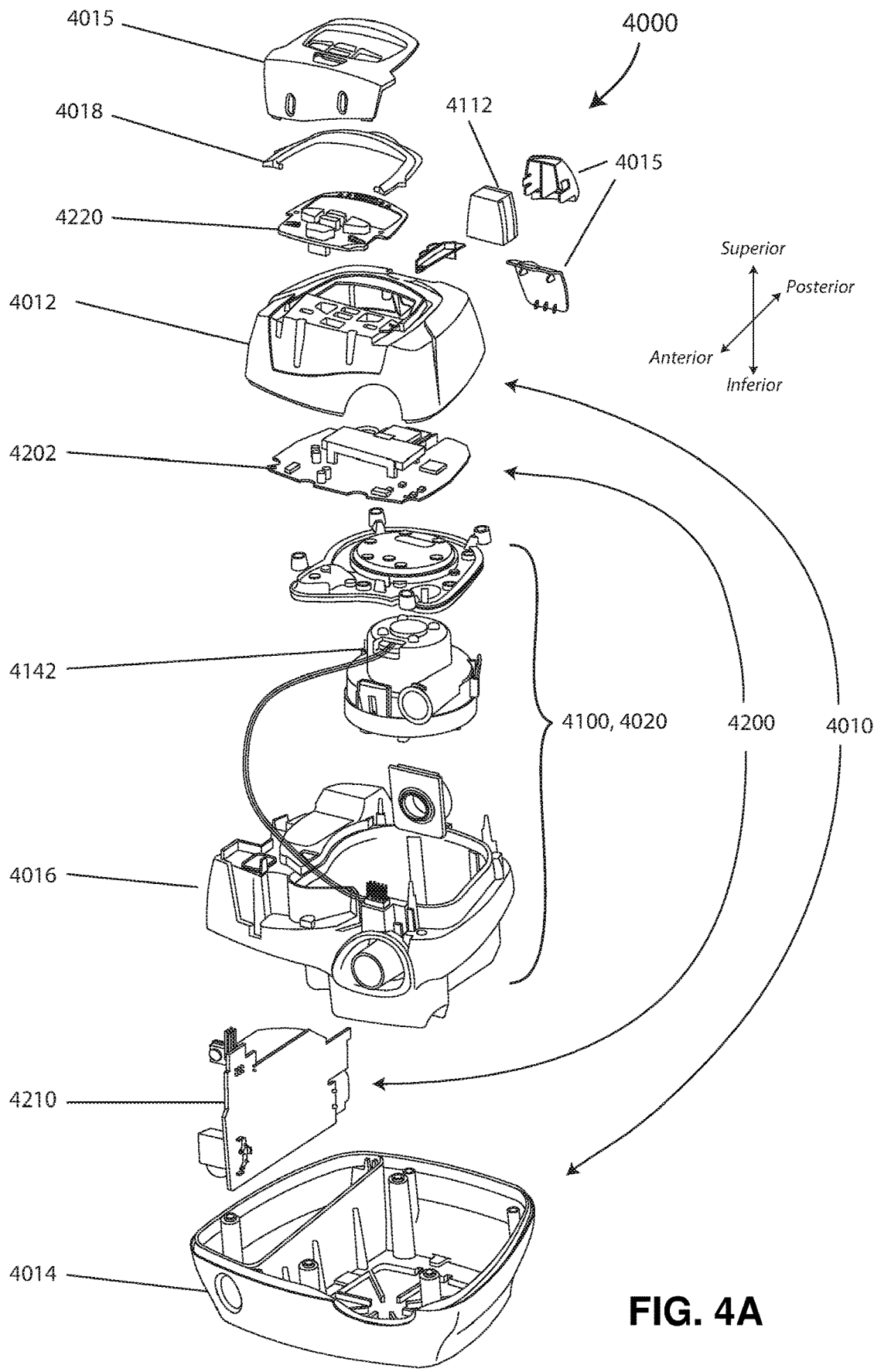

FIG. 4A shows an RPT device in accordance with one form of the present technology.

Figure 4B:
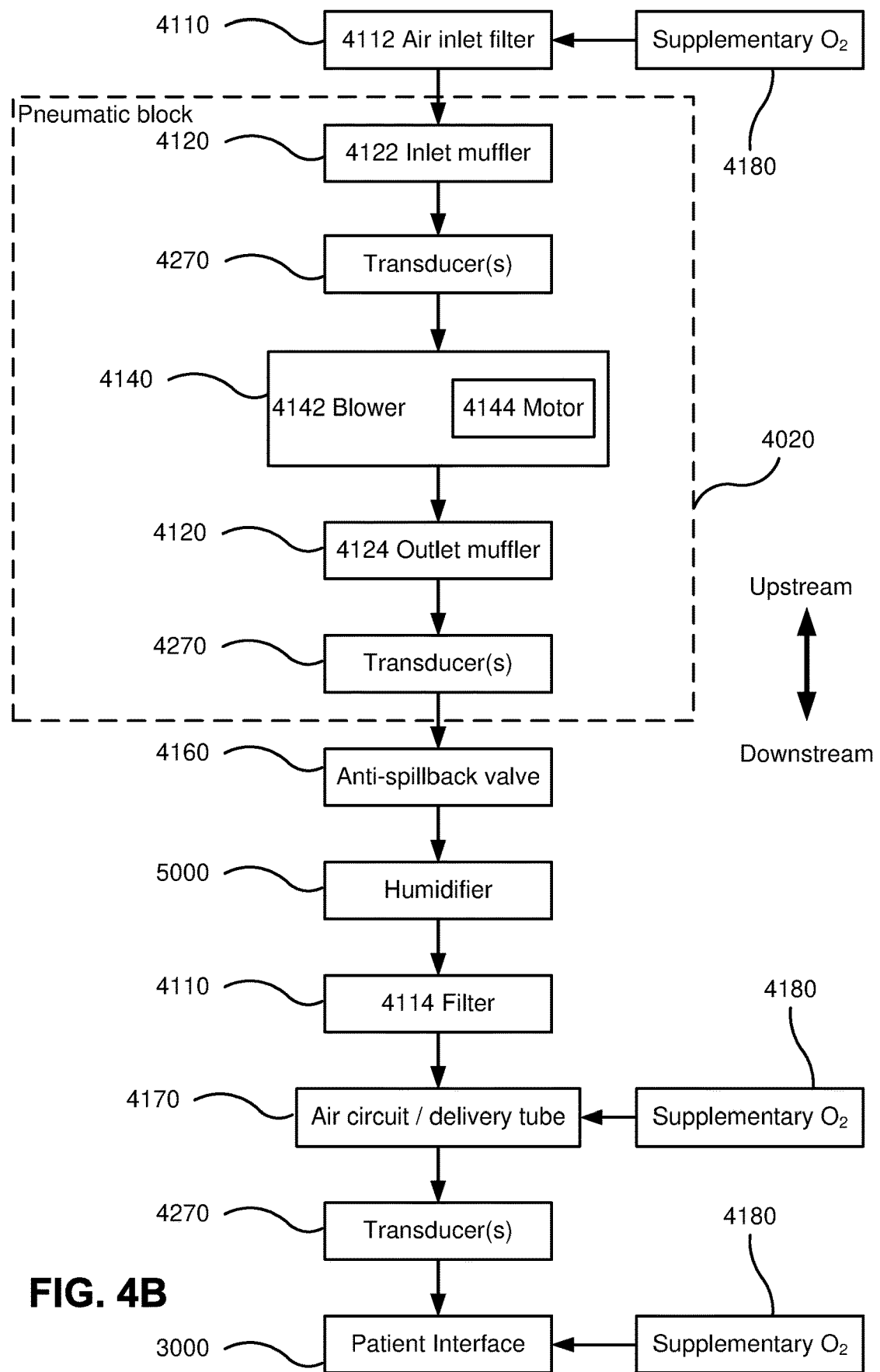

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
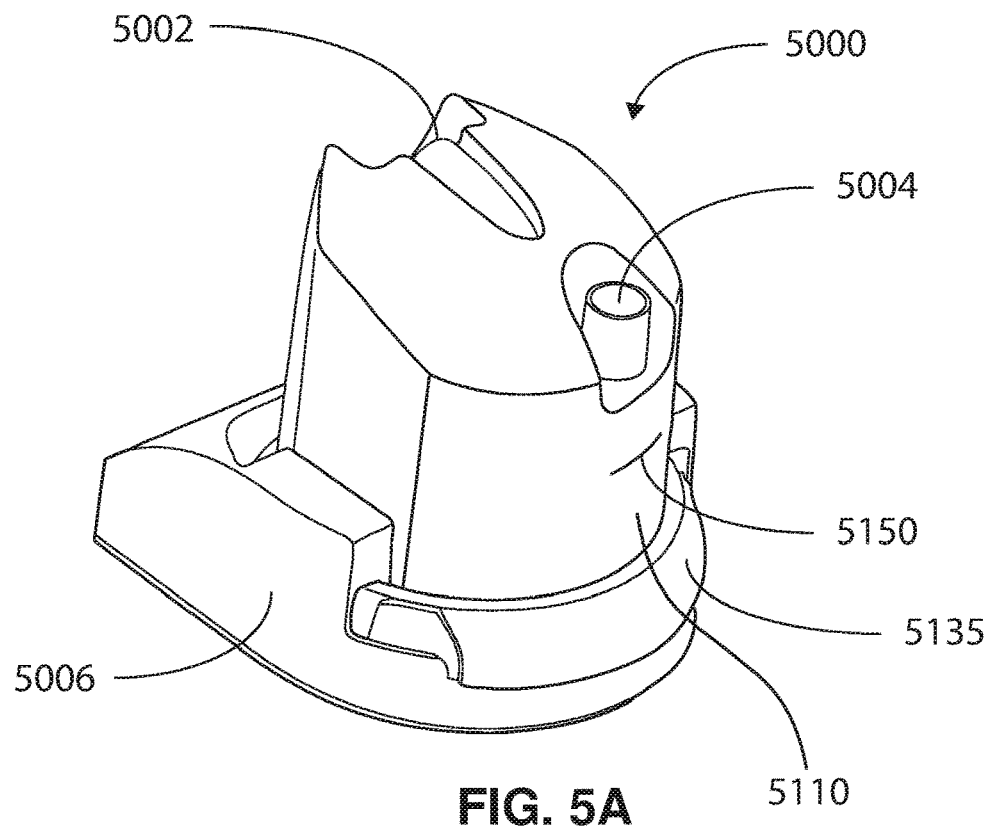

FIG. 5A shows an isometric view of a humidifier in accordance with one form of the present technology.

Figure 5B:
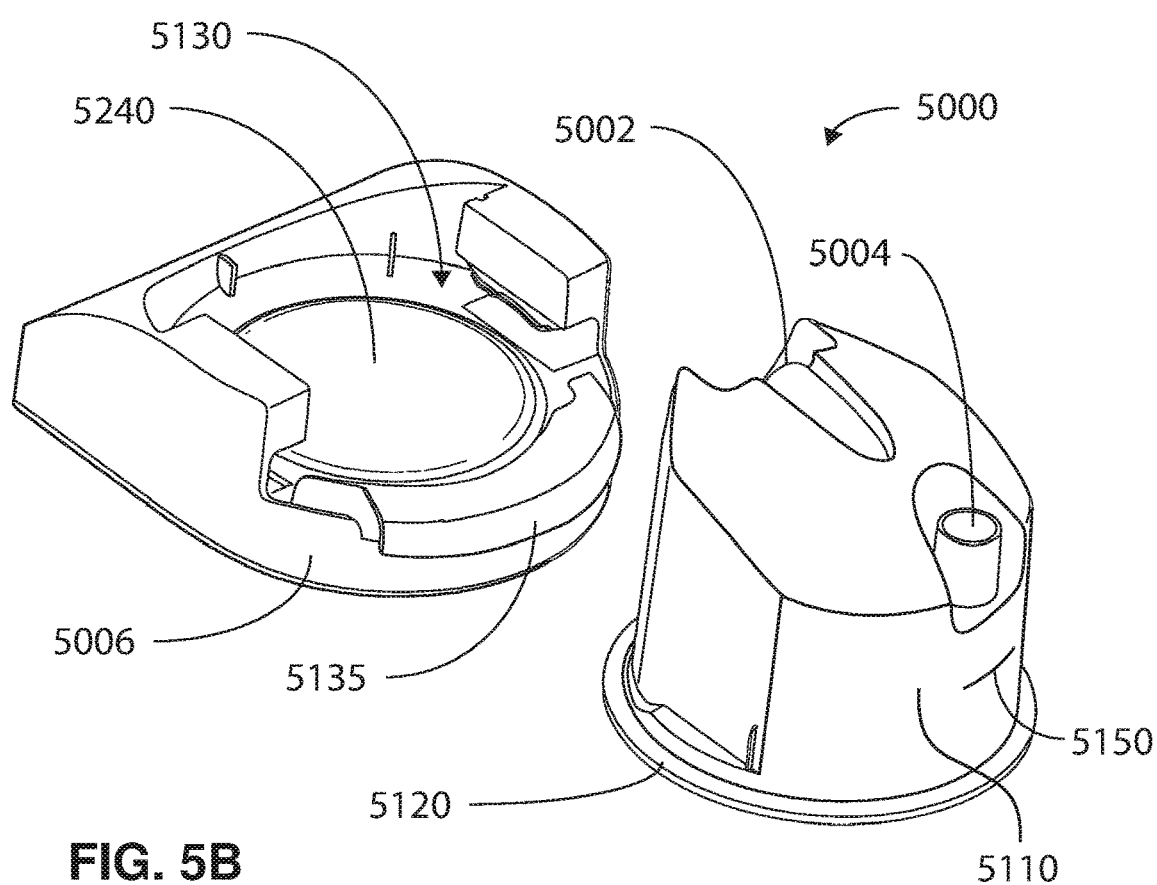

FIG. 5B shows an isometric view of a humidifier in accordance with one form of the present technology, showing a humidifier reservoir 5110 removed from the humidifier reservoir dock 5130.

Figure 5C:
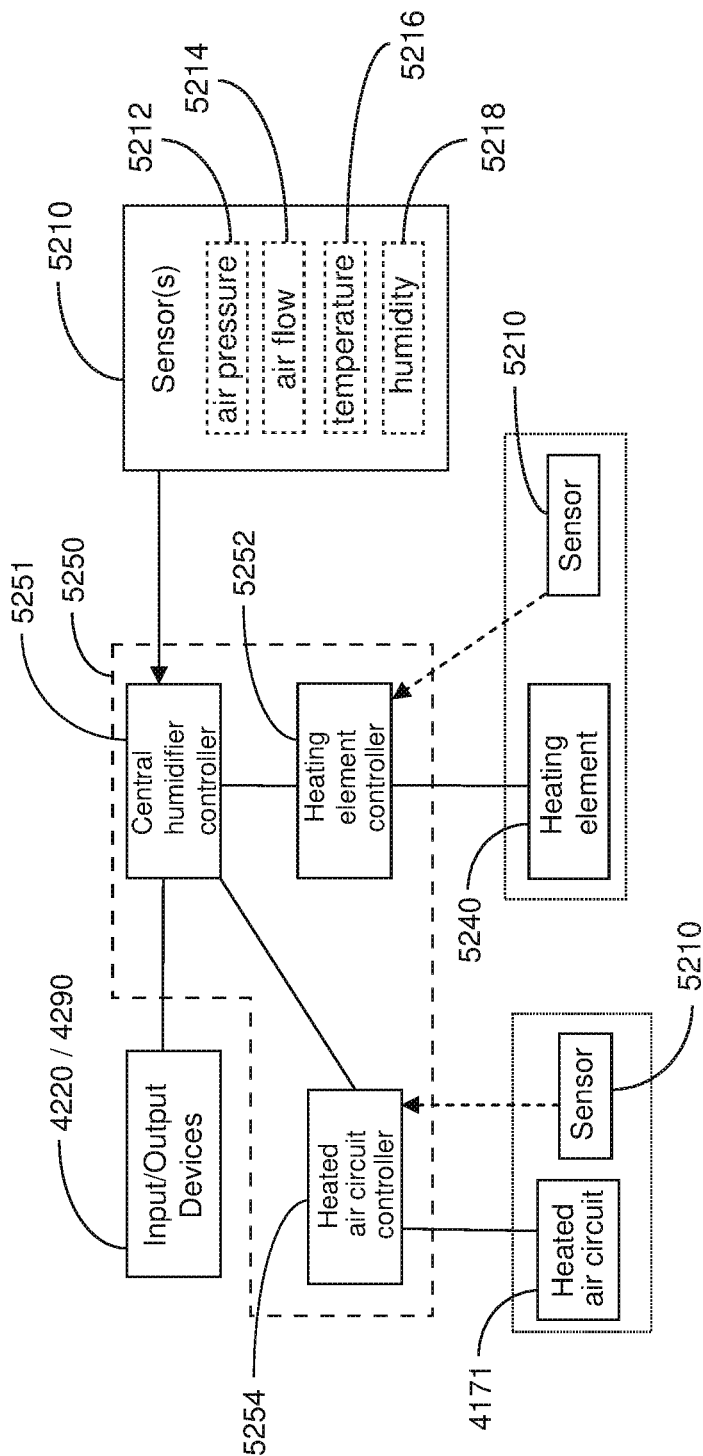

FIG. 5C shows a schematic of a humidifier in accordance with one form of the present technology.

4.6 Breathing Waveform

Figure 6:
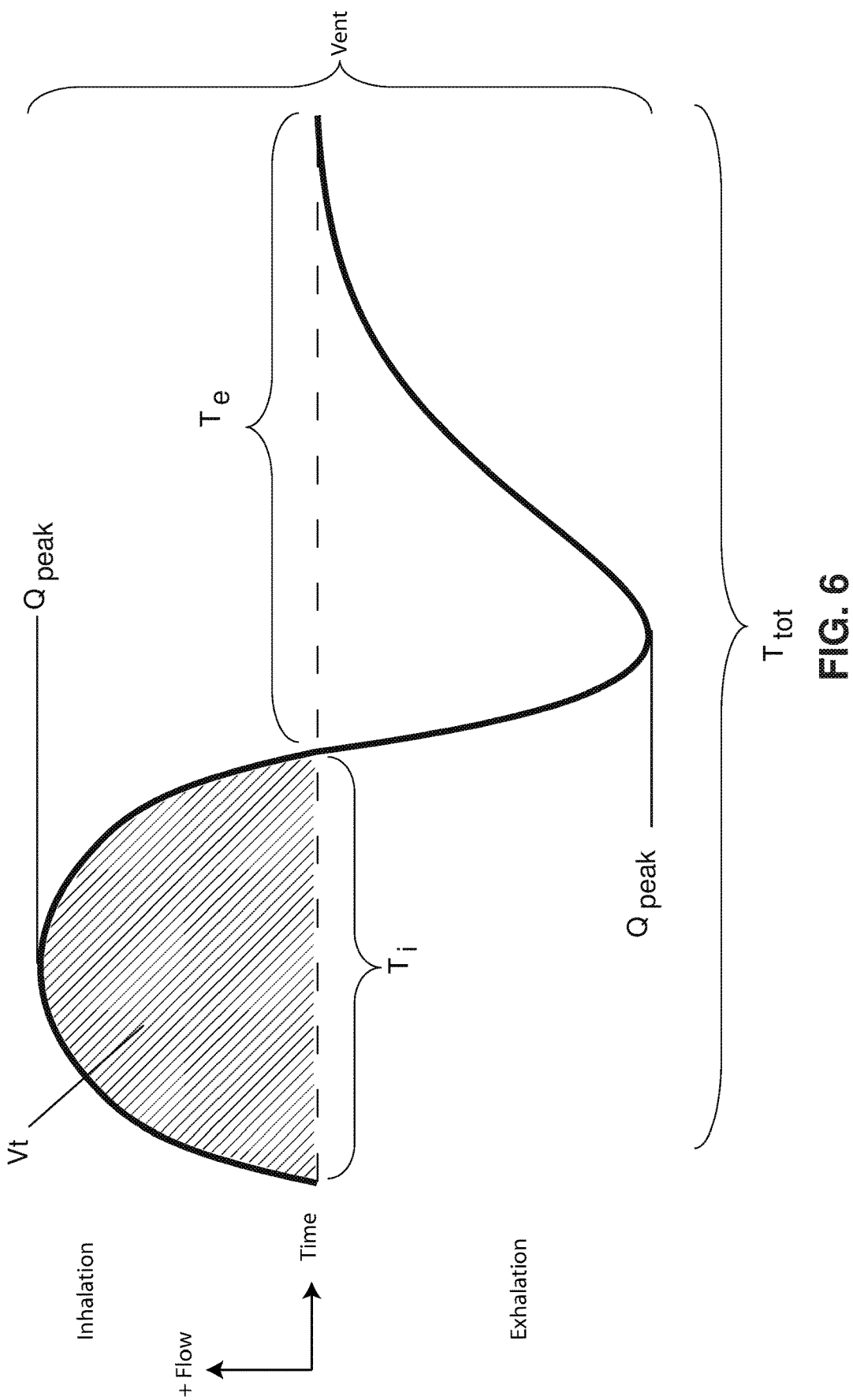

FIG. 6 shows a model typical breath waveform of a person while sleeping.

4.7 Patient Interface According to the Present Technology

Figure 7:
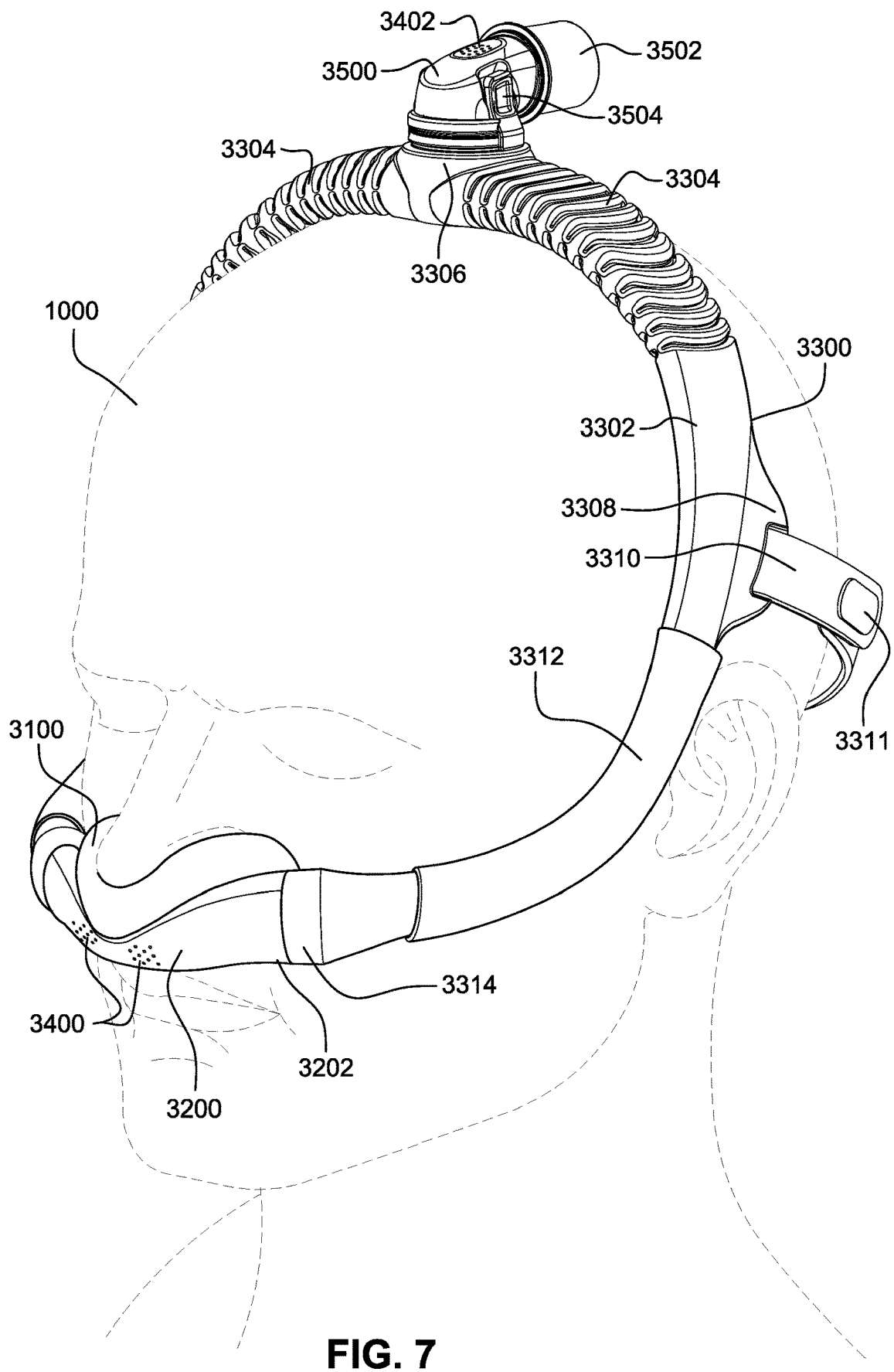

FIG. 7 is an anterolateral view from a superior position of a patient interface according to an example of the present technology worn by a patient.

Figure 8:
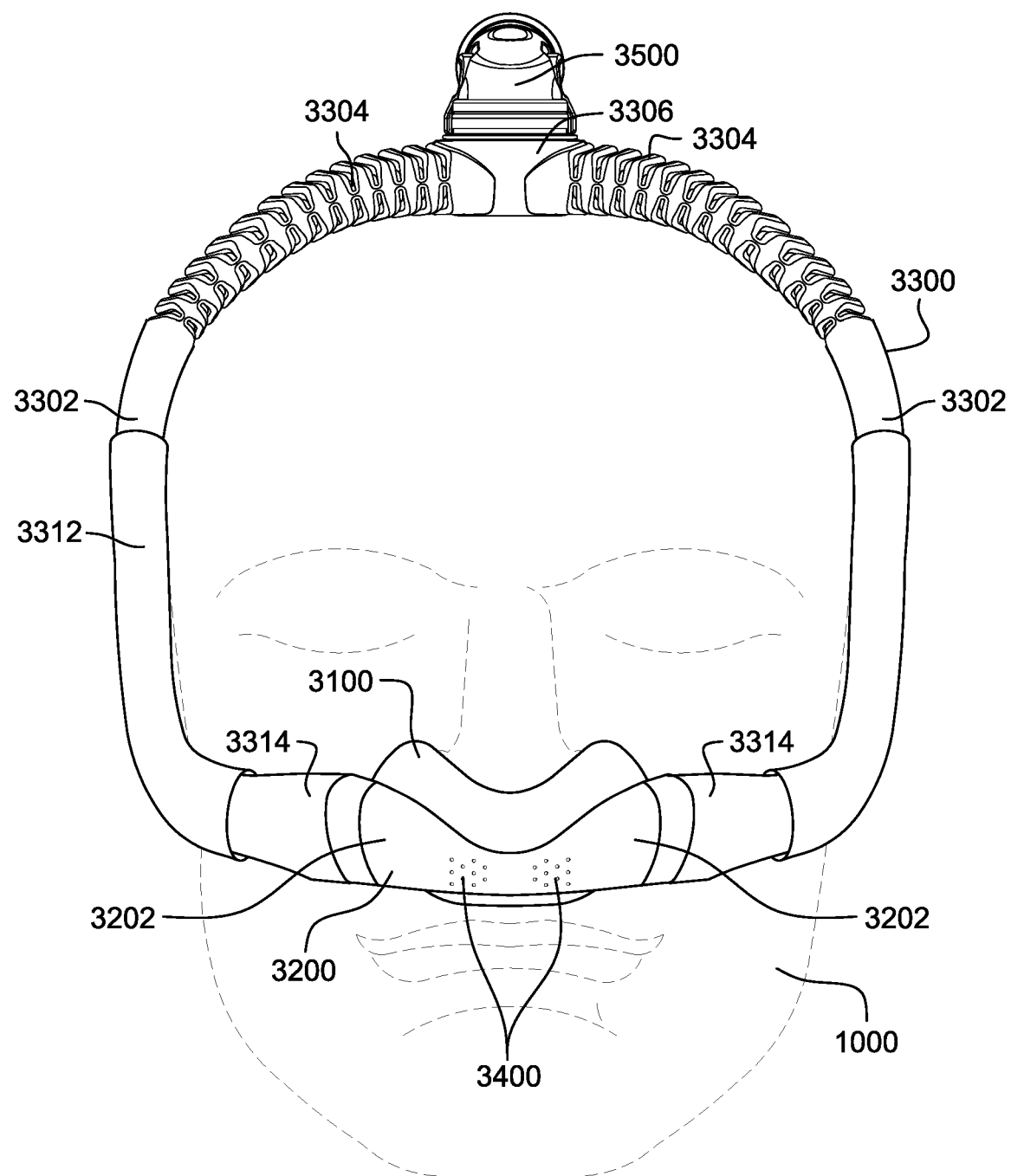

FIG. 8 is an anterior view of a patient interface according to an example of the present technology worn by a patient.

Figure 9:
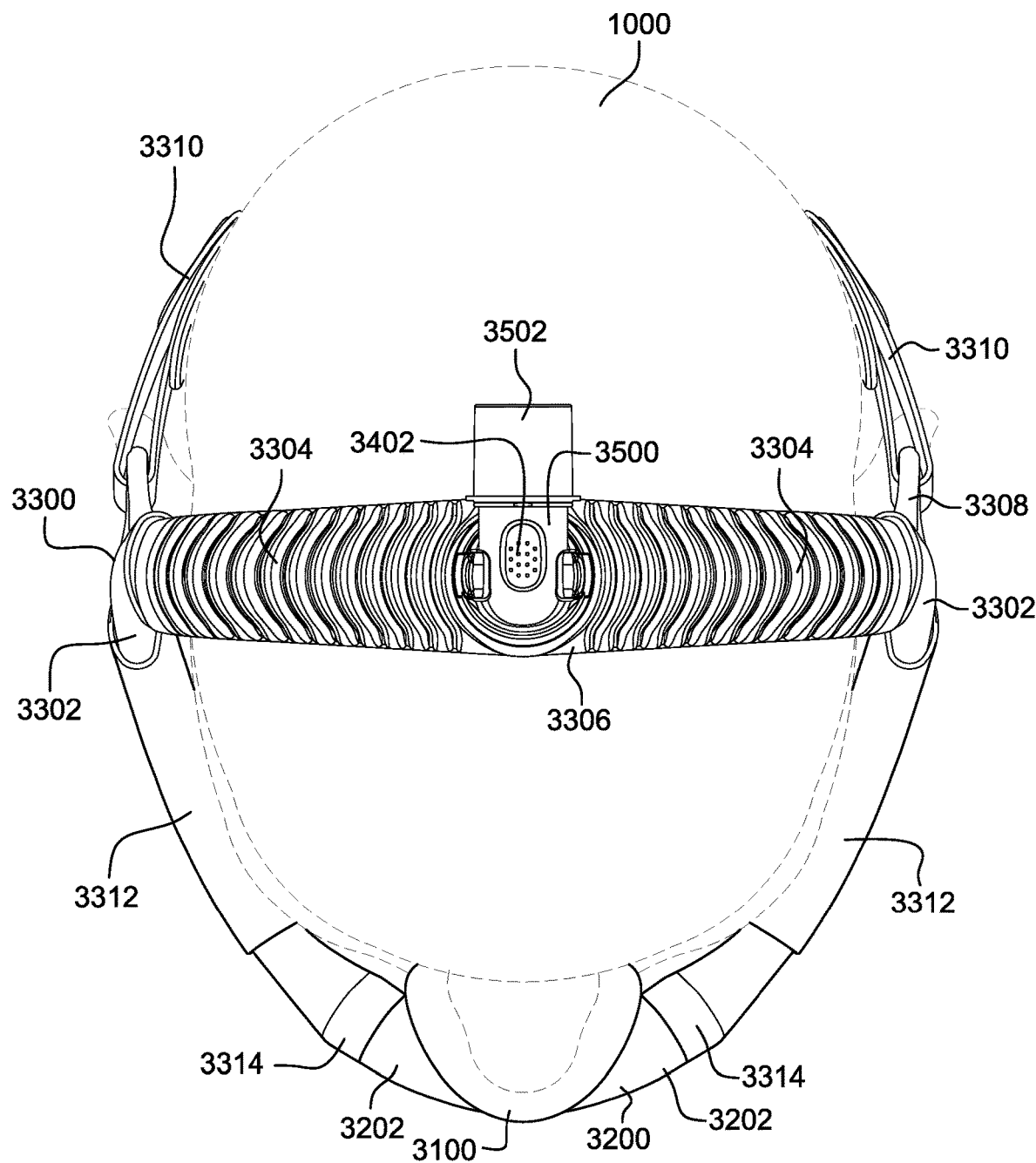

FIG. 9 is a superior view of a patient interface according to an example of the present technology worn by a patient.

Figure 10:
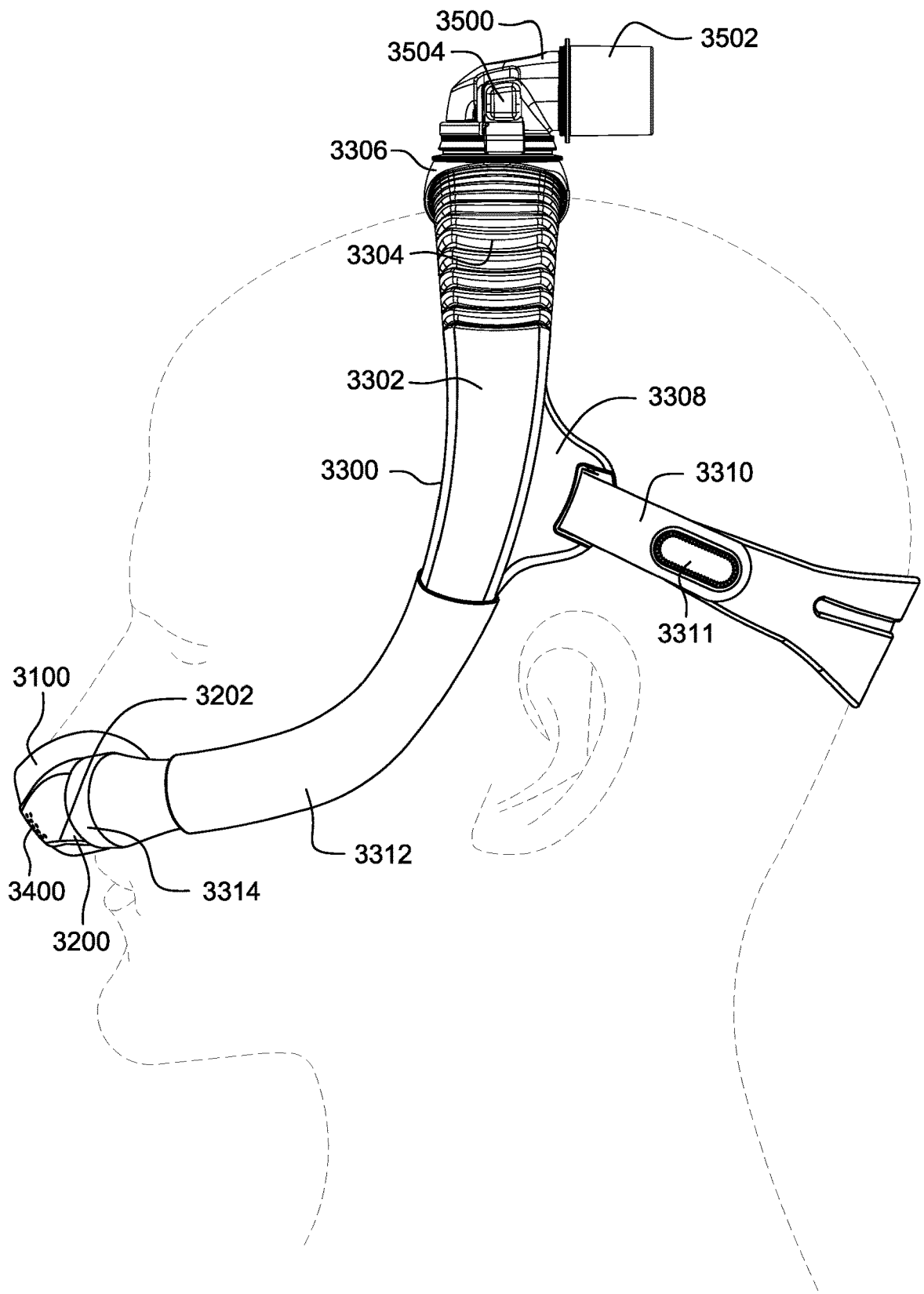

FIG. 10 is a lateral view of a patient interface according to an example of the present technology worn by a patient.

Figure 11:
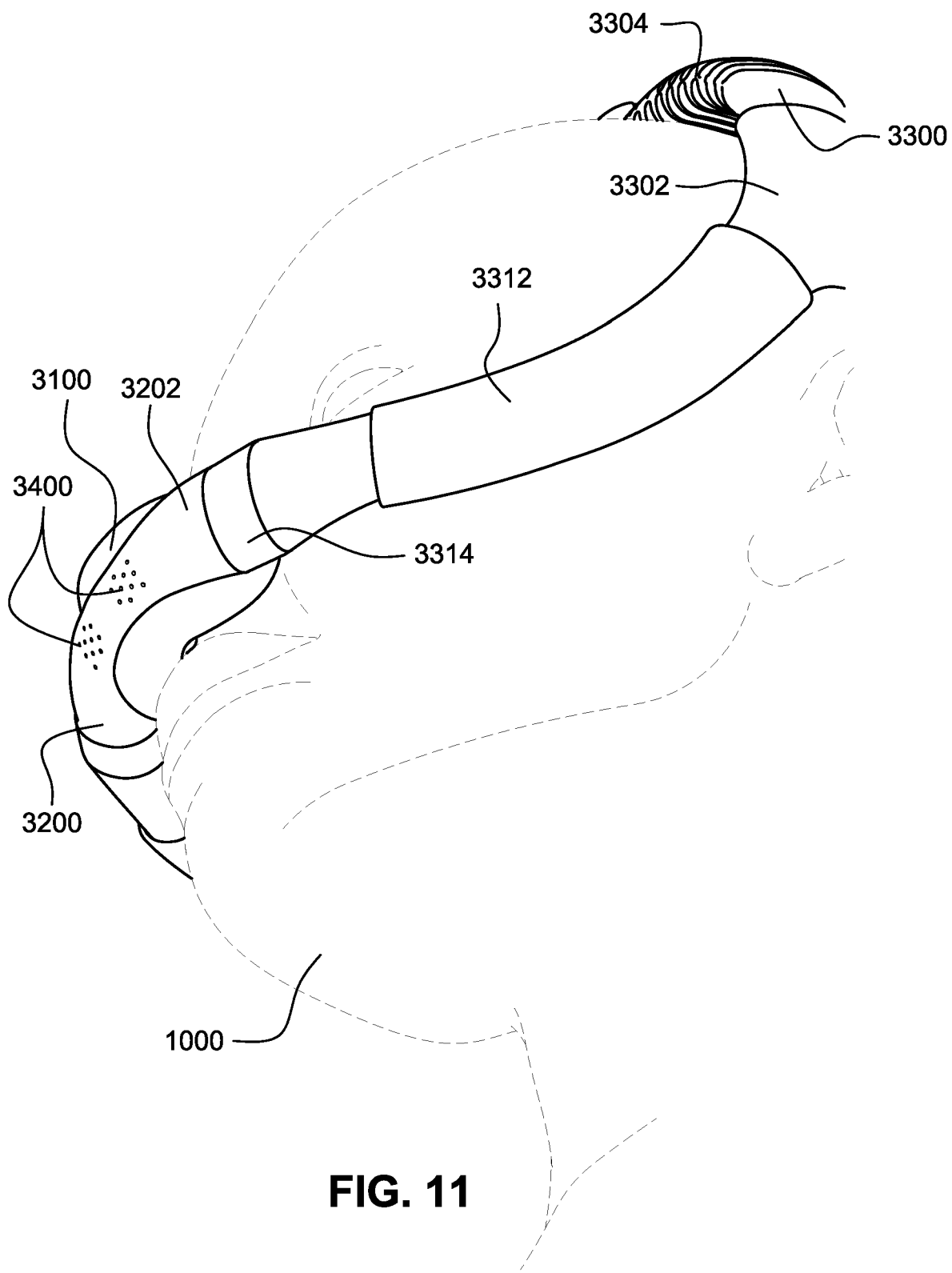

FIG. 11 is an anterolateral view from a superior position of a patient interface according to an example of the present technology worn by a patient.

Figure 12:
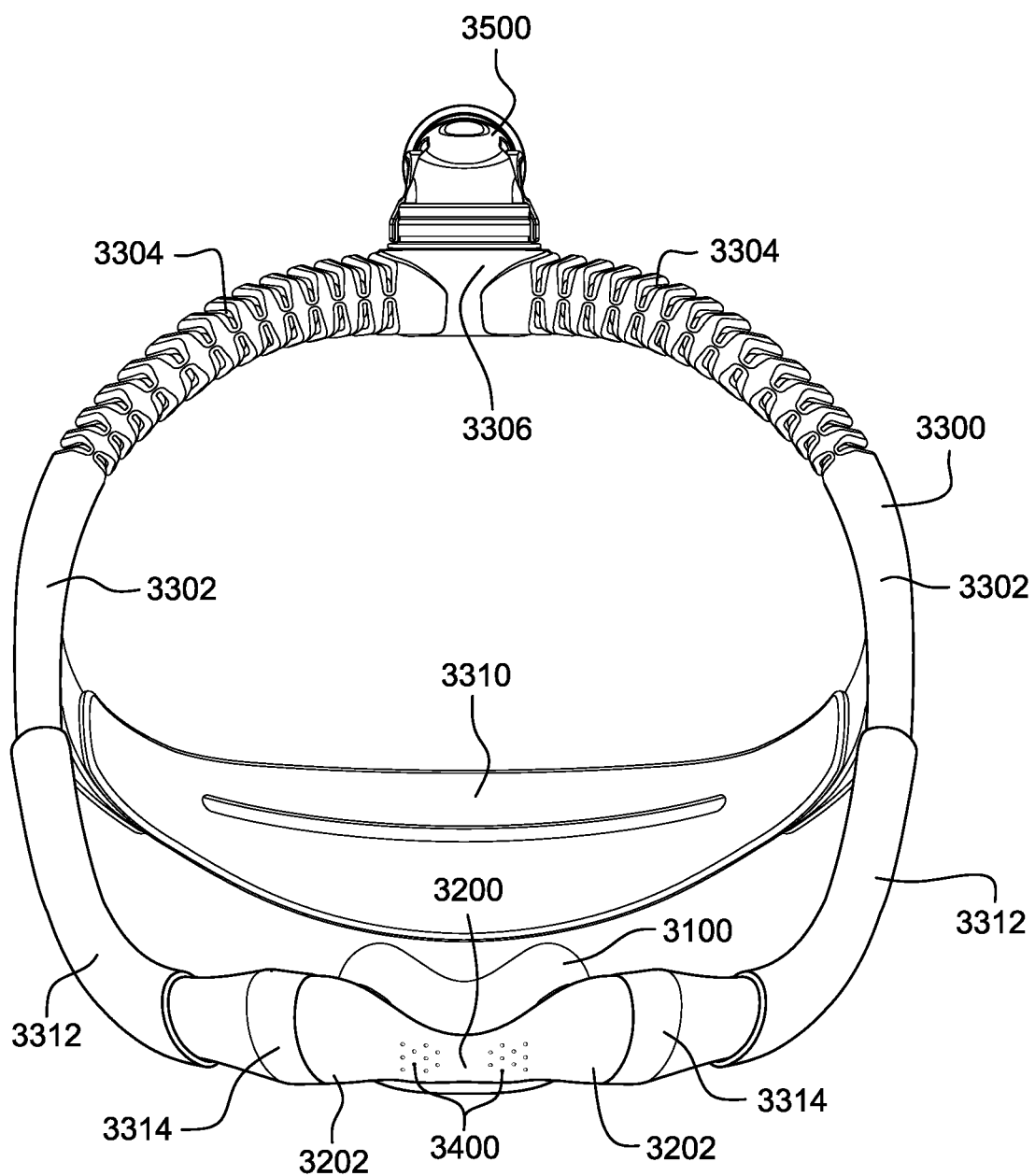

FIG. 12 is an anterior view of a patient interface according to an example of the present technology.

Figure 13:
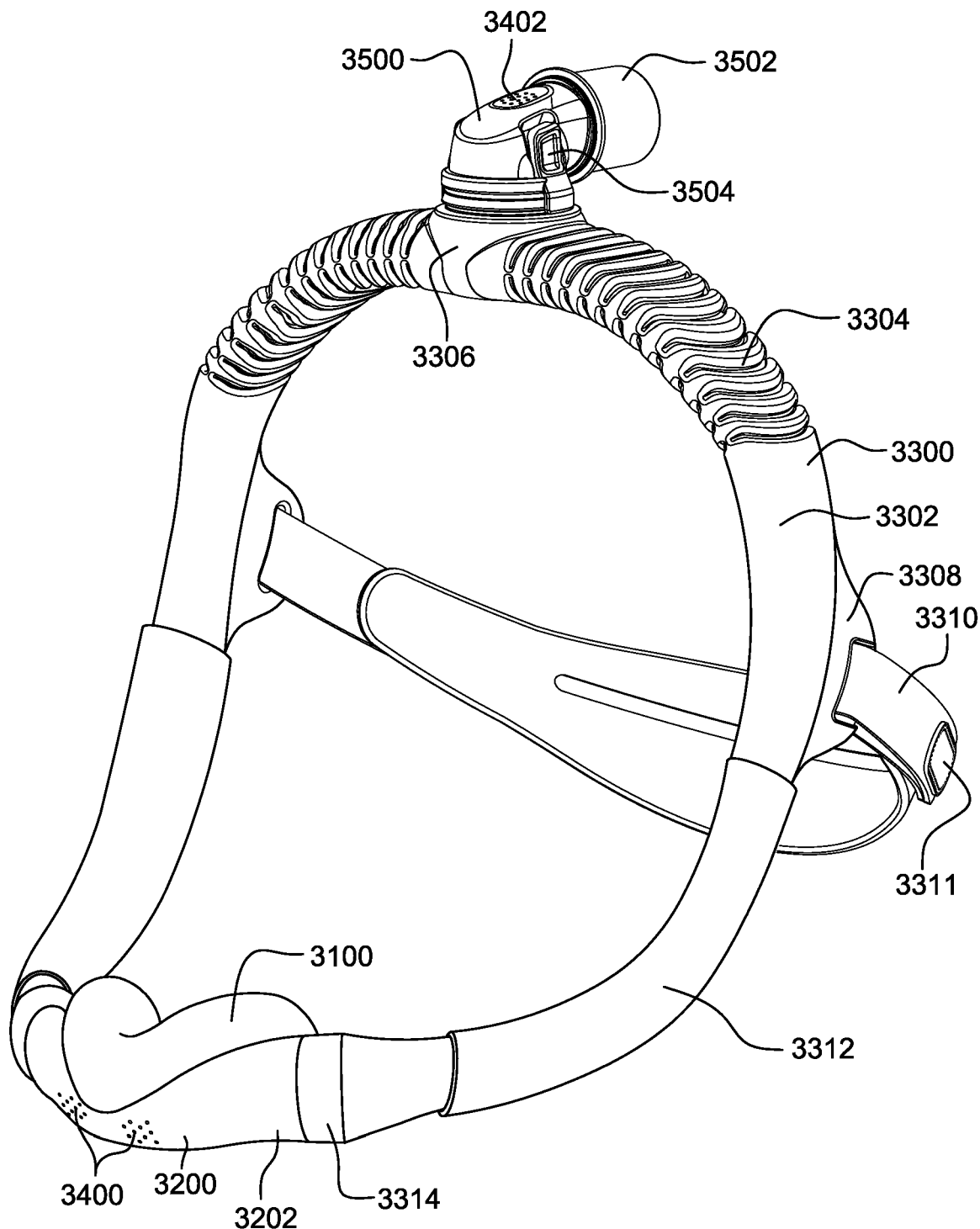

FIG. 13 is an anterolateral view from a superior position of a patient interface according to an example of the present technology.

Figure 14:
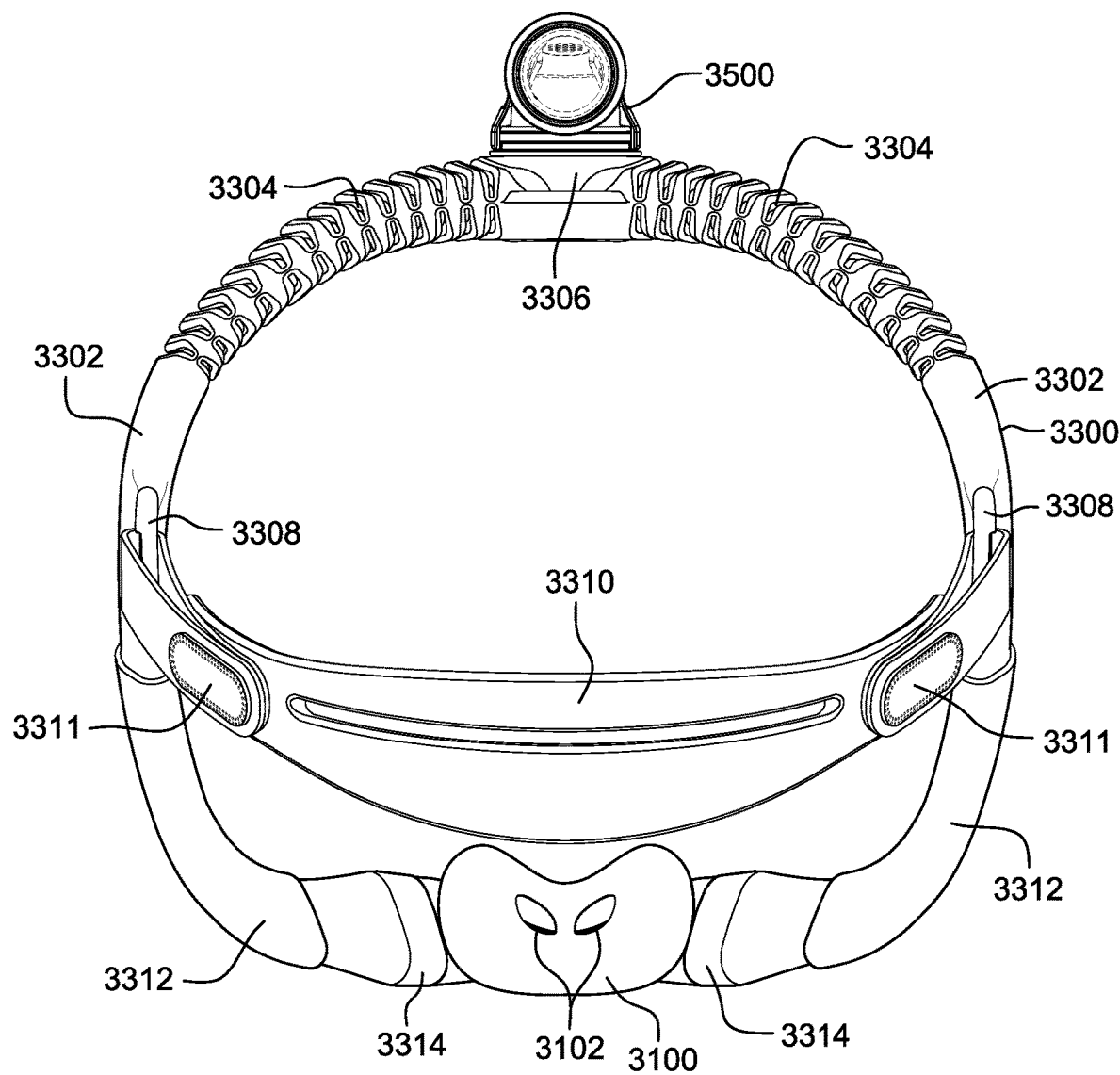

FIG. 14 is a posterior view of a patient interface according to an example of the present technology.

Figure 15:
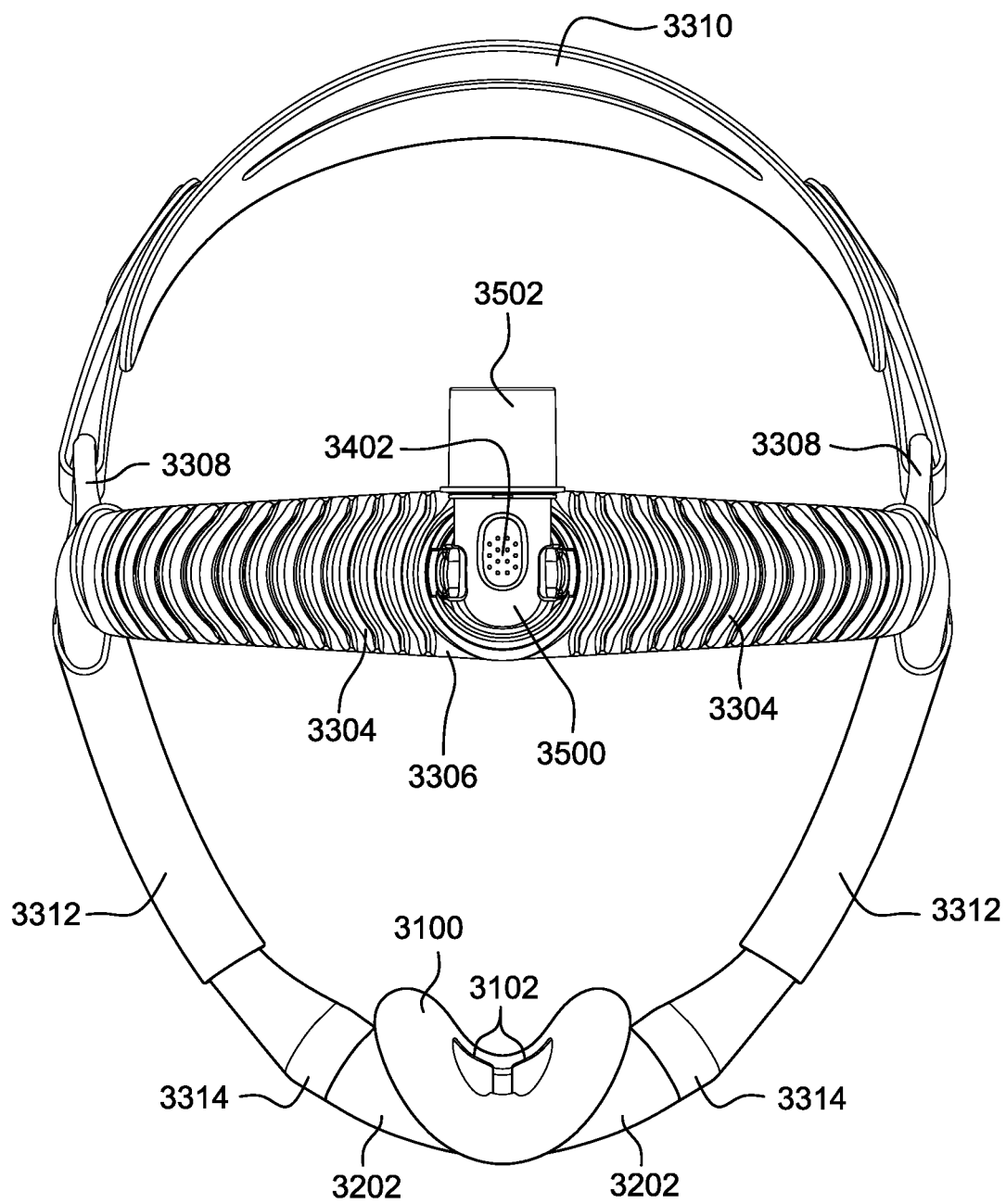

FIG. 15 is a superior view of a patient interface according to an example of the present technology.

Figure 16:
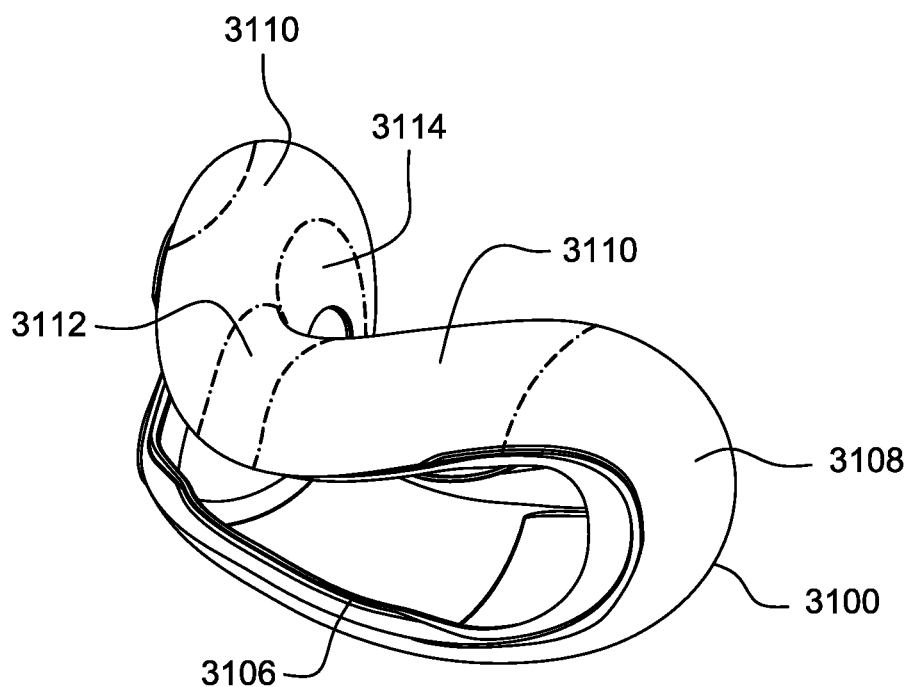

FIG. 16 is an anterolateral view from a superior position of a seal-forming structure for a patient interface according to an example of the present technology.

Figure 17:
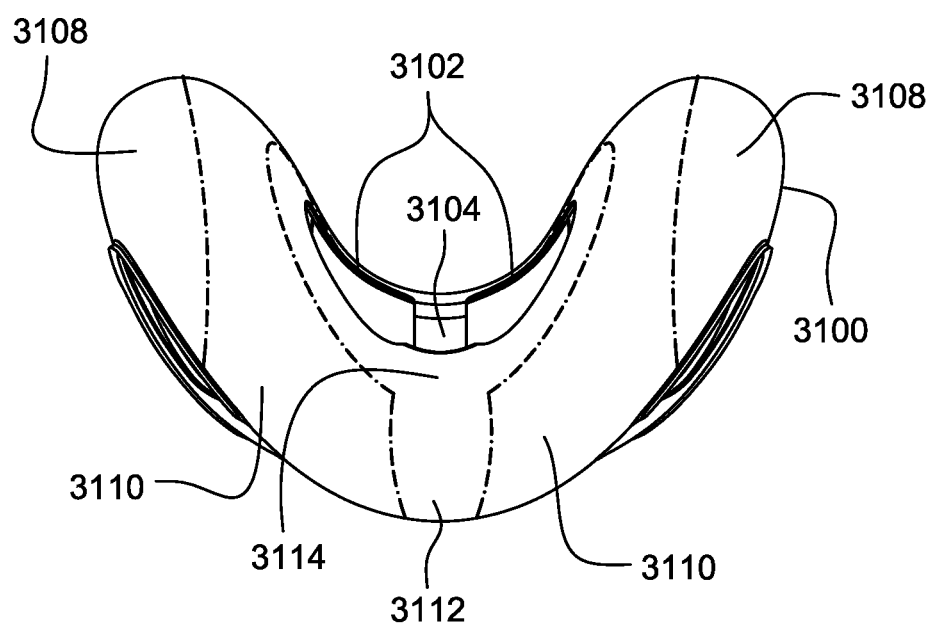

FIG. 17 is a superior view of a seal-forming structure for a patient interface according to an example of the present technology.

Figure 18:
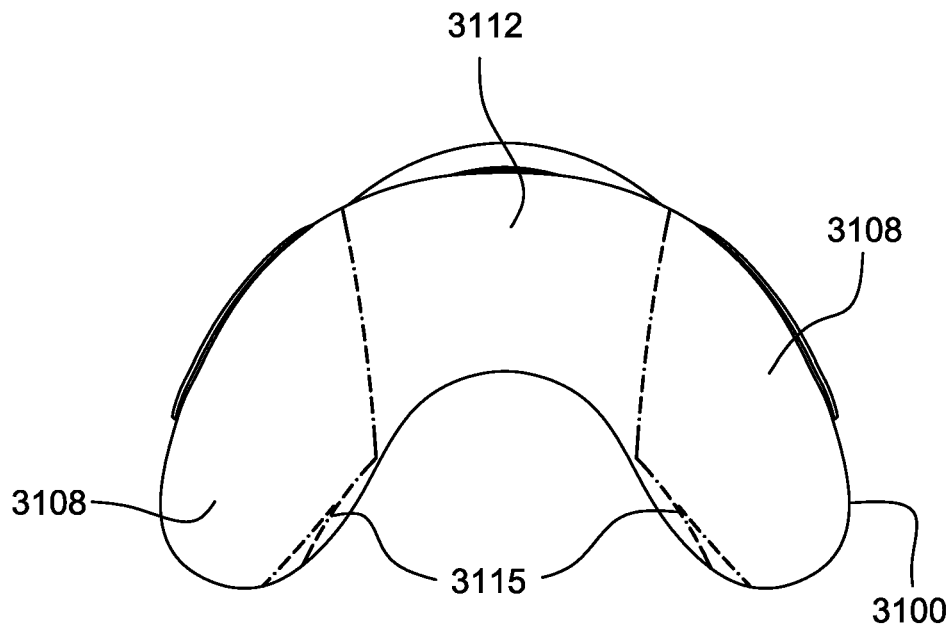

FIG. 18 is an inferior view of a seal-forming structure for a patient interface according to an example of the present technology.

Figure 19:
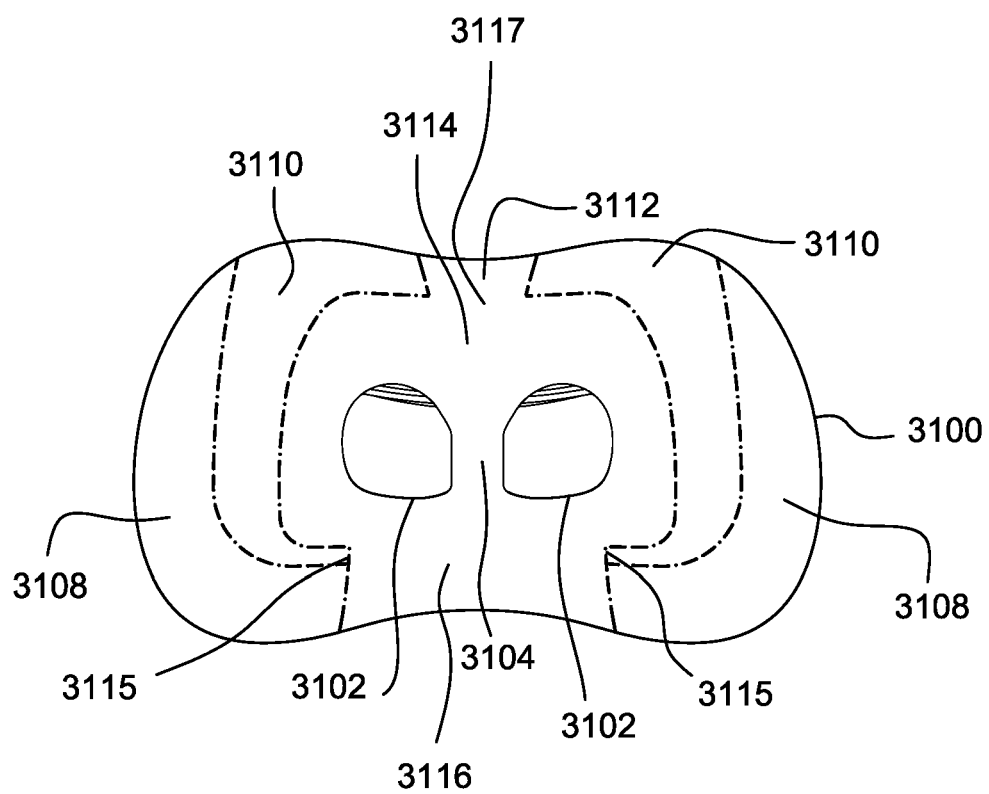

FIG. 19 is a posterior view of a seal-forming structure for a patient interface according to an example of the present technology.

Figure 20:
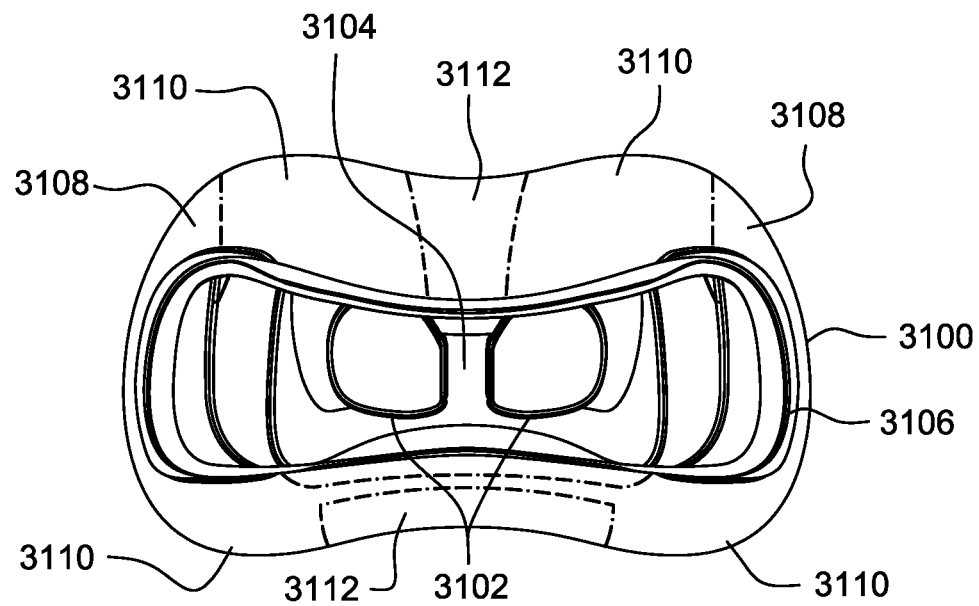

FIG. 20 is an anterior view of a seal-forming structure for a patient interface according to an example of the present technology.

Figure 21:
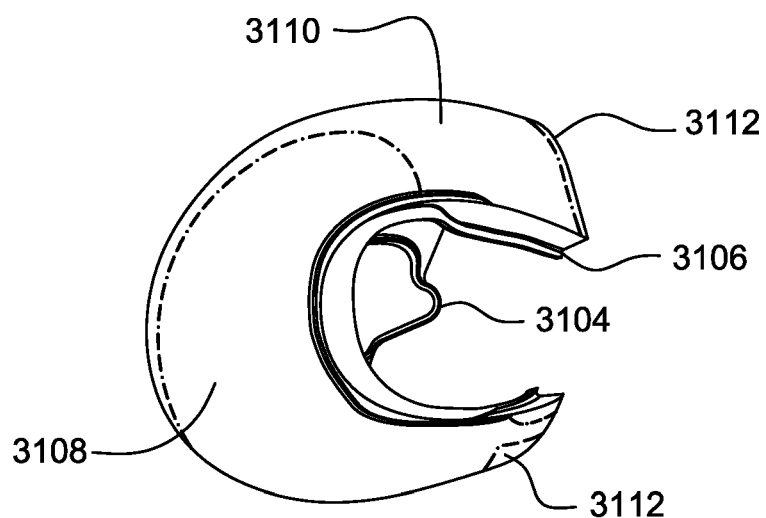

FIG. 21 is a lateral view of a seal-forming structure for a patient interface according to an example of the present technology.

Figure 22:
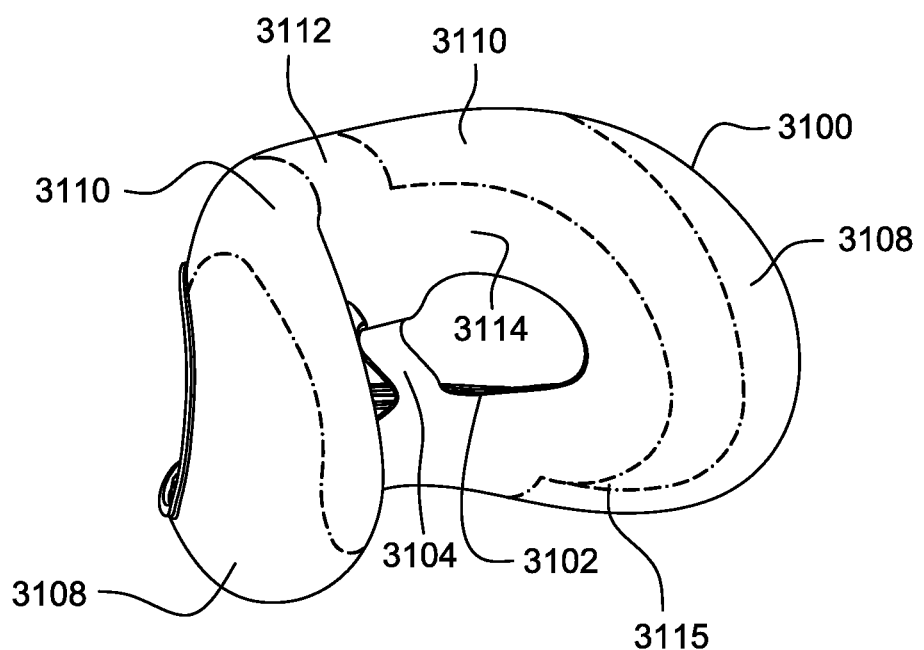

FIG. 22 is a posterolateral view from a superior position of a seal-forming structure for a patient interface according to an example of the present technology.

Figure 23:
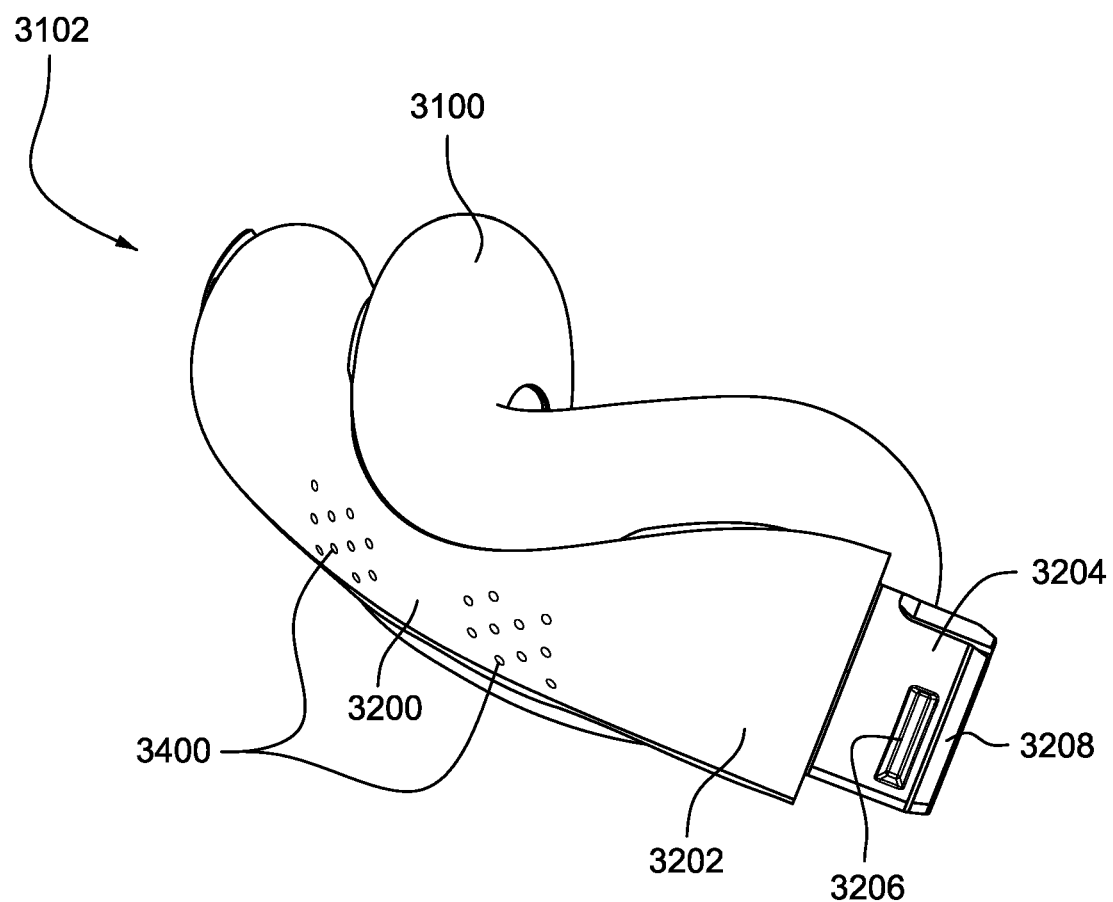

FIG. 23 is an anterolateral view from a superior position of a seal-forming structure and a plenum chamber for a patient interface according to an example of the present technology.

Figure 24:
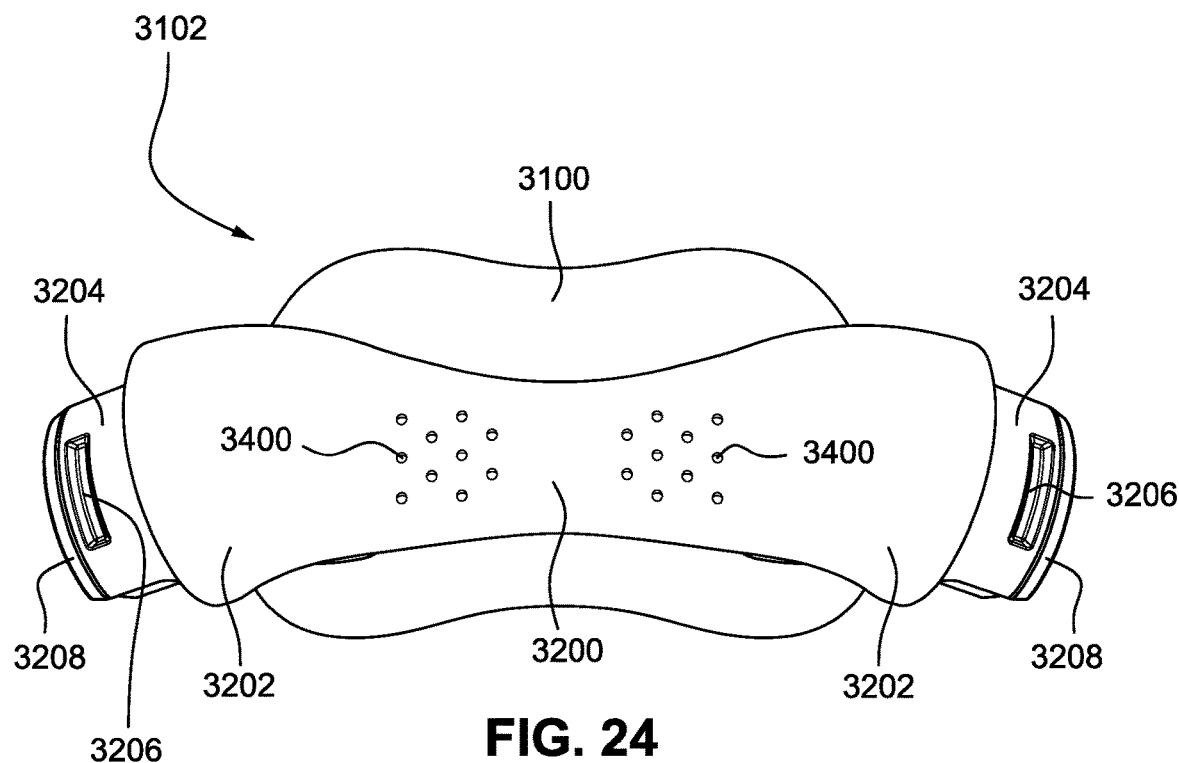

FIG. 24 is an anterior view of a seal-forming structure and a plenum chamber for a patient interface according to an example of the present technology.

Figure 25:
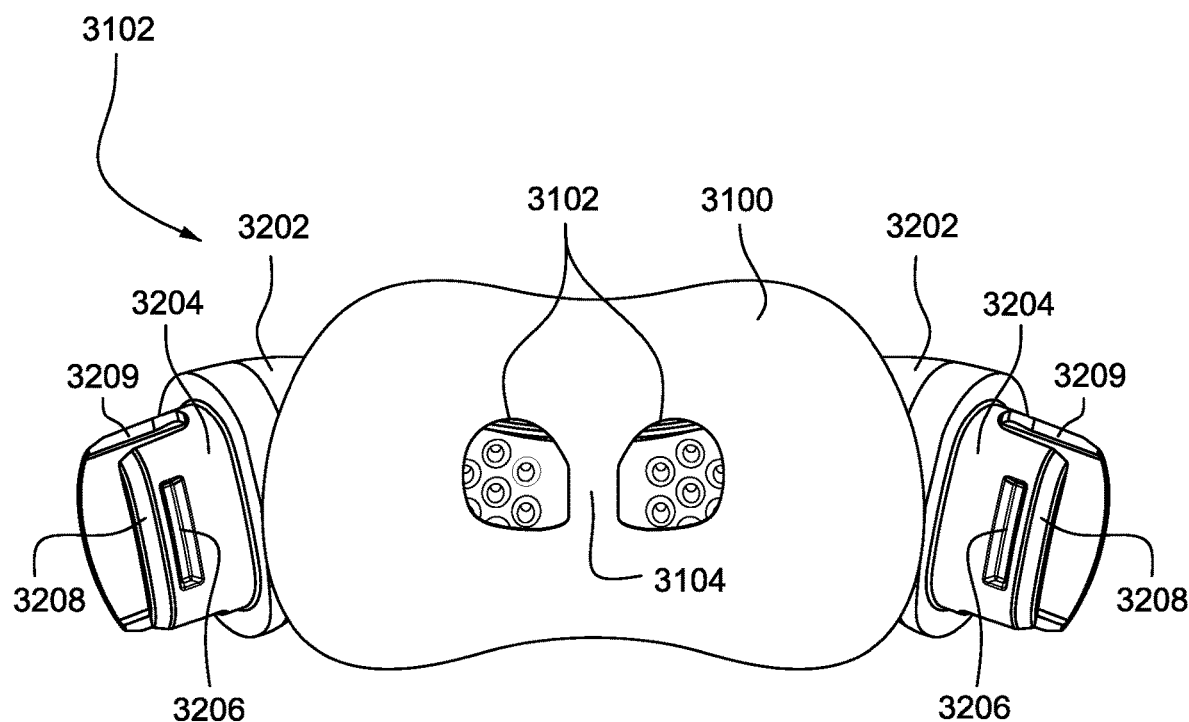

FIG. 25 is a posterior view of a seal-forming structure and a plenum chamber for a patient interface according to an example of the present technology.

Figure 26:
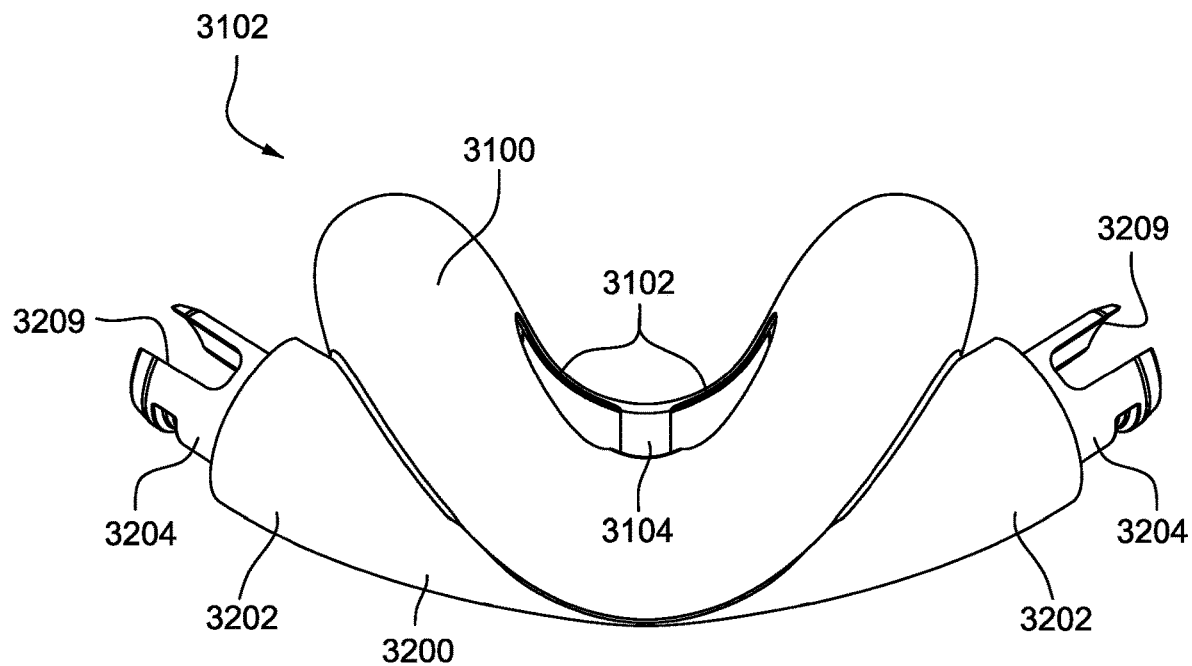

FIG. 26 is a superior view of a seal-forming structure and a plenum chamber for a patient interface according to an example of the present technology.

Figure 27:
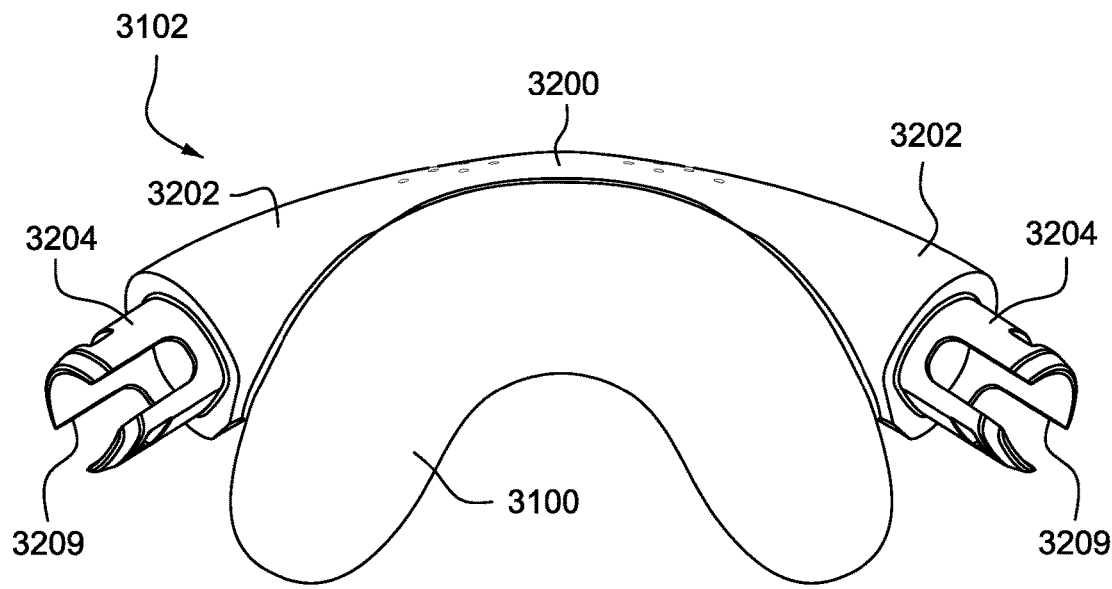

FIG. 27 is an inferior view of a seal-forming structure and a plenum chamber for a patient interface according to an example of the present technology.

Figure 28:
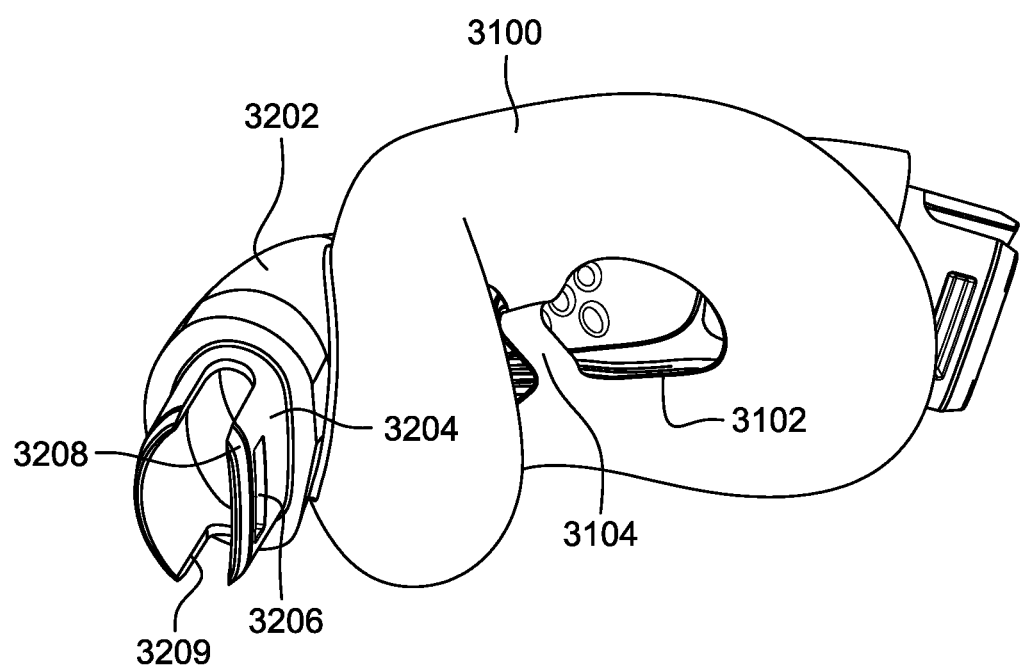

FIG. 28 is a posterolateral view from a superior position of a seal-forming structure and a plenum chamber for a patient interface according to an example of the present technology.

Figure 29:
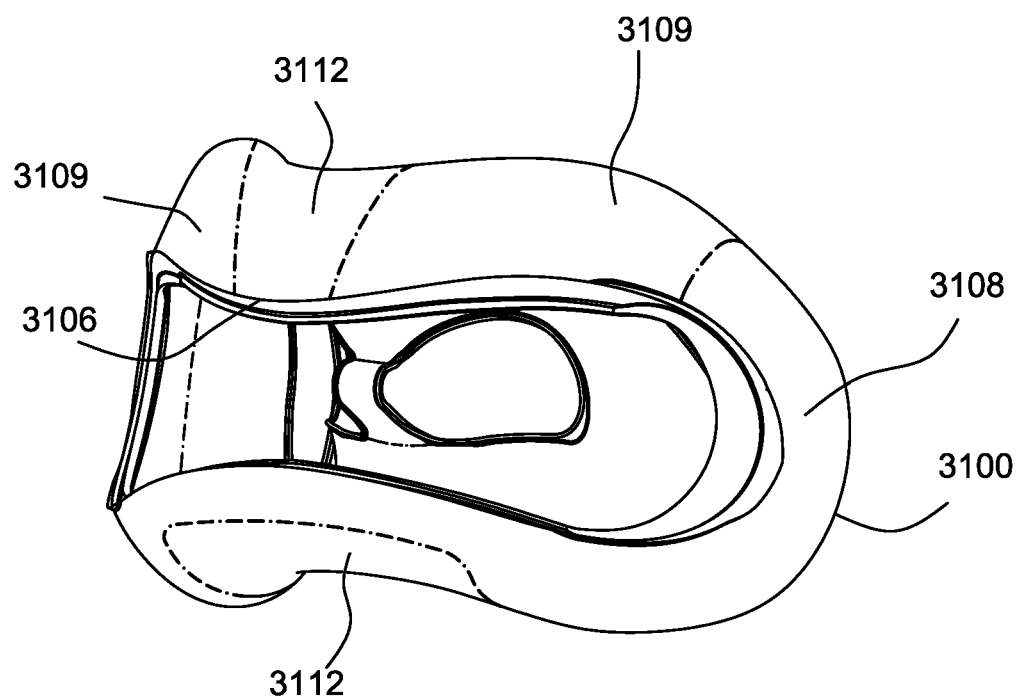

FIG. 29 is an anterolateral view of a seal-forming structure for a patient interface according to an example of the present technology.

Figure 30:
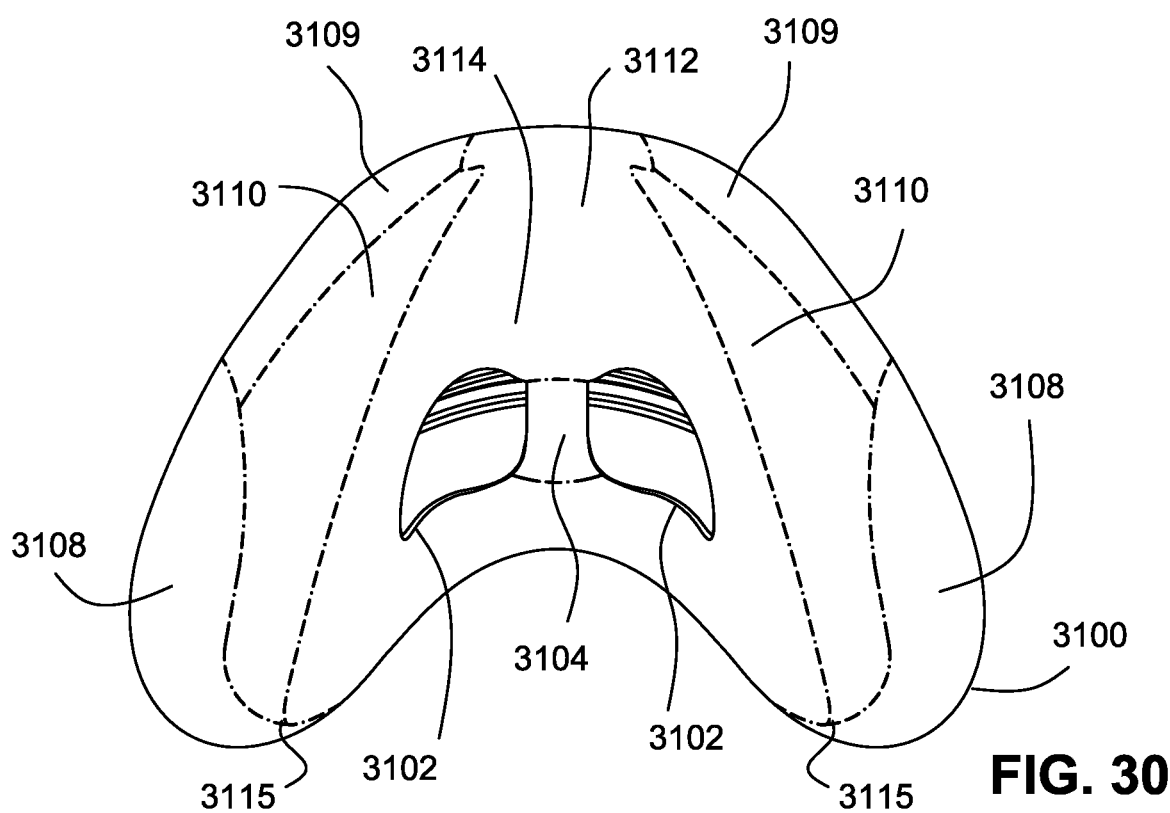

FIG. 30 is a superior view of a seal-forming structure for a patient interface according to an example of the present technology.

Figure 31:
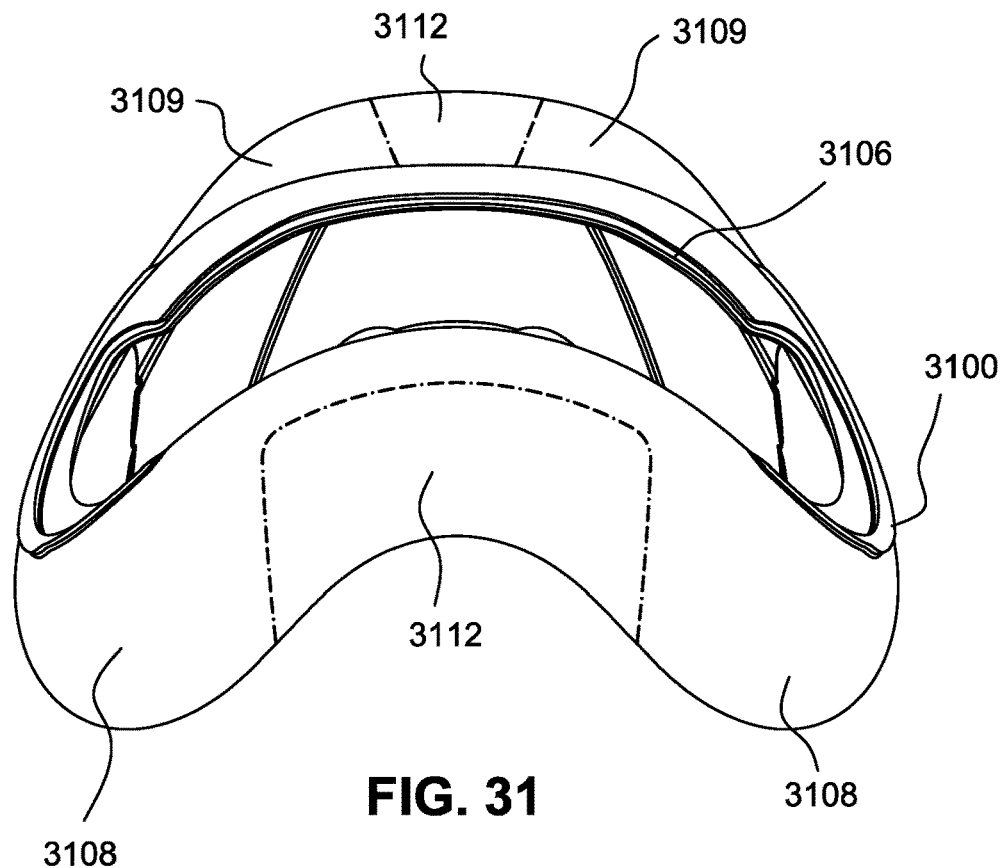

FIG. 31 is an inferior view of a seal-forming structure for a patient interface according to an example of the present technology.

Figure 32:
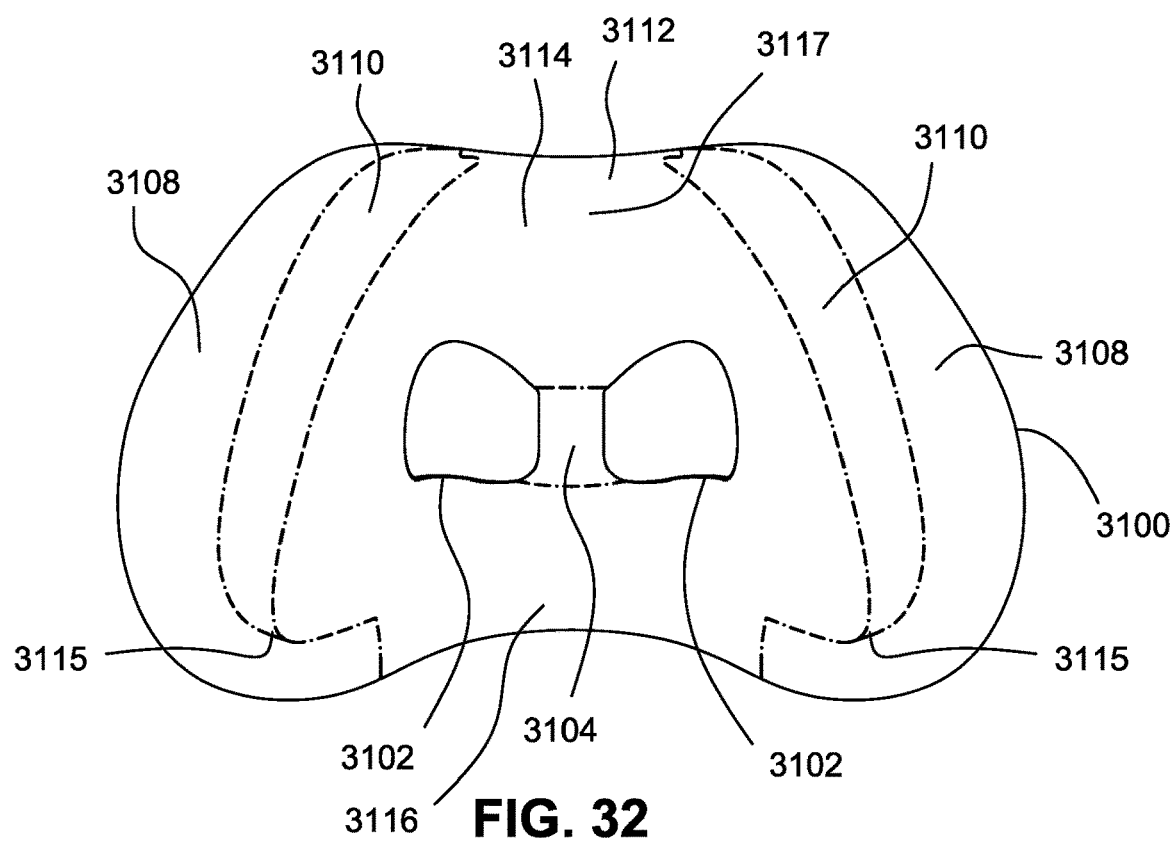

FIG. 32 is a posterior view of a seal-forming structure for a patient interface according to an example of the present technology.

Figure 33:
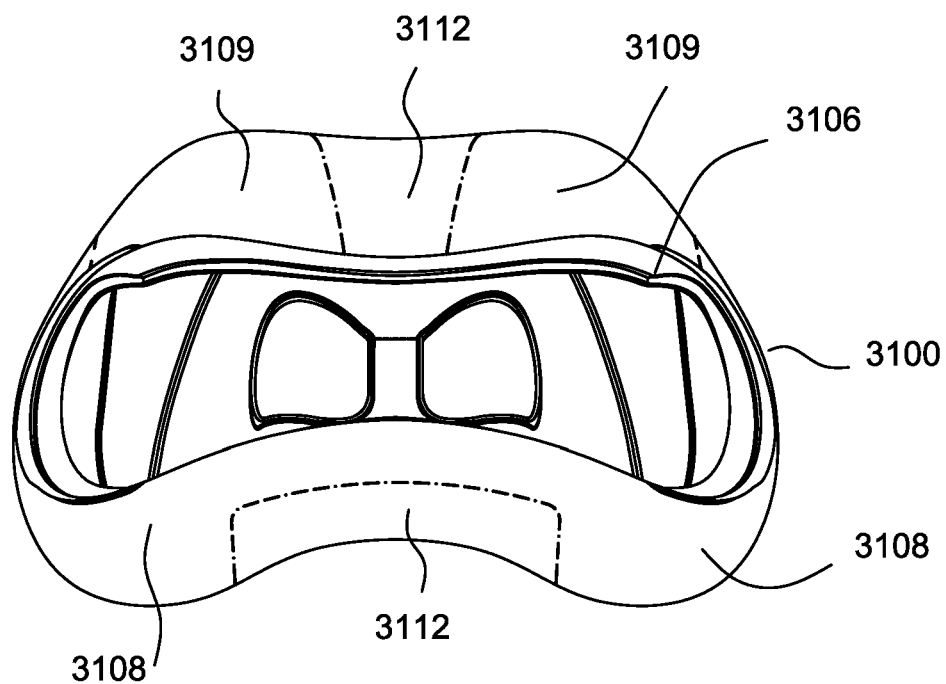

FIG. 33 is an anterior view of a seal-forming structure for a patient interface according to an example of the present technology.

Figure 34:
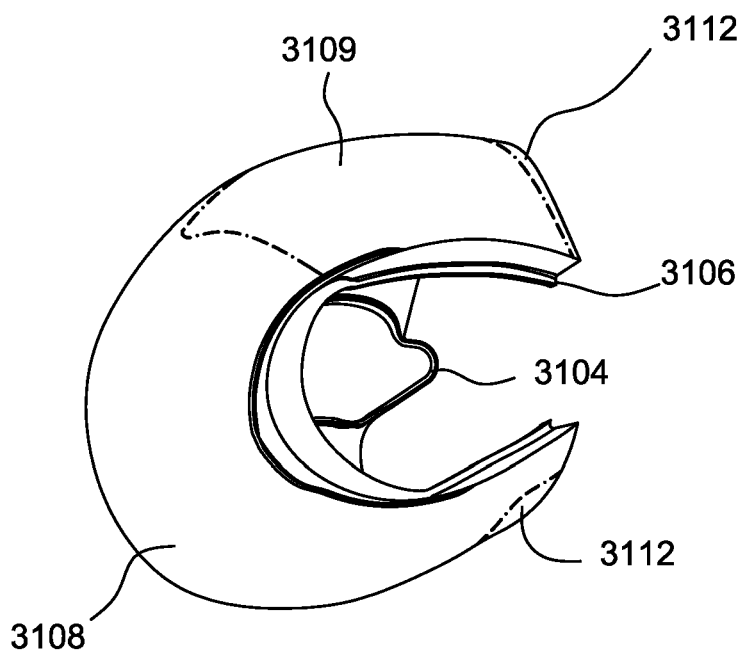

FIG. 34 is a lateral view of a seal-forming structure for a patient interface according to an example of the present technology.

Figure 35:
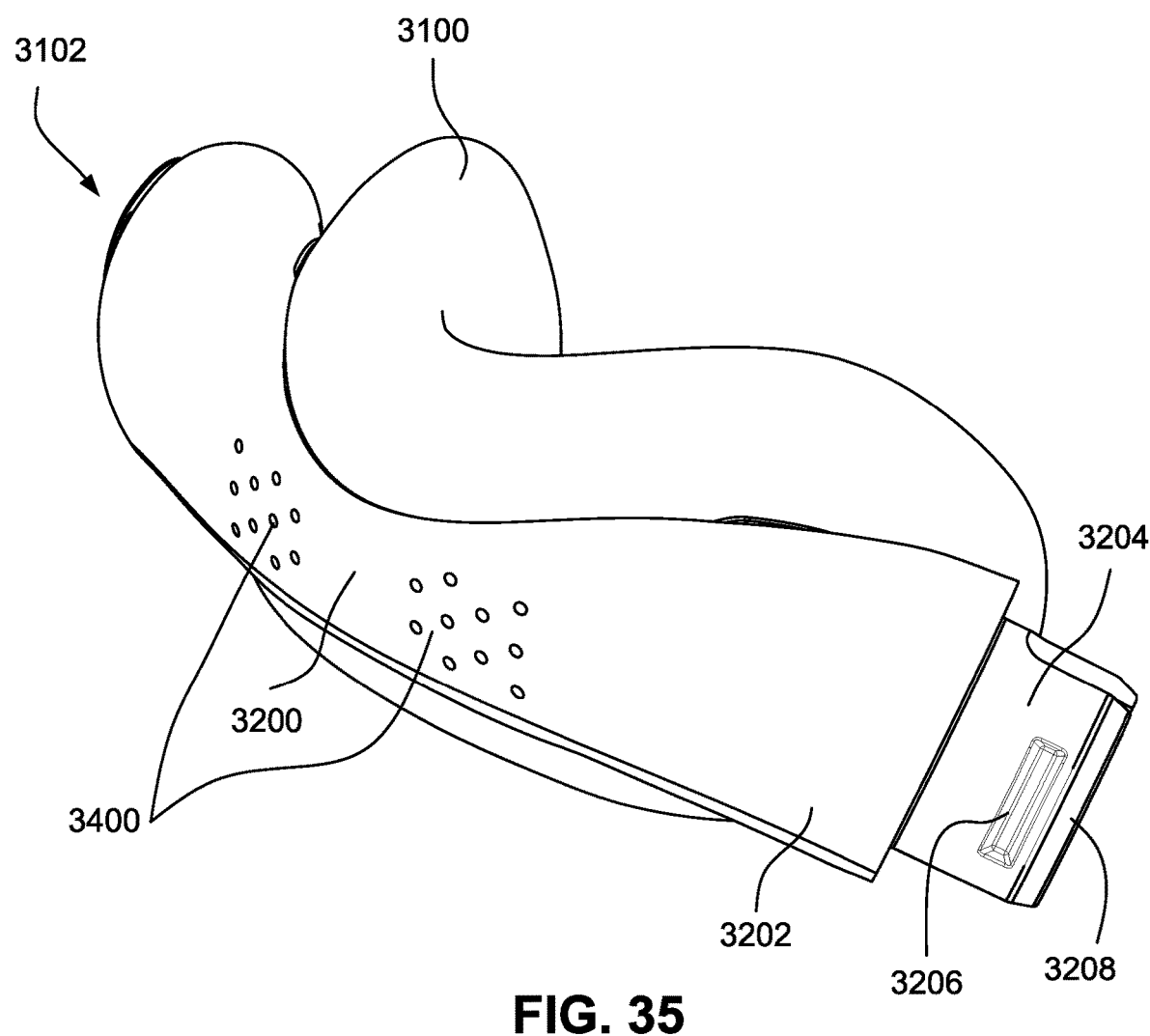

FIG. 35 is an anterolateral view from a superior position of a seal-forming structure and a plenum chamber for a patient interface according to an example of the present technology.

Figure 36:
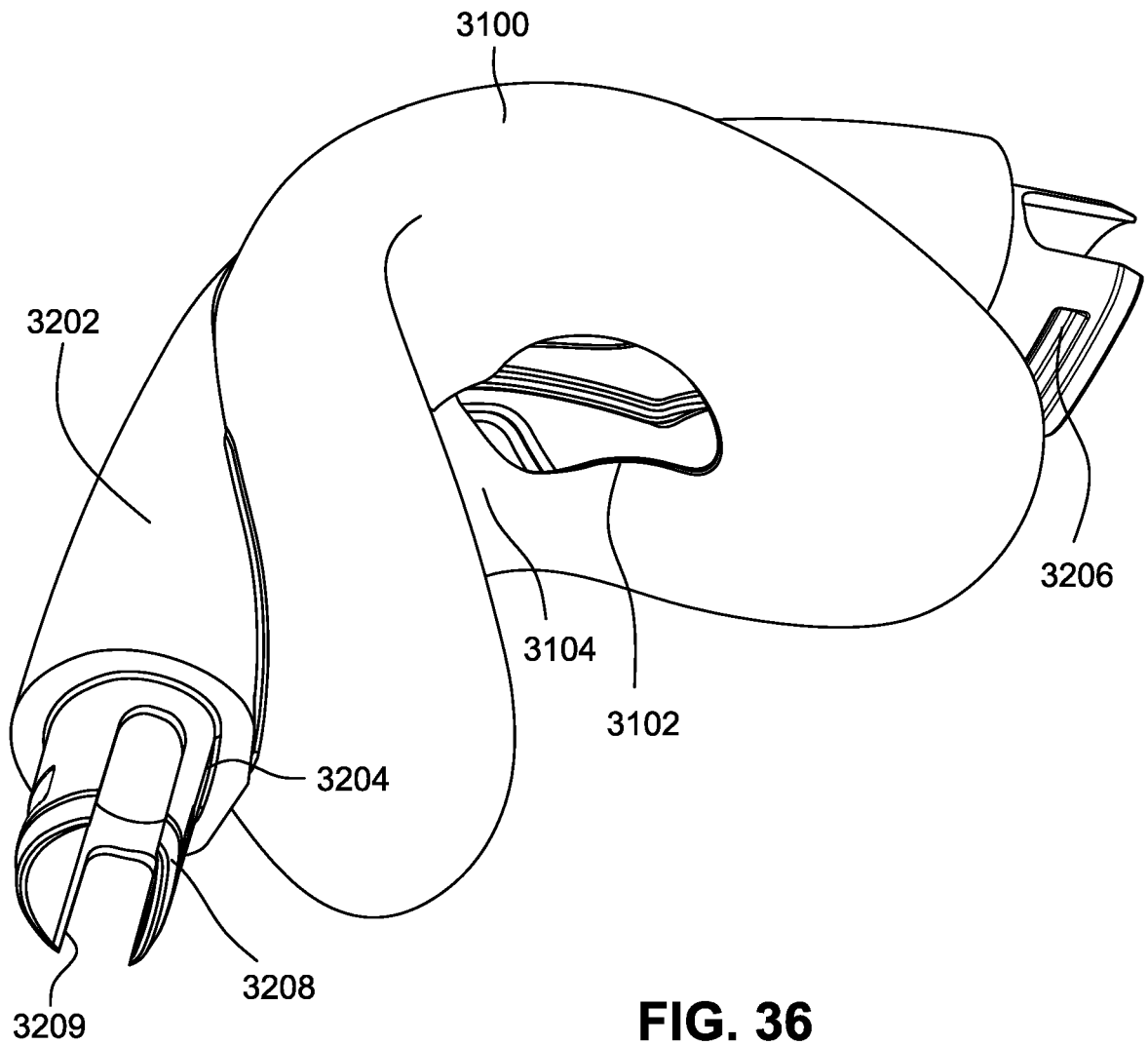

FIG. 36 is a posterolateral view from a superior position of a seal-forming structure and a plenum chamber for a patient interface according to an example of the present technology.

Figure 37:
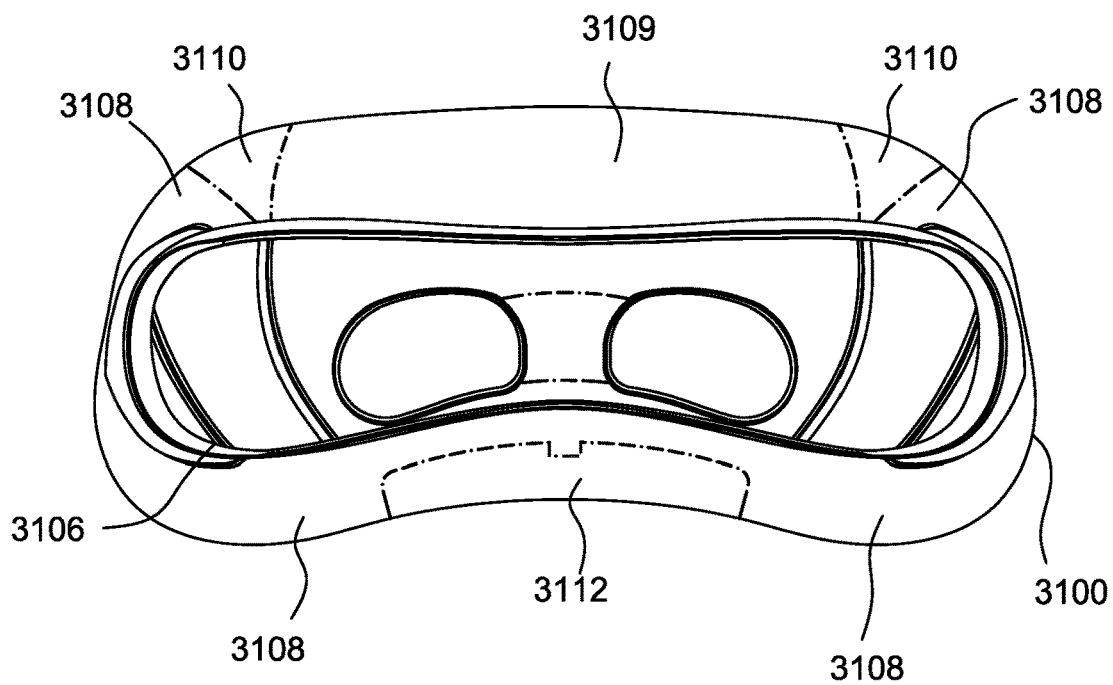

FIG. 37 is an anterior view of a seal-forming structure for a patient interface according to an example of the present technology.

Figure 38:
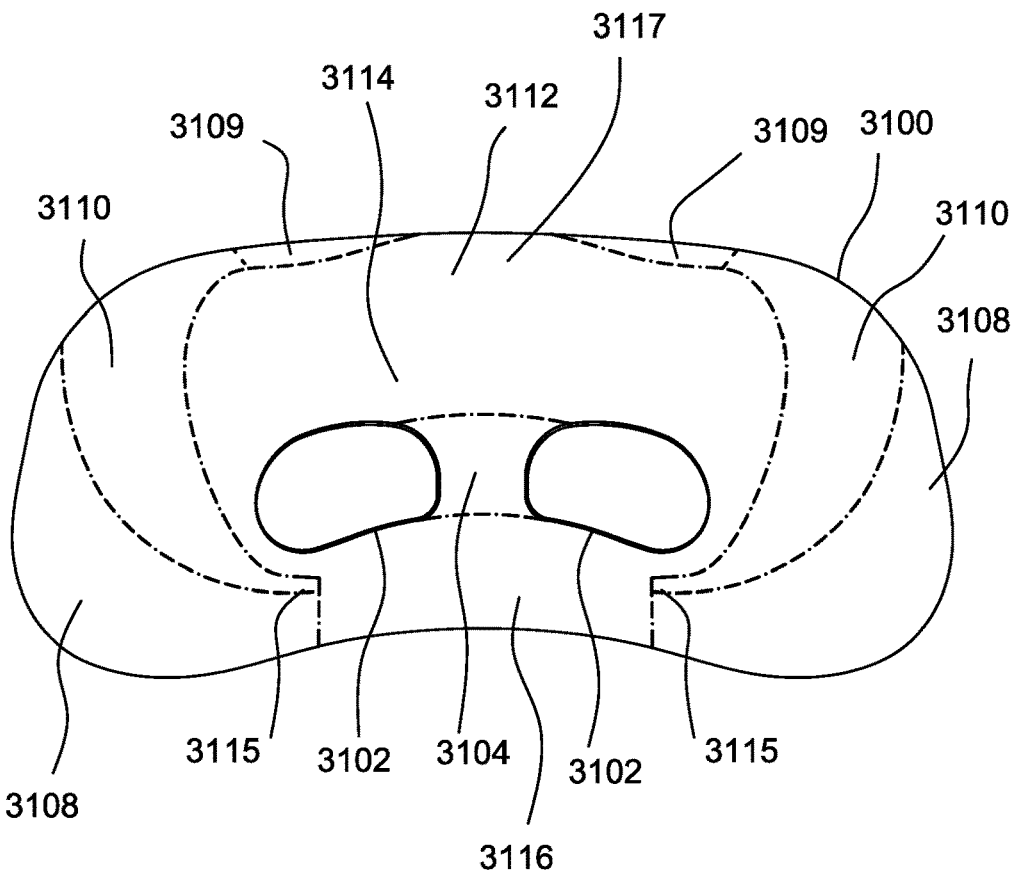

FIG. 38 is a posterior view of a seal-forming structure for a patient interface according to an example of the present technology.

Figure 39:
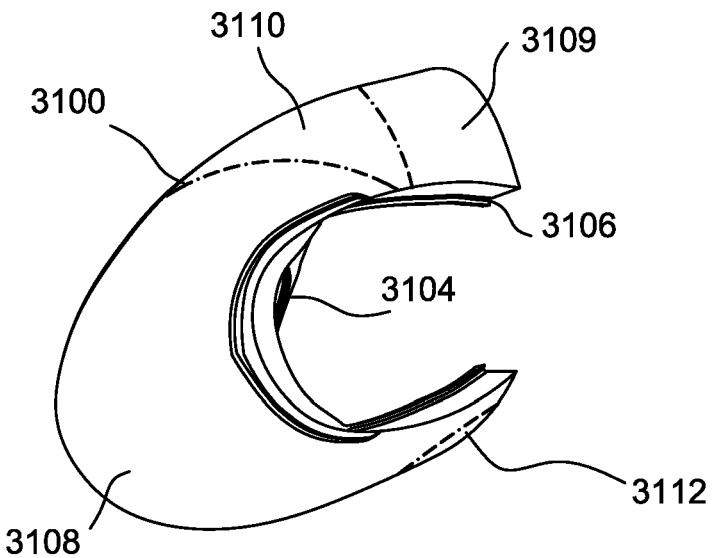

FIG. 39 is a lateral view of a seal-forming structure for a patient interface according to an example of the present technology.

Figure 40:
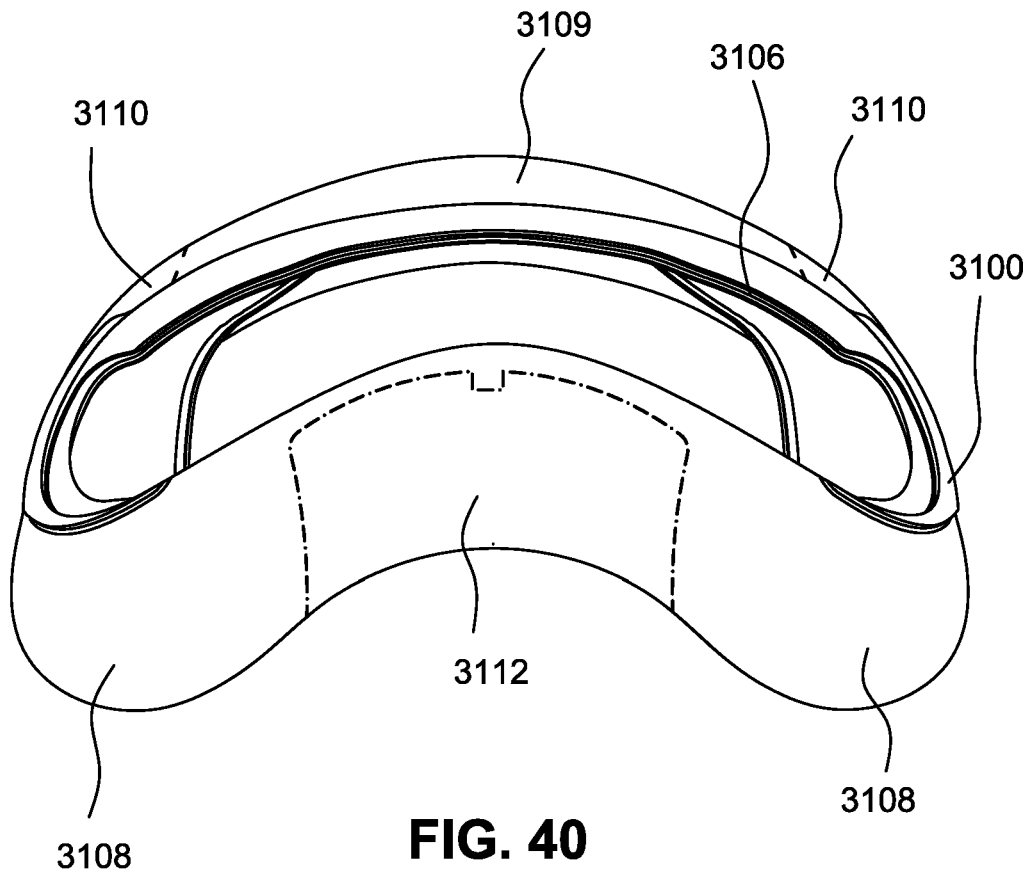

FIG. 40 is an inferior view of a seal-forming structure for a patient interface according to an example of the present technology.

Figure 41:
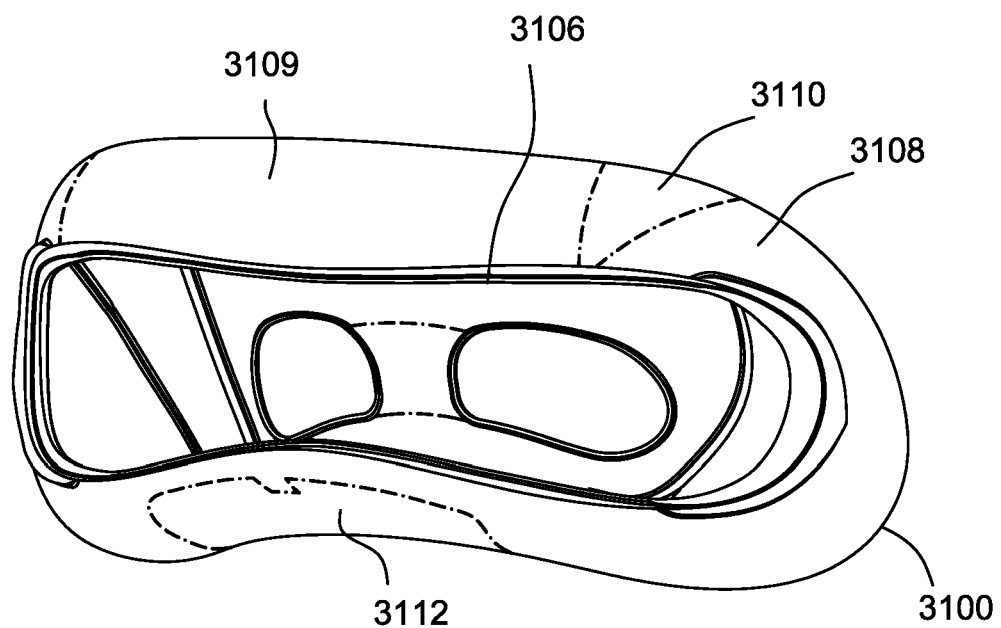

FIG. 41 is an anterolateral view of a seal-forming structure for a patient interface according to an example of the present technology.

Figure 42:
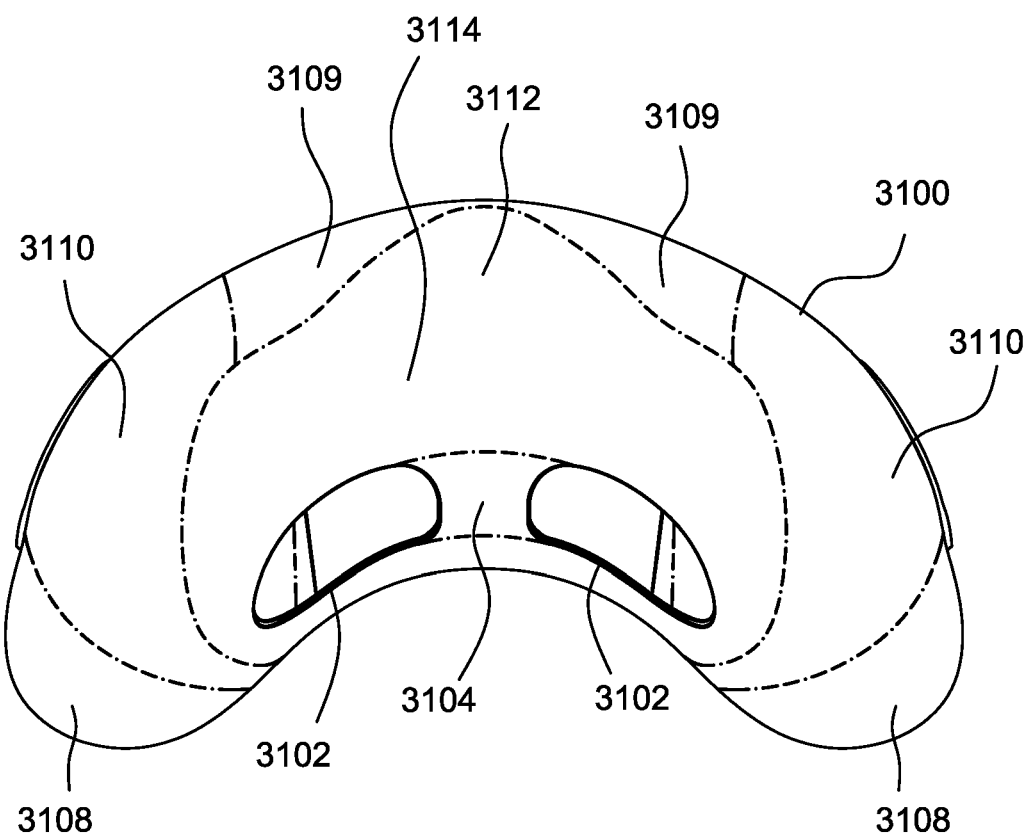

FIG. 42 is a superior view of a seal-forming structure for a patient interface according to an example of the present technology.

Figure 43:
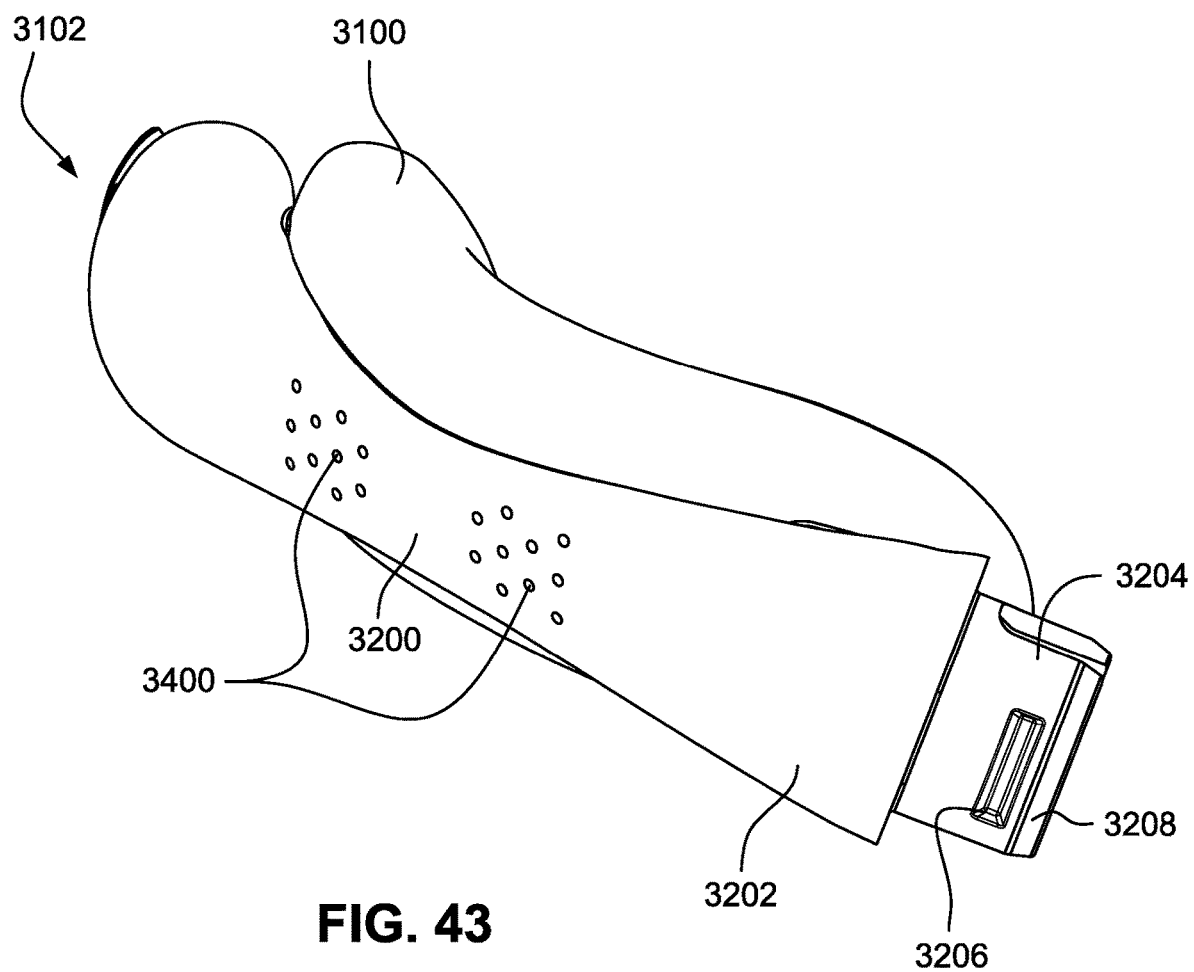

FIG. 43 is an anterolateral view from a superior position of a seal-forming structure and a plenum chamber for a patient interface according to an example of the present technology.

Figure 44:
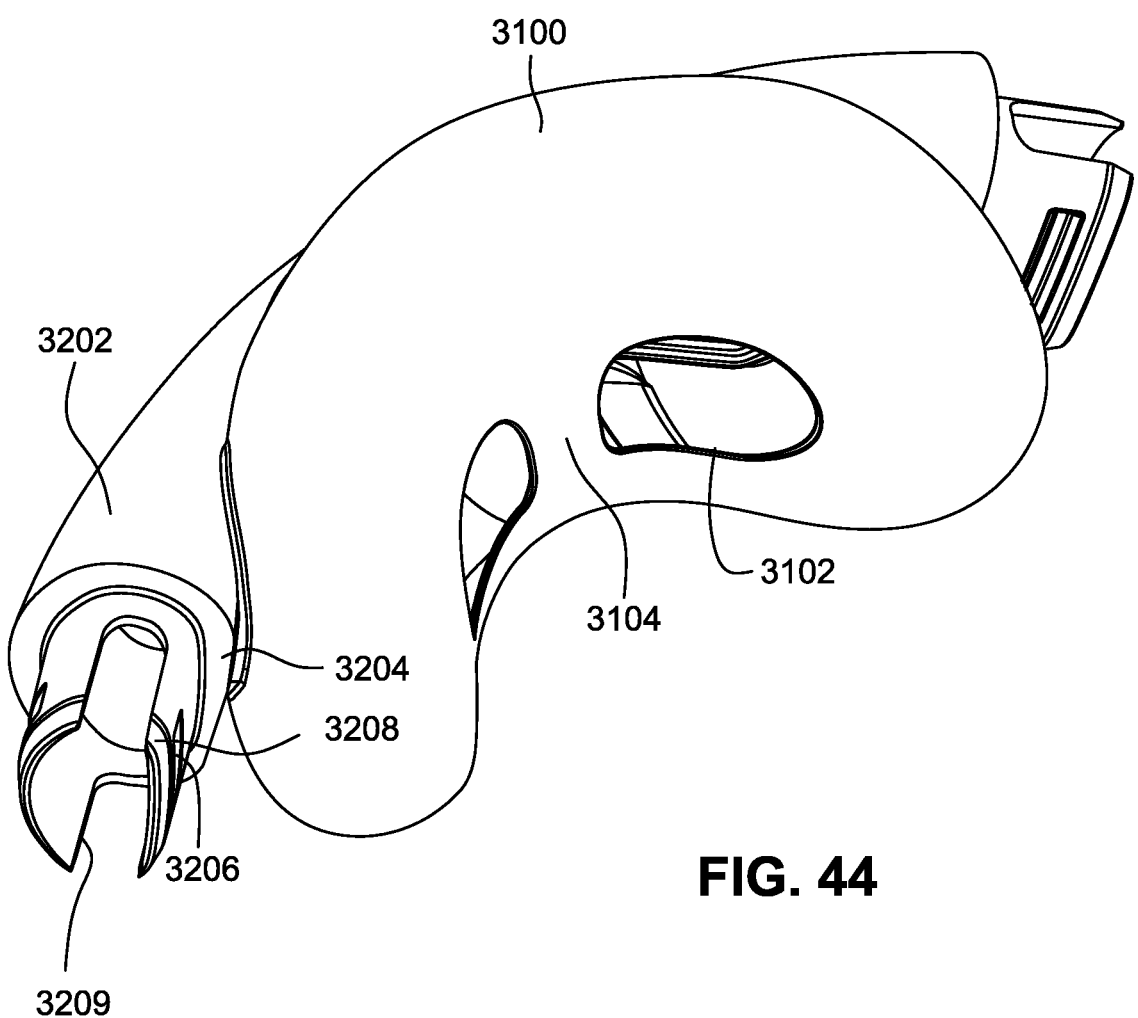

FIG. 44 is a posterolateral view from a superior position of a seal-forming structure and a plenum chamber for a patient interface according to an example of the present technology.

Figure 45:
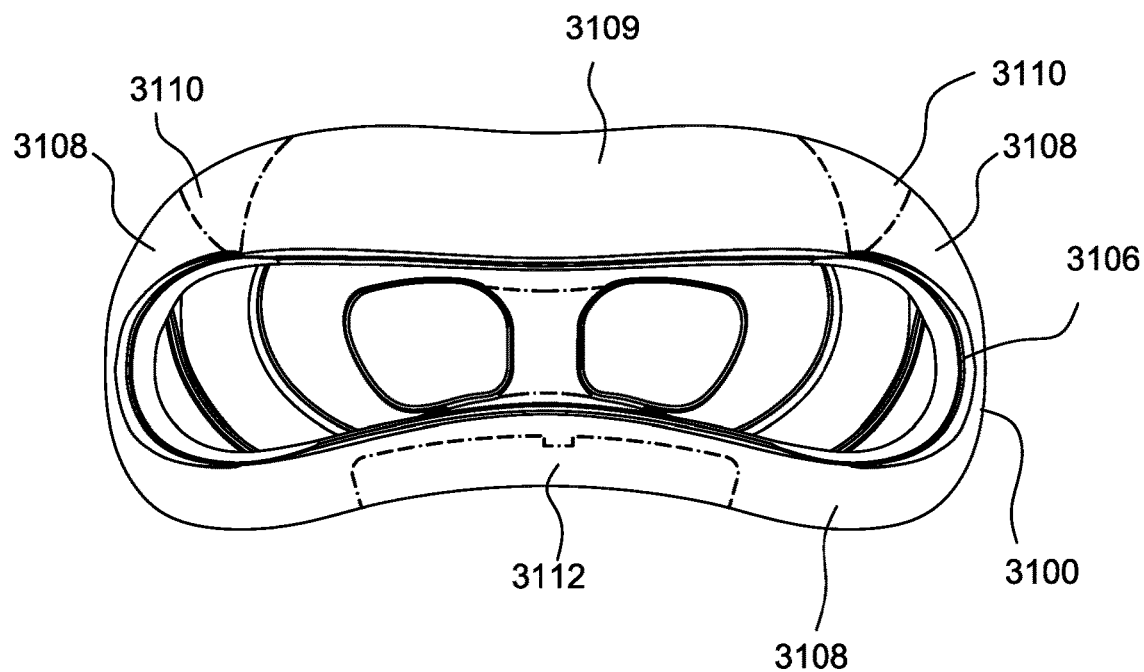

FIG. 45 is an anterior view of a seal-forming structure for a patient interface according to an example of the present technology.

Figure 46:
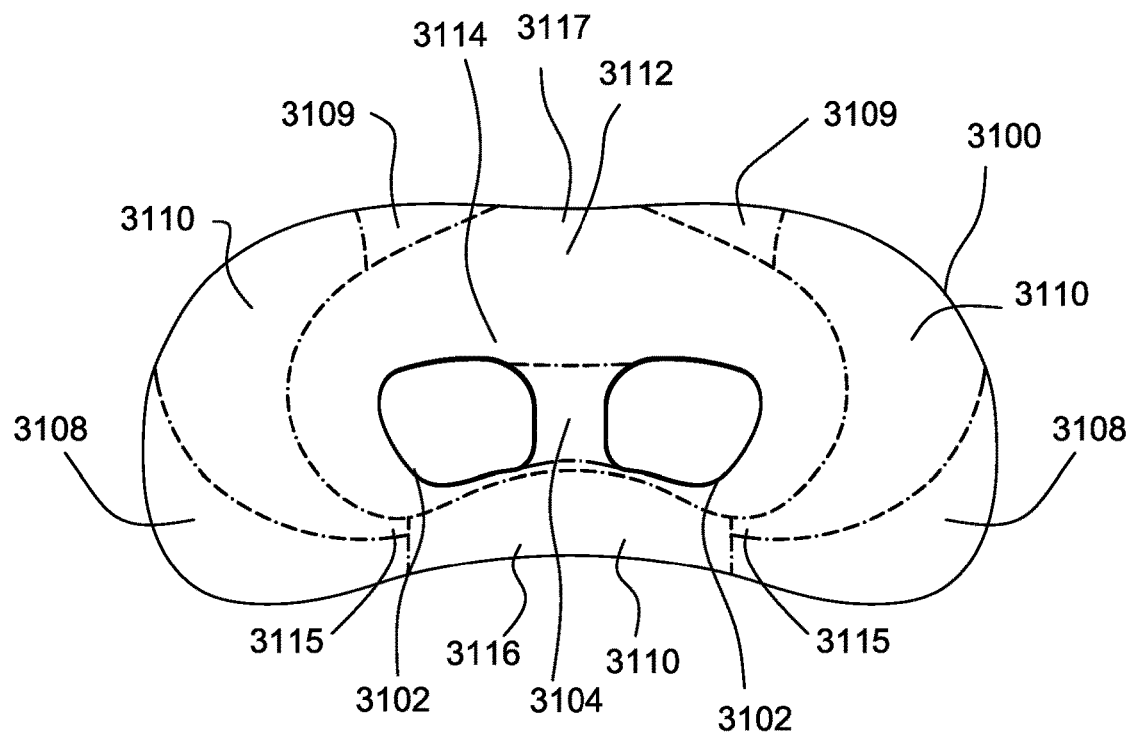

FIG. 46 is a posterior view of a seal-forming structure for a patient interface according to an example of the present technology.

Figure 47:
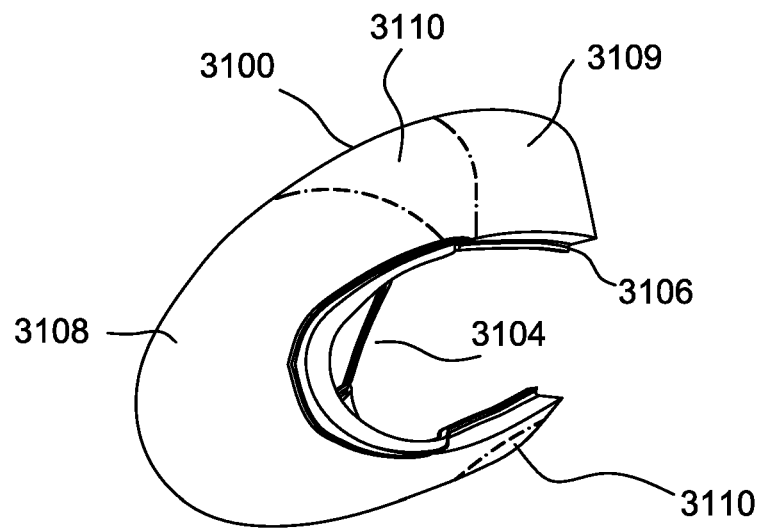

FIG. 47 is a lateral view of a seal-forming structure for a patient interface according to an example of the present technology.

Figure 48:
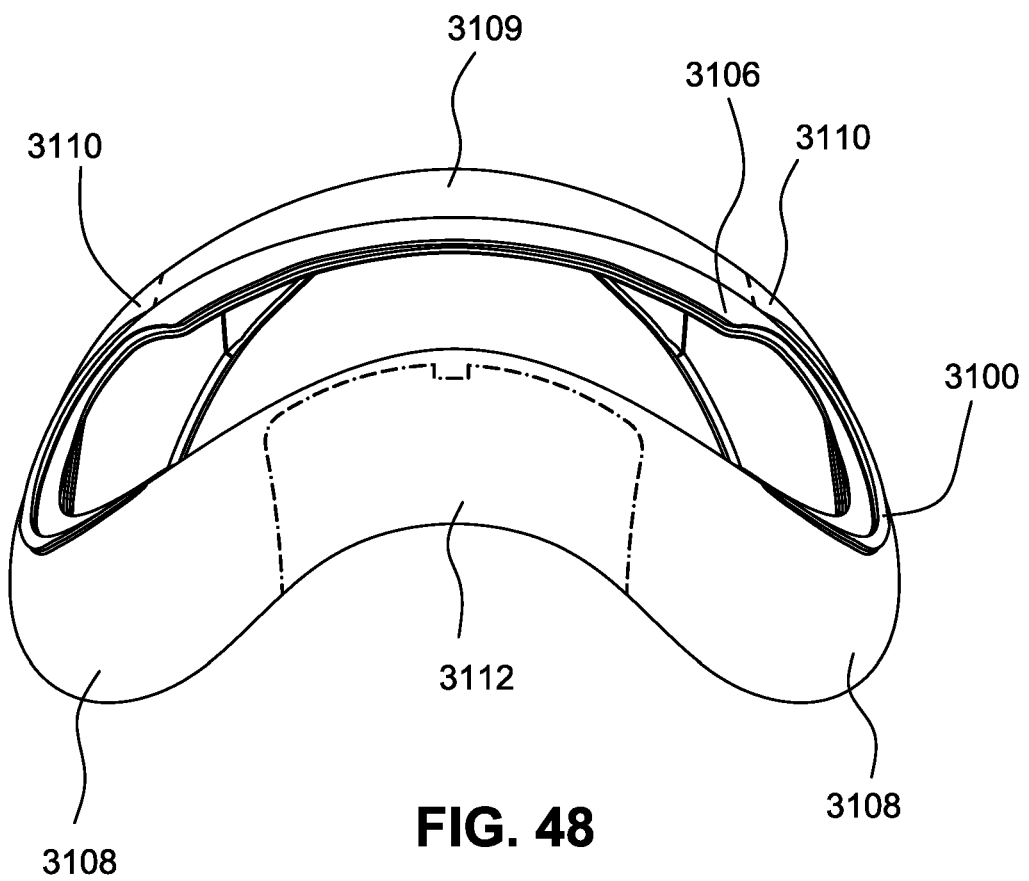

FIG. 48 is an inferior view of a seal-forming structure for a patient interface according to an example of the present technology.

Figure 49:
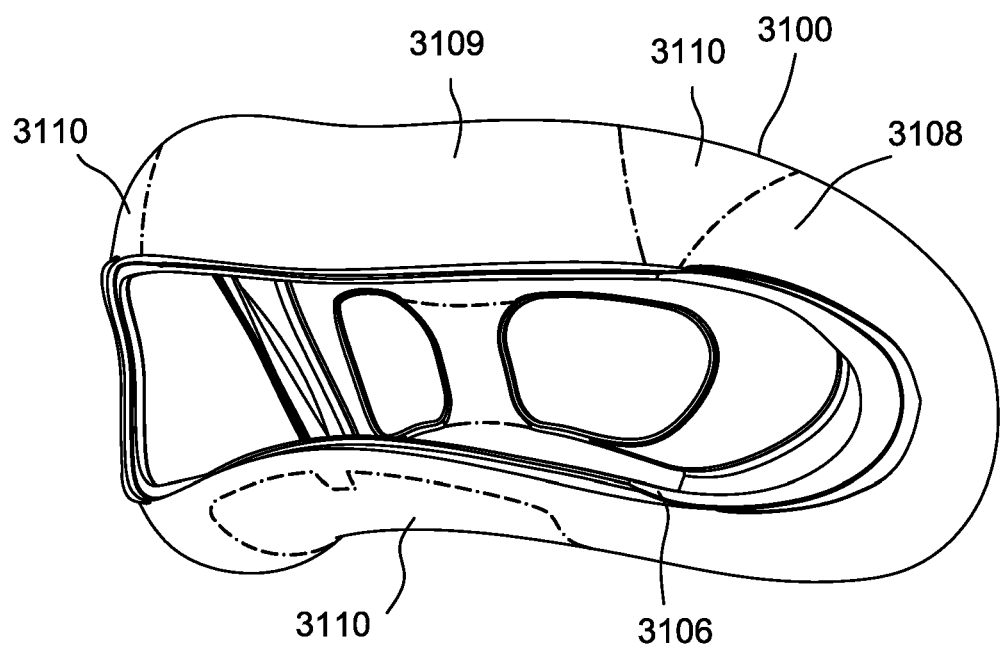

FIG. 49 is an anterolateral view of a seal-forming structure for a patient interface according to an example of the present technology.

Figure 50:
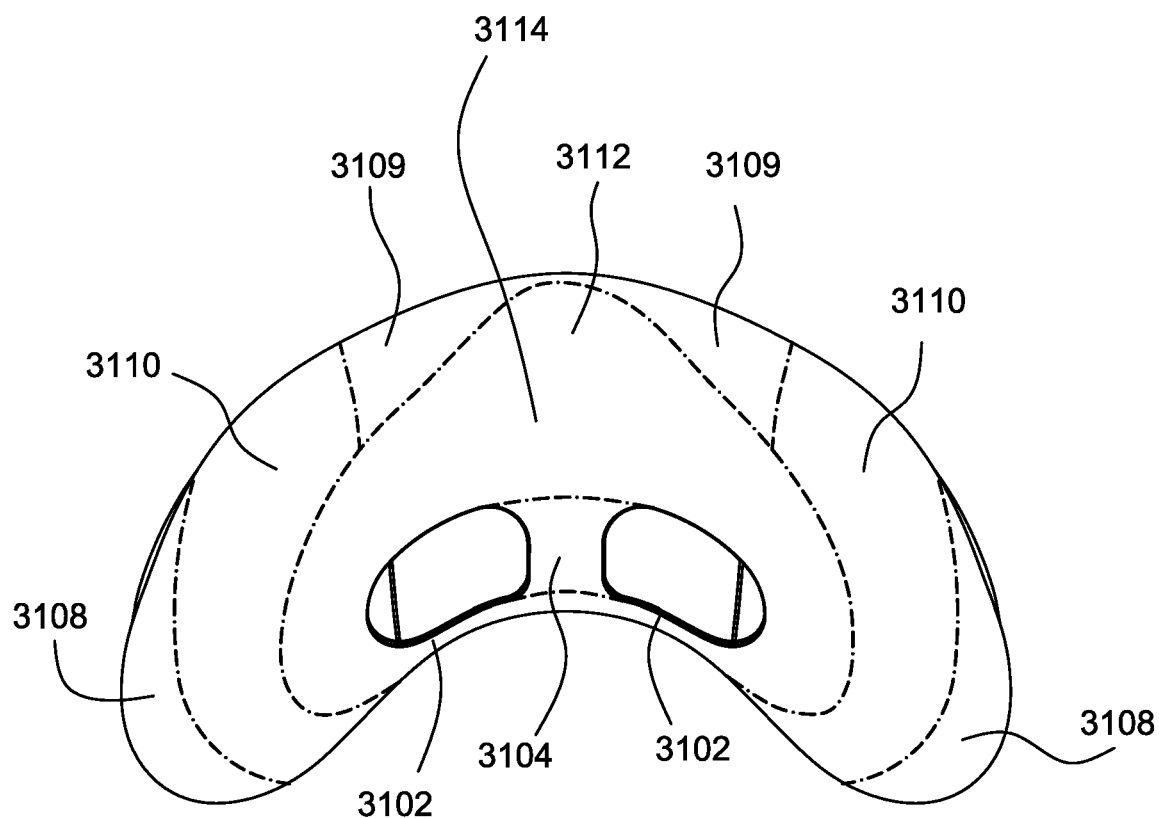

FIG. 50 is a superior view of a seal-forming structure for a patient interface according to an example of the present technology.

Figure 51:
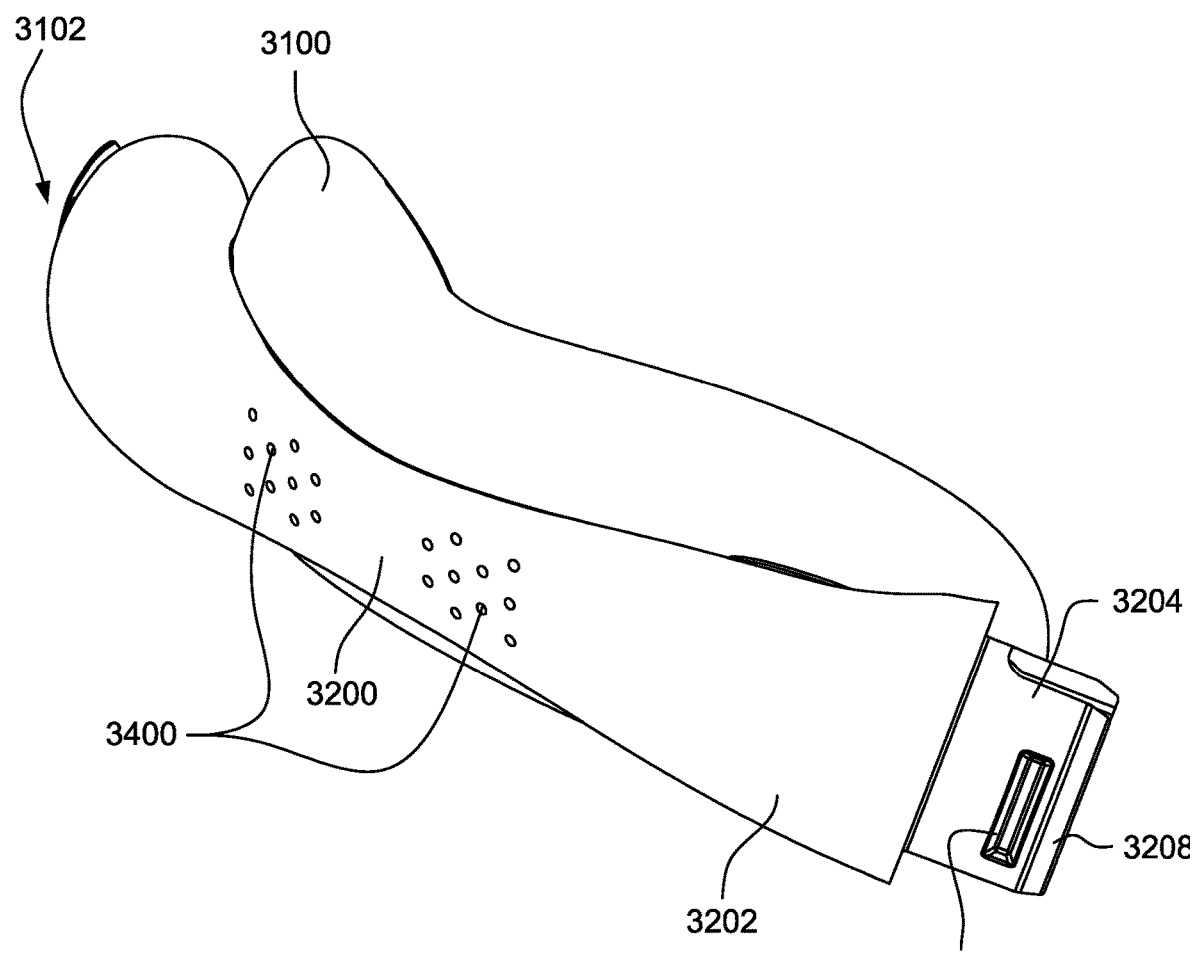

FIG. 51 is an anterolateral view from a superior position of a seal-forming structure and a plenum chamber for a patient interface according to an example of the present technology.

Figure 52:
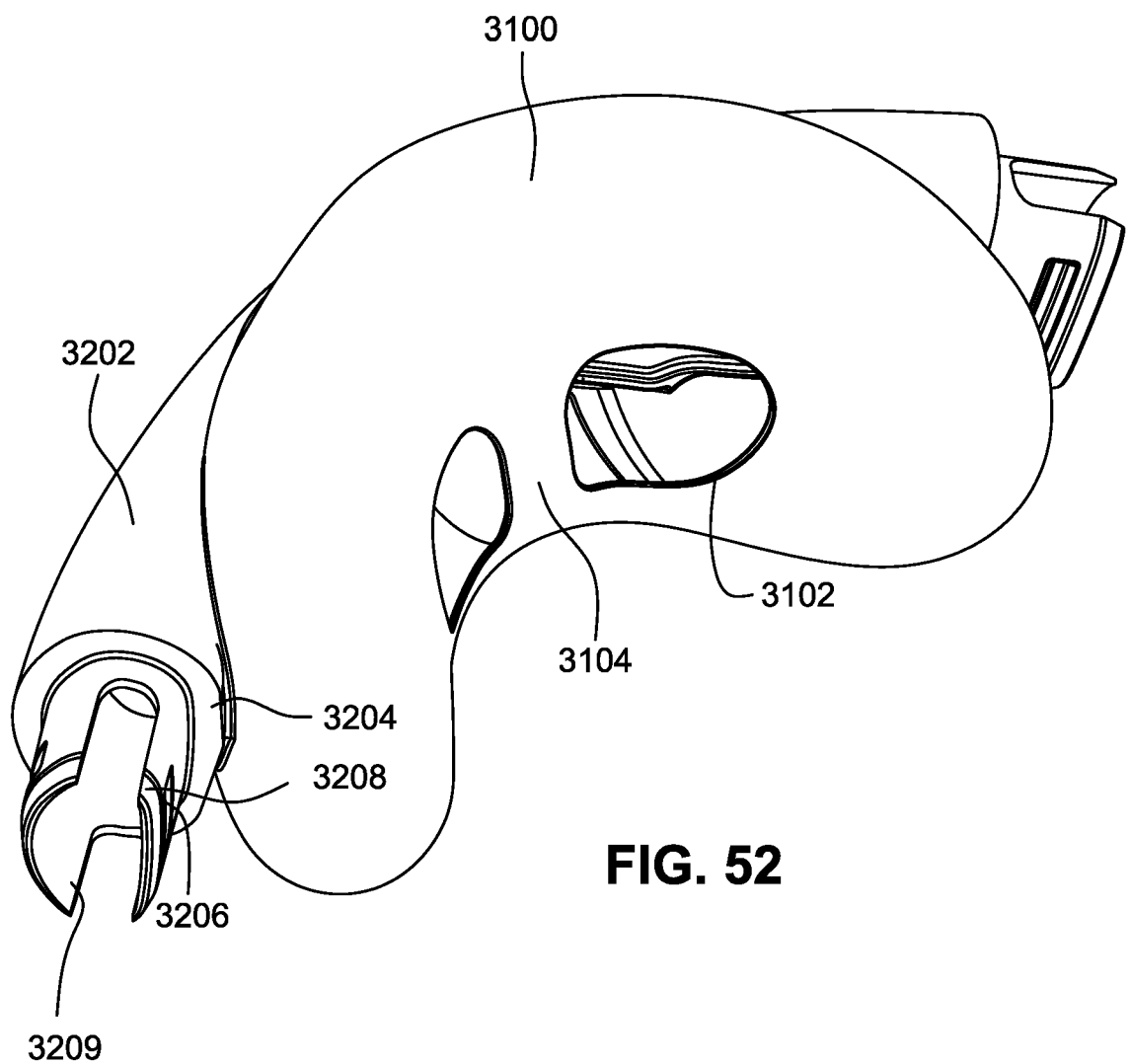

FIG. 52 is a posterolateral view from a superior position of a seal-forming structure and a plenum chamber for a patient interface according to an example of the present technology.

Figure 53:
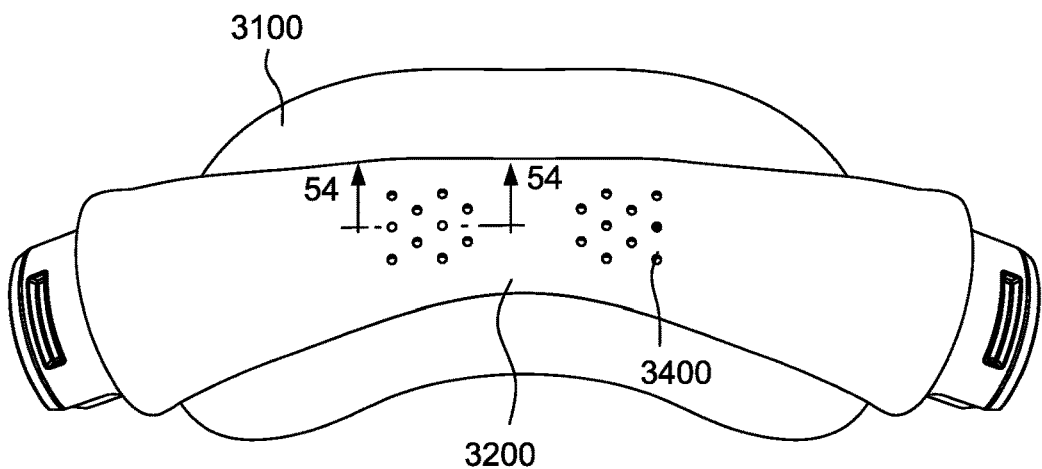

FIG. 53 is an anterior reference view for a cross-section taken through line 54-54 of a seal-forming structure and a plenum chamber for a patient interface according to an example of the present technology.

Figure 54:
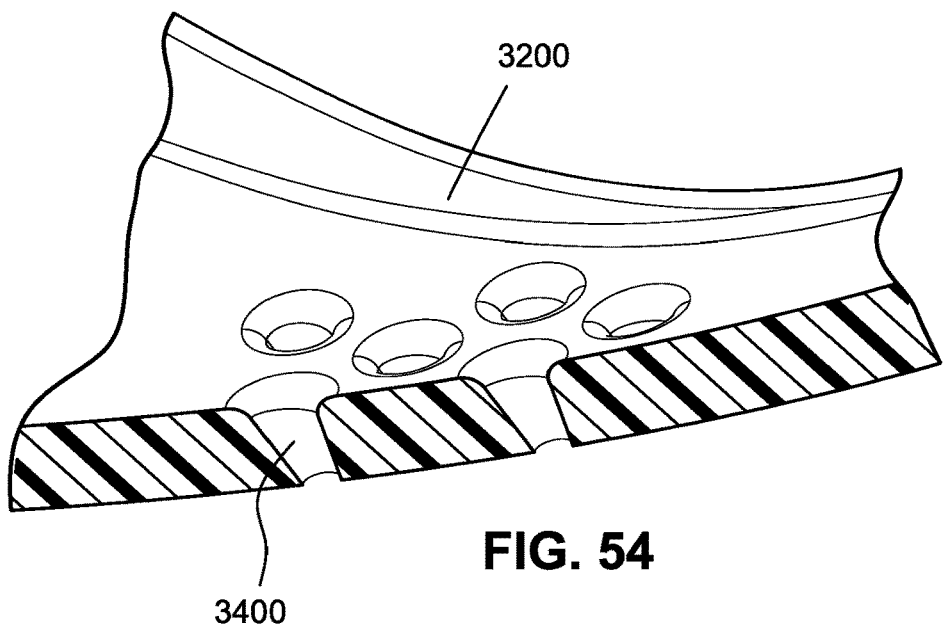

FIG. 54 is a detailed, cross-sectional view of a plenum chamber according to an example of the present technology taken through line 54-54 of FIG. 53.

Figure 55:
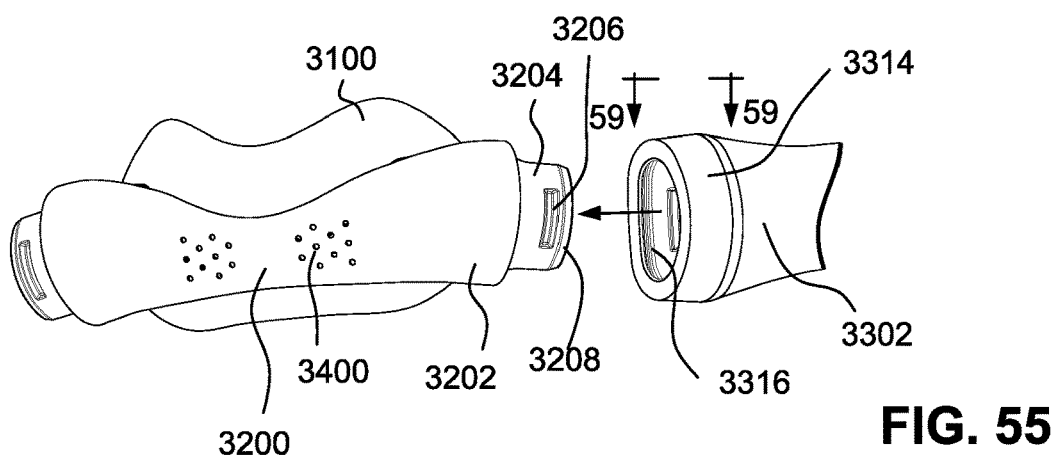

FIG. 55 is an exploded, anterior view of a seal-forming structure and a plenum chamber disconnected from a conduit for a patient interface according to an example of the present technology.

Figure 56:
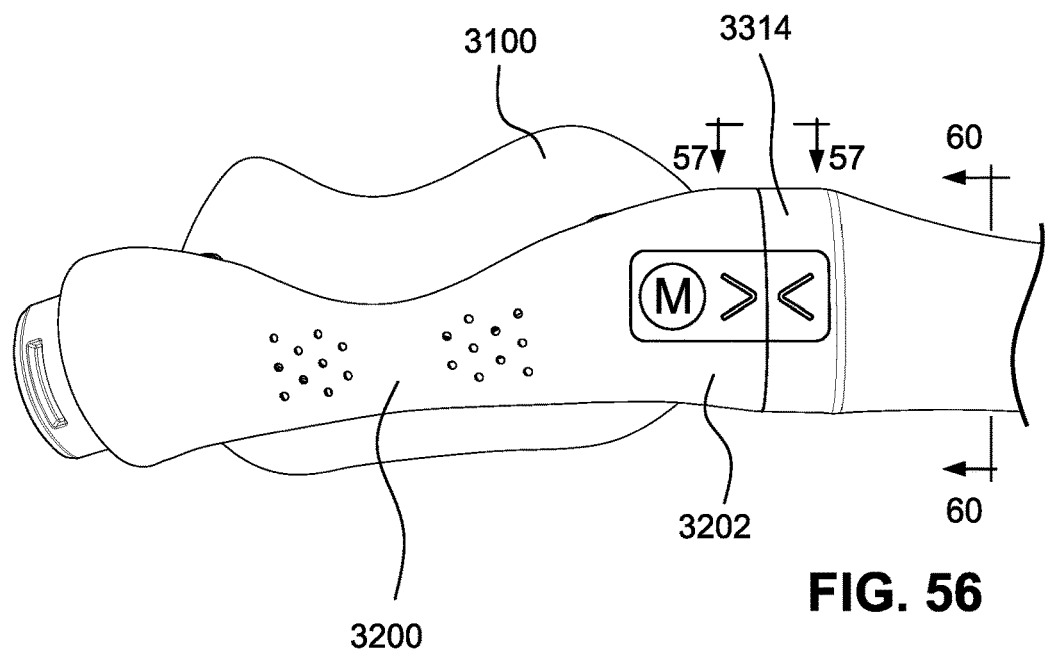

FIG. 56 is an anterior reference view for cross-sections taken through lines 57-57 and 60-60 of a seal-forming structure and a plenum chamber connected to a conduit for a patient interface according to an example of the present technology.

Figure 57:
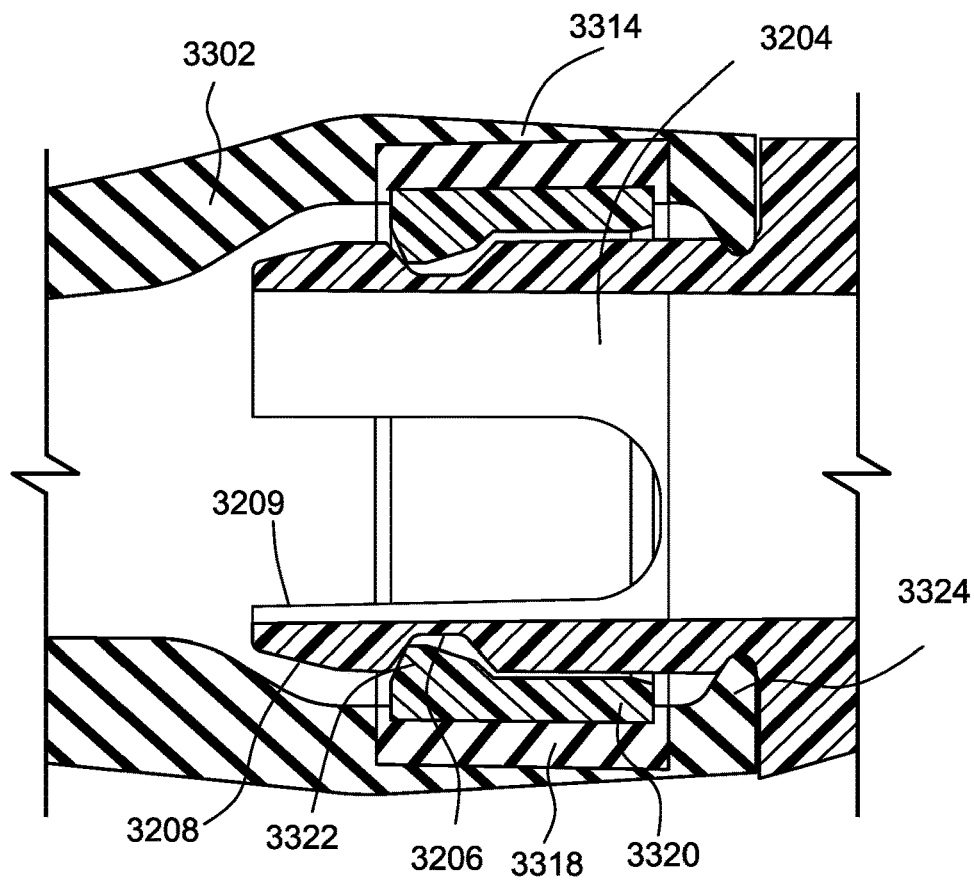

FIG. 57 is a detailed, cross-sectional view of a plenum chamber connector and a conduit connected together according to an example of the present technology taken through line 57-57 of FIG. 56.

Figure 58:
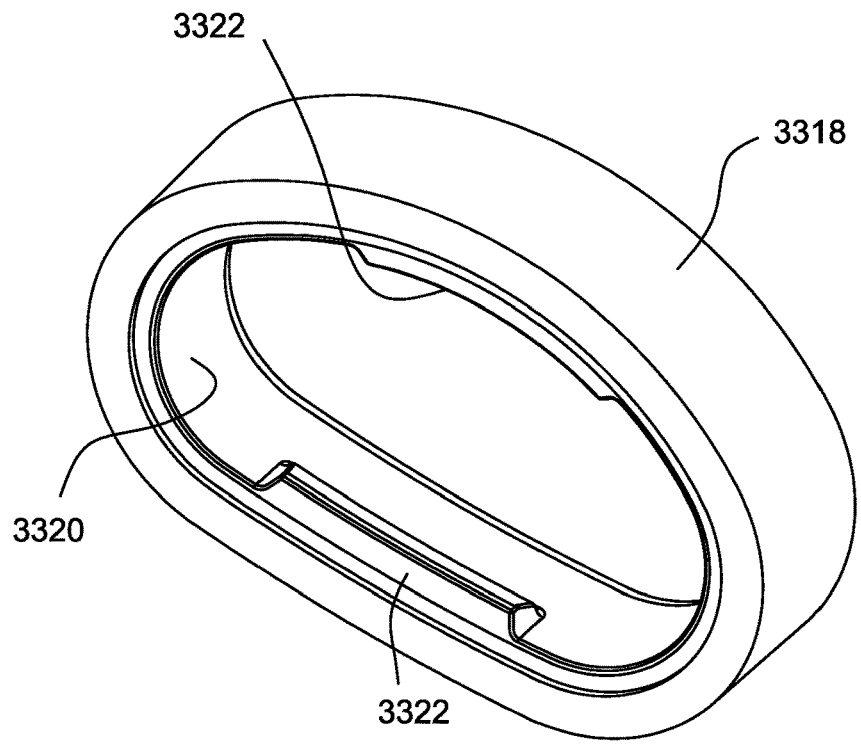

FIG. 58 is perspective view of a clip and a clip overmold of a conduit according to an example of the present technology.

Figure 59:
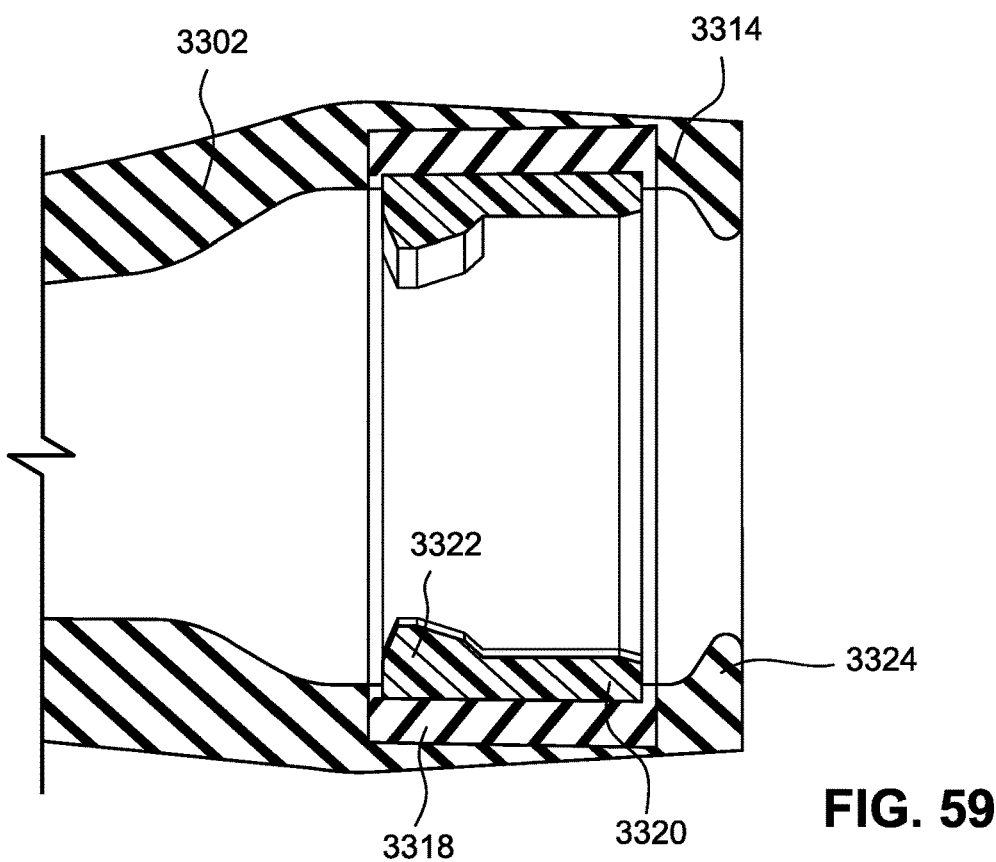

FIG. 59 is a cross-sectional view of a conduit from FIG. 57.

Figure 60:
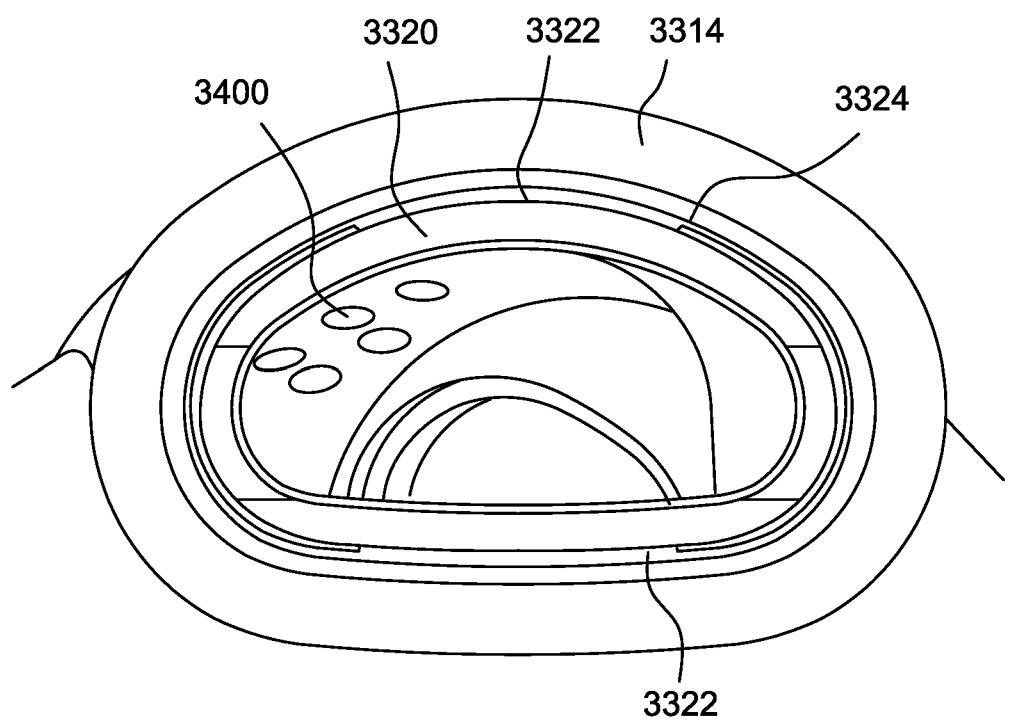

FIG. 60 is a cross-sectional view through a conduit and into a plenum chamber taken through line 60-60 of FIG. 56.

Figure 61:
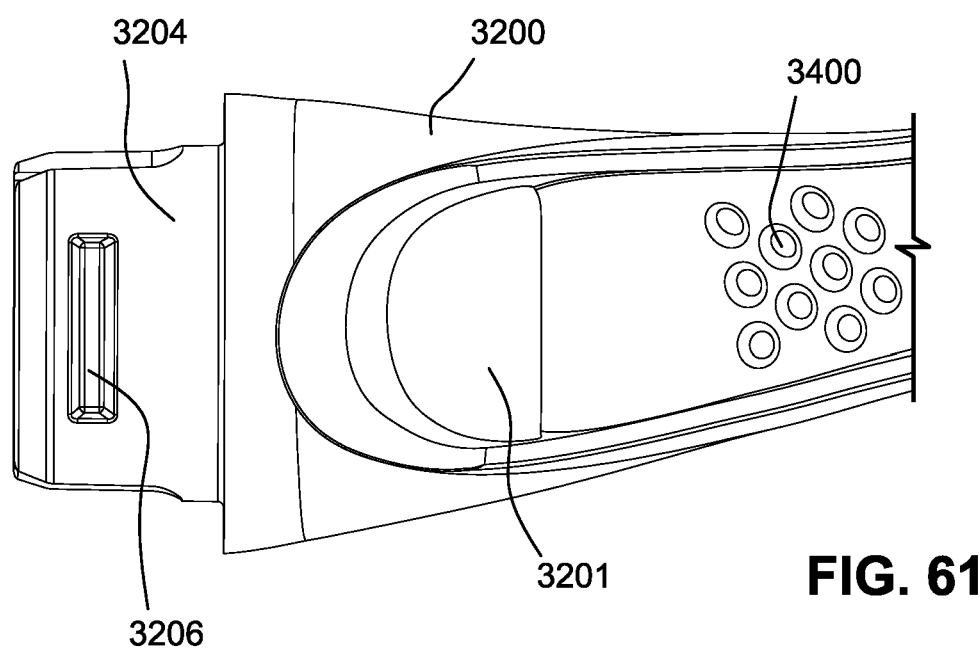

FIG. 61 is posterior view of a plenum chamber and a plenum chamber connector according to an example of the present technology.

Figure 62:
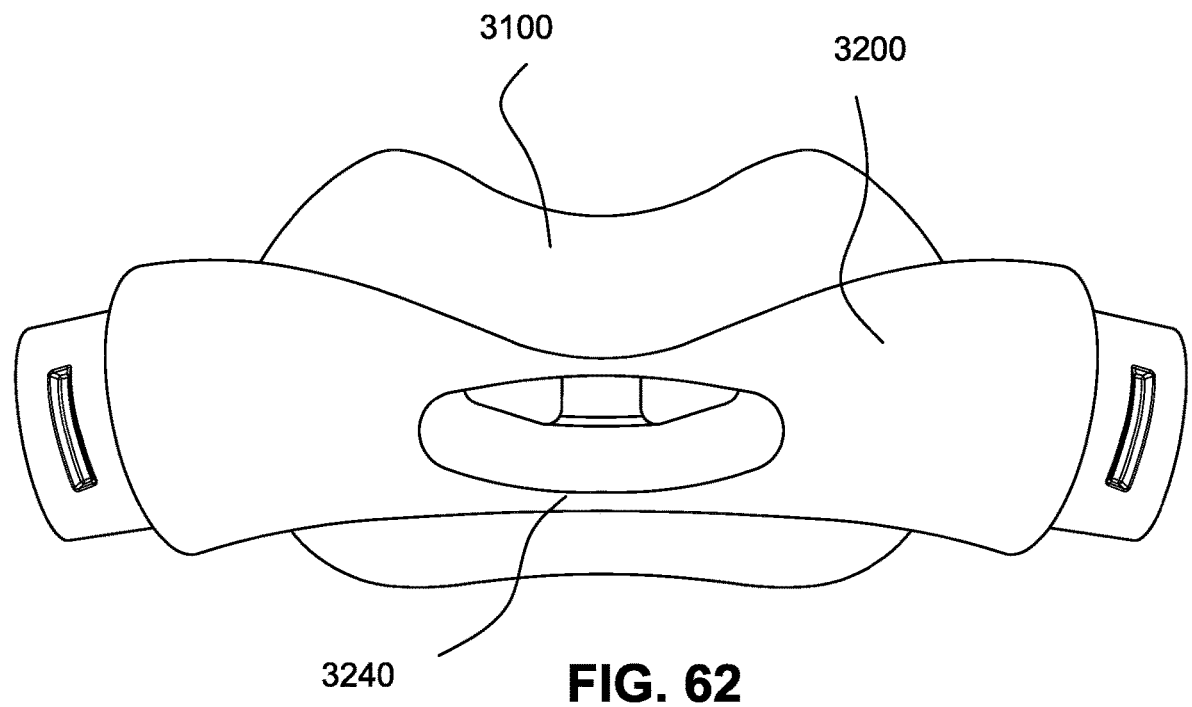

FIG. 62 is an anterior view of a seal-forming structure and a plenum chamber for a patient interface without a vent insert in a vent insert opening according to an example of the present technology.

Figure 63:
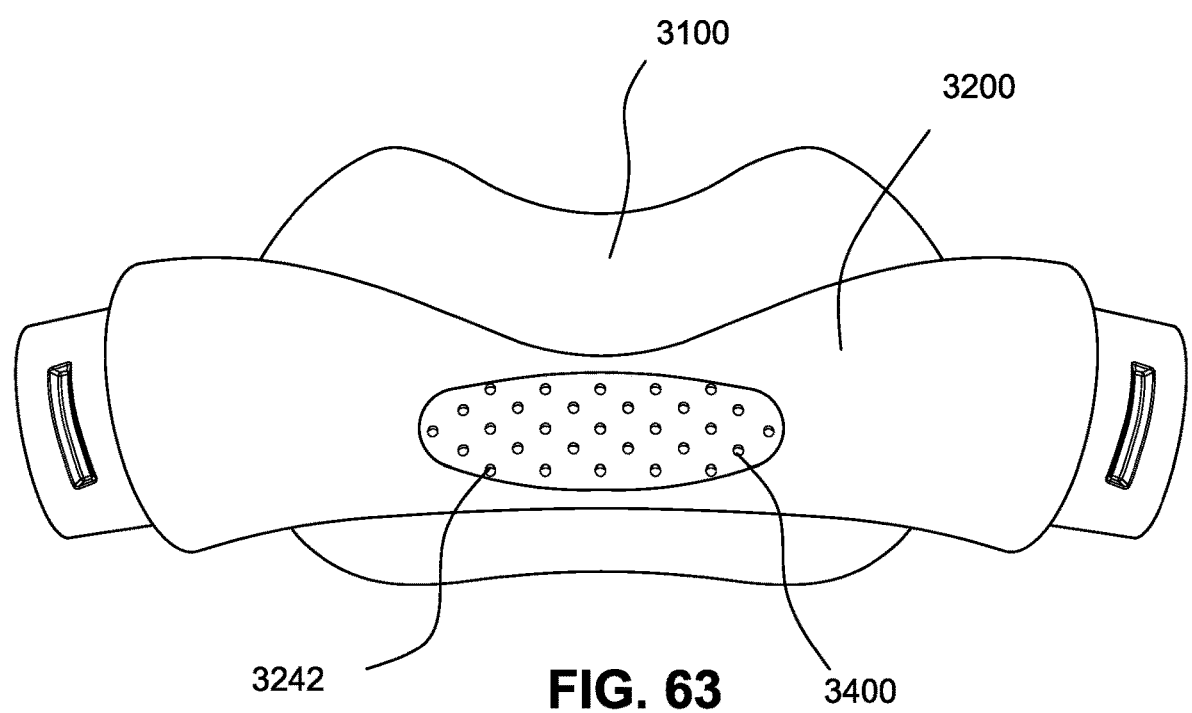

FIG. 63 is an anterior view of a seal-forming structure and a plenum chamber for a patient interface with a vent insert in a vent insert opening according to an example of the present technology.

Figure 64:
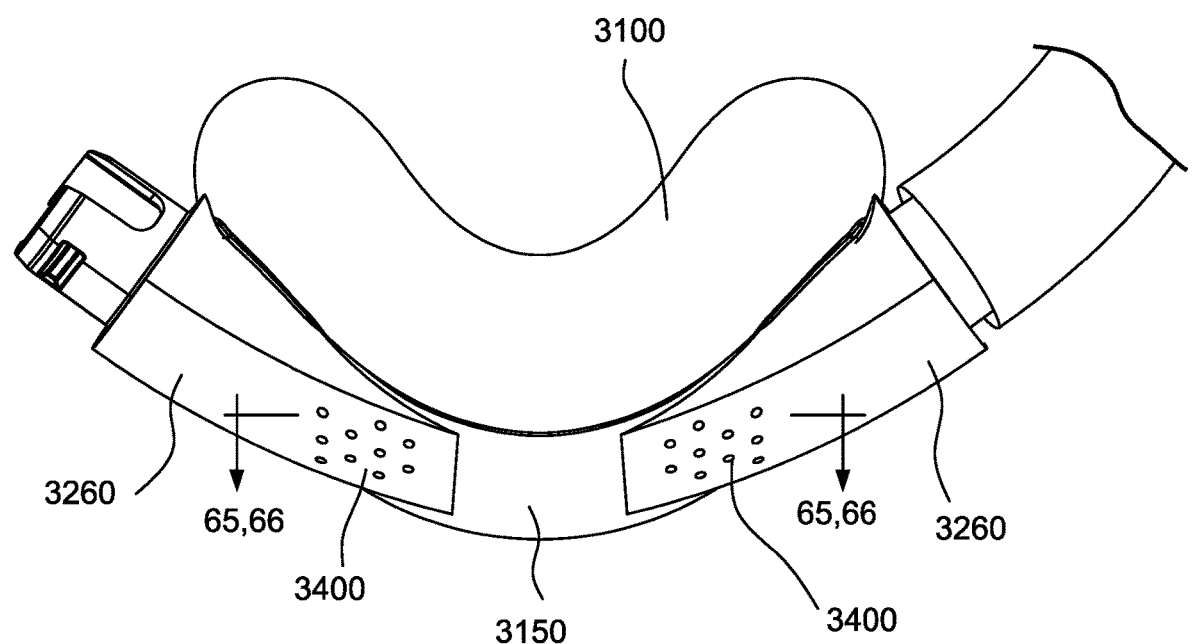

FIG. 64 is a cross-sectional view through a plenum chamber of a patient interface according to an example of the present technology.

Figure 65:
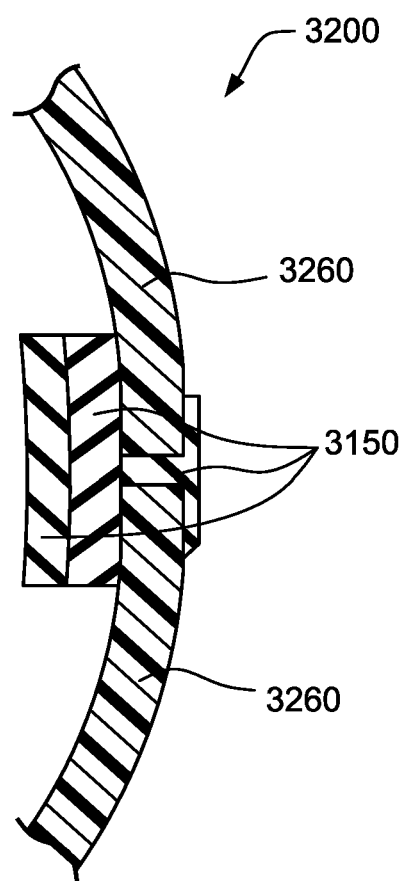

FIG. 65 is a cross-sectional view through a plenum chamber of a patient interface according to an example of the present technology.

Figure 66:
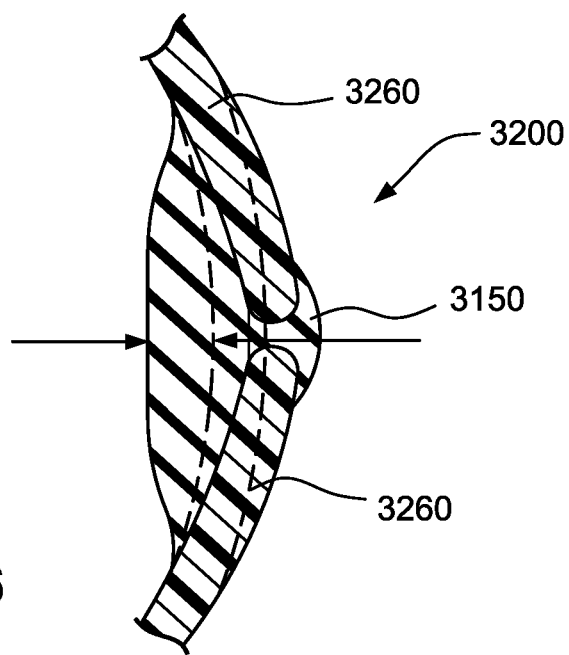

FIG. 66 is a superior view of a patient interface according to an example of the present technology.

Figure 67:
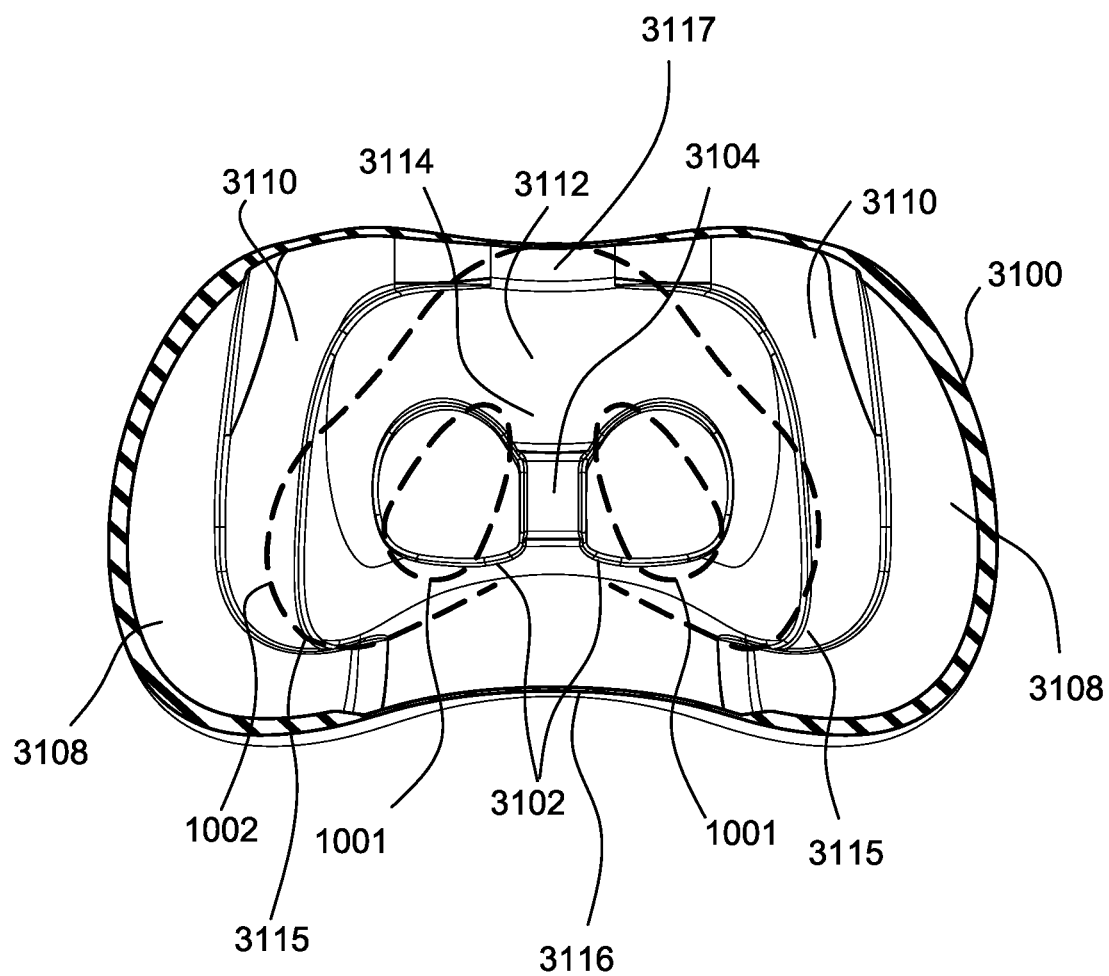

FIG. 67 is a cross-sectional view showing the interior of a seal-forming structure according to an example of the present technology depicted in FIG. 16.

Figure 68:
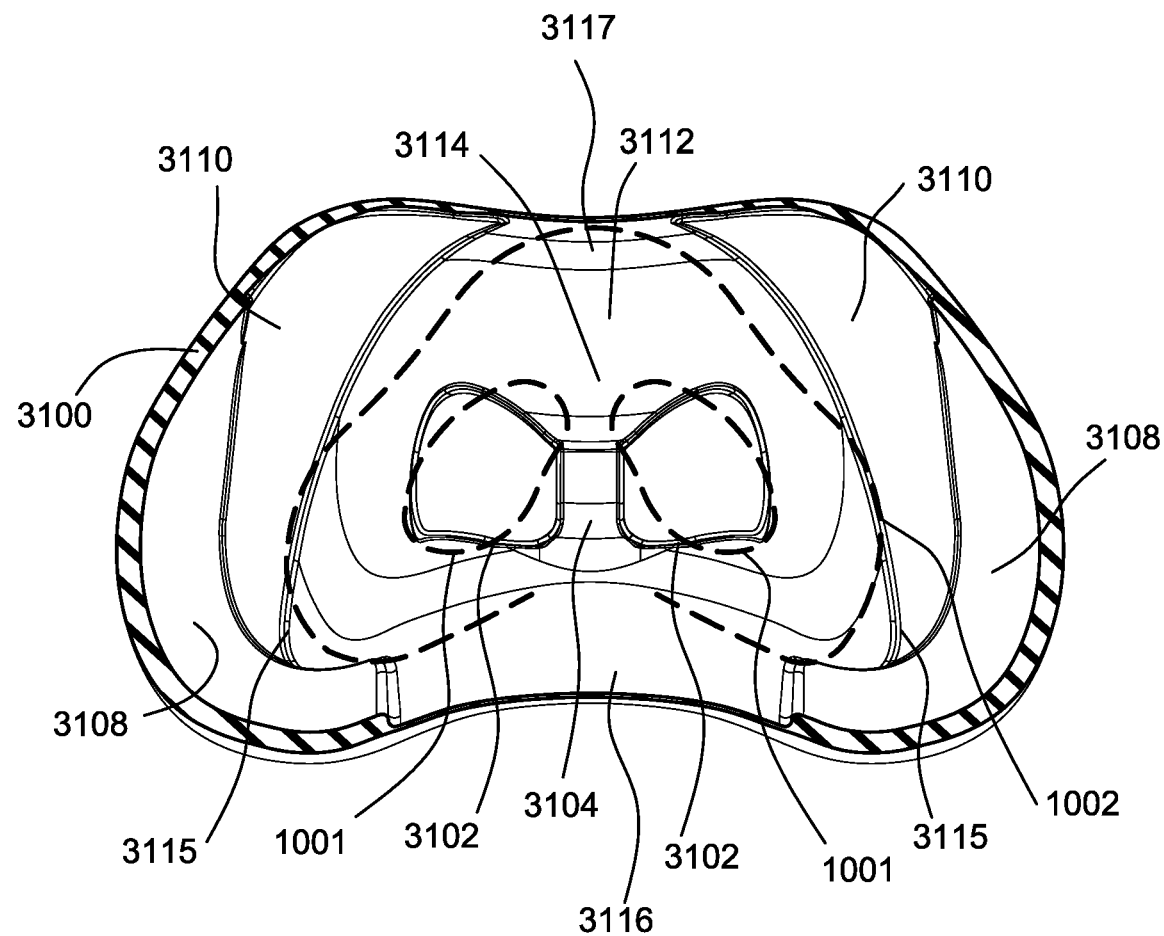

FIG. 68 is a cross-sectional view showing the interior of a seal-forming structure according to an example of the present technology depicted in FIG. 29.

Figure 69:
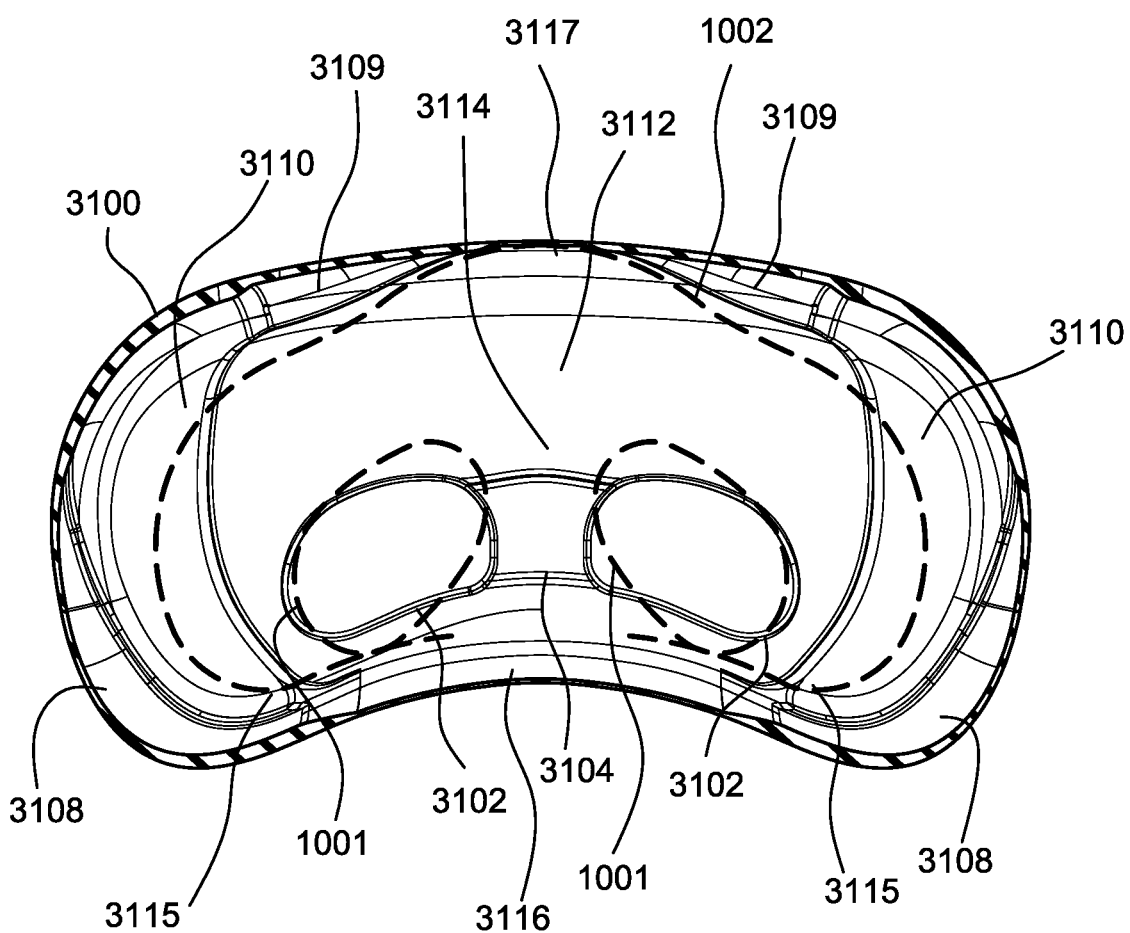

FIG. 69 is a cross-sectional view showing the interior of a seal-forming structure according to an example of the present technology depicted in FIG. 37.

Figure 70:
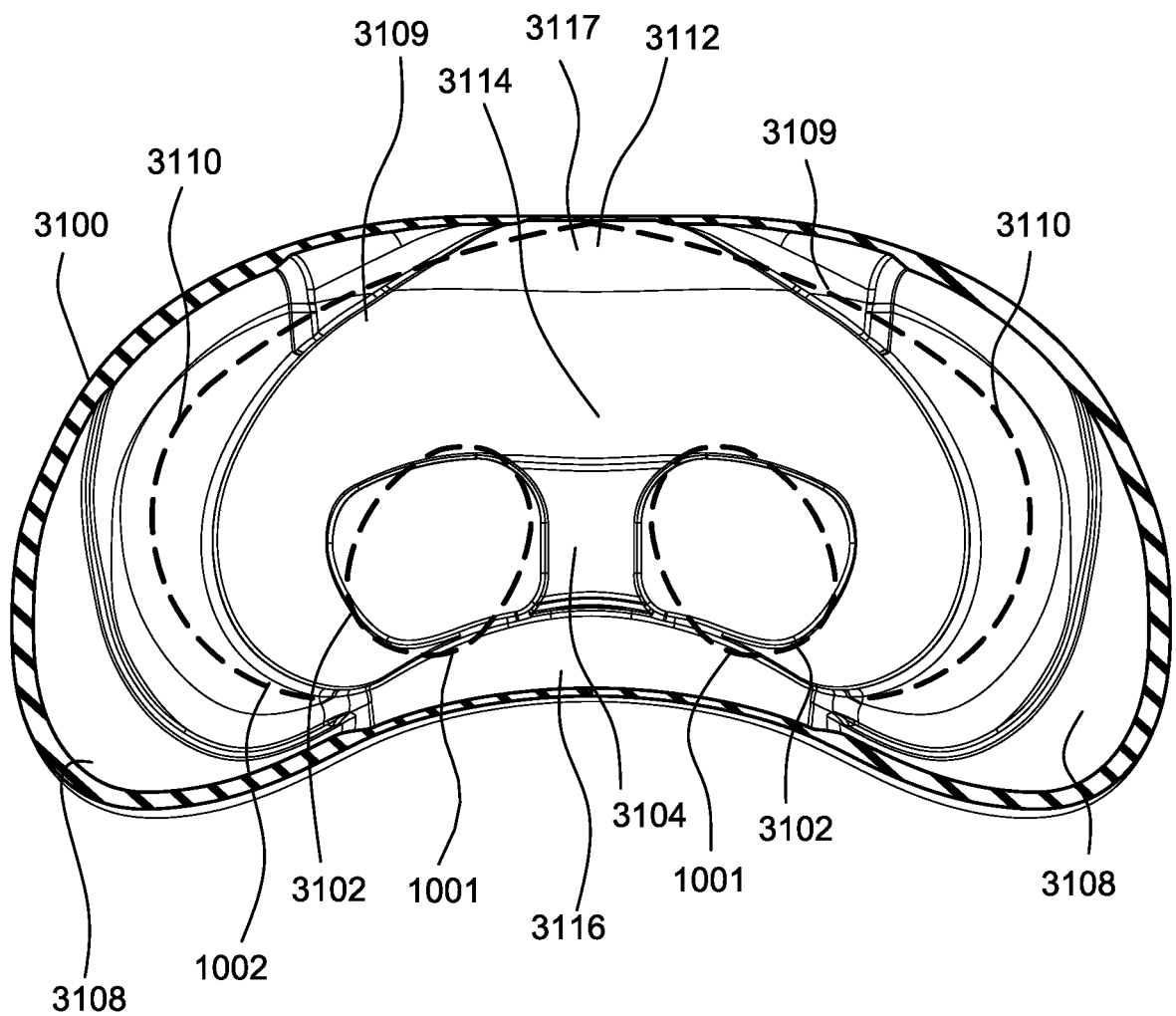

FIG. 70 is a cross-sectional view showing the interior of a seal-forming structure according to an example of the present technology depicted in FIG. 45.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.1.7 Nasal Cradle

FIGS. 16-28 and 67 show a seal-forming structure 3100 according to a first example of the present technology. FIGS. 22-28 show the seal-forming structure 3100 with a plenum chamber 3200, which will be described in greater detail below. FIGS. 29-36 and 68 show a seal-forming structure 3100 according to a second example of the present technology. FIGS. 35 and 36 show the seal-forming structure 3100 with a plenum chamber 3200, which will be described in greater detail below. FIGS. 37-44 and 69 show a seal-forming structure 3100 according to a third example of the present technology. FIGS. 43 and 44 show the seal-forming structure 3100 with a plenum chamber 3200, which will be described in greater detail below. FIGS. 45-52 and 70 show a seal-forming structure 3100 according to a fourth example of the present technology. FIGS. 51 and 52 show the seal-forming structure 3100 with a plenum chamber 3200, which will be described in greater detail below. As can be seen in these views, the different examples are sized and shaped differently and, accordingly, each variation is intended provide an optimal fit for patients having noses and faces shaped and sized differently. FIGS. 16-21, FIGS. 29-34, FIGS. 37-42, and FIGS. 45-50 include broken lines demarcating regions of different thickness, and it should be understood that these are only nominal boundaries, not actual structures.

The four examples of seal-forming structure 3100 described in the preceding paragraph may be considered nasal cradle cushions and are intended to provide a flow of pressurised gas to the patient's nares by sealing against at least the underside of the patient's nose. The exemplary seal-forming structures 3100 will engage the patient's face below the bridge of the nose and some examples, depending on the size and shape of the patient's nose, may engage the patient's nose below the pronasale. In other words, for example, the seal-forming structure 3100 may be structured 3100 so as not to engage the patient's nose superior to the pronasale. The exemplary seal-forming structures 3100 will also engage the patient's face at least above the upper vermillion. Thus, the exemplary seal-forming structures 3100 may seal against the patient's lip superior in use. Furthermore, the patient's mouth may remain uncovered by the seal-forming structure 3100 of the depicted examples such that the patient may breathe freely, i.e., directly to atmosphere, without interference from the seal-forming structure 3100.

Examples of a nasal cradle cushion, e.g., the exemplary seal-forming structures disclosed herein, may include a superior saddle or concave region that has positive curvature across the cushion. Also, a nasal cradle cushion may be understood to have a single target seal forming region or surface, whereas a pillows cushion may have two target seal forming regions (one for each naris). Cradle cushions may also have a posterior wall that contacts the patient's lip superior and an upper, central, surface contacts the underside of the patient's nose. These two surfaces on the patient's face may form a nasolabial angle between them (see FIG.

2E). A cradle cushion may be shaped to have a nasolabial angle within the range of 90 degrees to 120 degrees.

Furthermore, the exemplary seal-forming structures 3100 may also be shaped and dimensioned such that no portion of the seal-forming structure 3100 enters into the patient's nares during use.

The exemplary seal-forming structures 3100, while different in various aspects to be described further below, may each include at least two regions of different thickness: lateral support regions 3108 and a medial region 3114. In further examples, there may also be a third region (in addition to the lateral support regions 3108 and the medial region 3114) of another different thickness, a mid-lateral region 3110. In still further examples, there may also be a fourth region (in addition to the lateral support regions 3108, the mid-lateral regions 3110, and the medial region 3114) of another different thickness, an anterior region 3109. As can be seen the depicted examples, the differing thicknesses may be produced by extending regions of different thickness different distances into the interior of the seal-forming structure 3100 such that the exterior surface of the seal-forming structure 3100 remains smooth. The exterior surface may not be uneven at transitional areas between the regions of different thickness. Thus, the exterior of the exemplary seal-forming structures 3100 is continuous and smooth.

5.3.1.7.1 Lateral Support Region

At each lateralmost side of each seal-forming structure 3100 the lateral support region 3108 may be provided. The exemplary seal-forming structures 3100 may include two lateral support regions 3108, each spaced distal from a plane bisecting the seal-forming structure 3100 that would be parallel to the patient's sagittal plane in use. The lateral support regions 3108 may be the thickest portions of the seal-forming structure 3100 to provide resistance to lateral displacement, e.g., caused by the patient sleeping on the side of their head such that the pillow pushes laterally against the seal-forming structure, and to provide robust engagement against the patient's ala. The lateral support regions 3108 may have a thickness of approximately 0.9 mm to approximately 1.5 mm, or approximately 1.3 mm to approximately 1.4 mm, or approximately 1.3 mm, or approximately 1 mm to approximately 1.5 mm. Due to the lateral support regions 3108 being the thickest regions of the seal-forming structure 3100 in the depicted examples and due to the exemplary seal-forming structures 3100 being constructed or molded from a single, homogeneous piece of material (e.g., liquid silicone rubber), the lateral support regions 3108 may also provide the greatest resistance to deformation.

Additionally, the lateral support regions 3108 may provide sufficient rigidity to ensure adequate sealing in the subalare region of the patient's face (i.e., the region where the ala terminate at the lip superior proximate the nasolabial sulcus), which is a region of particularly complex geometry. The subalare region of a patient's face presents particularly complex geometry because at least three facial surfaces—the ala, the lip superior, and the cheek—converge at this region. Thus, sufficient stiffness in the lateral support regions 3108 may ensure that the seal-forming structure 3100 can be urged into the subalare region by tension forces from the positioning and stabilising structure 3300 without collapsing. Insufficient rigidity at the portions of the seal-forming structure 3100 intended to engage this region of the patient's face, e.g., as a result of the material being too thin, could result in creasing, which forms leak paths from within the sealed region such that the pressurised gas can leak to atmosphere along paths formed within the creases between the exterior of the seal-forming structure 3100 and the patient's facial skin.

The lateral support regions 3108 may lie on the patient's face in a region inferior to the ala of the patient's nose as well as inferior and laterally outwards of the patient's nose, for example, between the nasolabial sulcus and the regions of the lip superior located inferior to the ala.

A dual wall design may be used to prevent collapse of the sealing surfaces, as disclosed in FIGS. 7A-7M of International Application Publication No. WO 2017/185140 A1, which is incorporated herein by reference in its entirety. The examples of the present technology include a seal-forming structure 3100 with a single wall and collapse of the sealing engagement is prevented by, e.g., the increased thickness of the seal-forming structure 3100 at the lateral support regions 3108.

Furthermore, the lateral support regions 3108 may provide resistance to lateral displacement of the seal-forming structure 3100 when the patient's head moves. The seal-forming structure 3100 may be shaped and dimensioned such that when the example of the appropriate size is fitted to a given patient, the lateral support portions 3108 extend around and contact the patient's nasal alae. Since the facial structures underlying the skin of the alae are less rigid (e.g., cartilage and fibro fatty tissue as shown in FIG. 2H), the alae may be more susceptible to deformation, but sufficient rigidity provided by the lateral support regions 3108 may ensure that the seal-forming structure 3100 maintains sealing engagement with the patient's alae when the patient's head moves (e.g., when tilting the head such that one side of the patient interface 3000 is forced against a pillow).

Depending on the shape and size of the patient's facial structures (e.g., nose, alae, lip superior, and cheeks), the lateral support regions 3108 may contact the patient's alae, lip superior, and/or cheeks in use. The lateral support regions 3108, in some examples, may be shaped and dimensioned such that they avoid the patient's pronasale and/or subnasale.

FIGS. 67-70 depict examples of the seal-forming structures 3100 shown with exemplary naris outlines 1001 and nose base outlines 1002. Although, these examples do not show the alar region of the nose base outline 1002 extending wide enough to contact the lateral support regions 3108, it should be understood that the in use the lateral support regions 3108 may extend superiorly so as to envelop the alae. Therefore, the inferior portion of the patient's alae may not contact the lateral support portions 3108, but the lateral portions of the patient's alae may contact the lateral support portions 3108 once the nose is received into the seal-forming structure 3100. This fit is subject to the size and shape of the nose of a given patient and in some examples the patient's nose may be sufficiently wide so that the inferior portions of the alae do contact lateral support portions 3108, in addition to the lateral portions of the alae. In further examples, the patient's nose may be so narrow that no portion of the alae contact the lateral support regions 3108.

As can be seen in FIGS. 67-70, there may be a rather abrupt transition (e.g., an abrupt taper or almost a step) between regions of different thickness. While facial geometry can vary widely between patients, the abrupt transitions may be located almost directly inferior to the nasal ala on the lip superior.

The edge of the lateral support regions 3108 may track upwardly, outwardly, and then inwardly to follow curvature of the nose in a superior direction starting from under patient's ala (e.g. "up" the patient's face on either side the nose following the curvature along either side of the nose). Thus, the lateral support regions 3108 support the seal-forming structure 3100 against the patient's face inferior to and on lateral sides of the patient's nose, while enabling the medial region 3114 to conform and seal to the alae and underside of the patient's nose.

The lateral support regions 3108 may extend from the plenum chamber 3200 all the way to the corners of the seal-forming structure 3100 to support and structurally rigidize the cushion. In some examples, the lateral support regions 3108 may be their thickest adjacent to where the seal-forming structure 3100 joins with the plenum chamber 3200 and then decreases in thickness away from the plenum chamber 3200. The lateral support regions 3108 may not extend around the entirety of the plenum chamber 3200, however. For example, the medial region 3114, as described below, may extend to the peripheral edge of the plenum chamber 3200 at the central superior/anterior region of the seal-forming structure 3100.

While the increased thickness of the lateral support regions 3108 may be desirable for structural rigidity, the seal-forming structure 3100 may still retain a degree of flexibility to enable the lateral portions of the seal-forming structure 3100 to be pushed laterally or pulled medially to accommodate noses of different widths. For example, the non-patient facing sides of the seal-forming structure 3100 (particularly the non-patient contacting regions on either lateral side of the seal-forming structure 3100) may be thick enough to provide sufficient structural rigidity to the seal-forming structure 3100, but may still be thin enough so that when the seal-forming structure 3100 is donned by a patient with a long narrow nose, the compressive forces in the anterior direction exerted by the patient's nose on the medial region 3114 are able to pull the lateral sides of the seal-forming structure 3100 (i.e., the lateral support portions 3108) medially to bring the so that the seal-forming structure 3100 on either lateral side of the patient's nose contacts the patient's nose (e.g., at the alae). If a patient with a wider nose dons the seal-forming structure 3100, the seal-forming structure 3100 may be sufficiently flexible such that there is not an excessive force in the medial direction on the lateral sides of the patient's nose, which may occur if the seal-forming structure 3100 is too stiff to tolerate a wider nose.

5.3.1.7.2 Medial Region

The medial region 3114 may be centrally located on the seal-forming structure 3100. The medial region 3114 may be bisected by a plane that is parallel to the patient's sagittal plane in use. Since the medial region 3114 is centrally located, there may be only one such region.

In the depicted examples, naris openings 3102 may be formed through the medial region 3102. The naris openings 3102 are positioned to generally align with patient's corresponding naris to provide the flow of pressurised gas to the patient's nares for inhalation and for exhaled gas to be passed back into the seal-forming structure 3100 for discharge to atmosphere via the plenum chamber vent 3400, as described further below. FIGS. 67-70 show examples of the general alignment of the naris outlines 1001 with corresponding naris openings 3102. These examples show that the naris outline 1001 may not necessarily match the size and shape of the naris opening 1002 because patients exhibit large variability in the size and shape of their nares.

As can be seen in the examples of FIGS. 67-70, the medial region 3114 may contact a substantial portion of the base or underside of the patient's nose. In many patients, this is a particularly sensitive region. Also, patients exhibit a large amount of variability in the geometry of the base or underside of the nose. Therefore, the medial region 3114 may be relatively thin as compared to other regions of the seal-forming structure 3100 to increase flexibility and conform to contours of the patient's facial and nasal geometry. In the depicted examples, the medial region 3114 is the thinnest region. In these examples, the medial region 3114 may have a thickness of approximately 0.25 mm.

The depicted examples show the mid-lateral regions 3110 laterally outward of the medial region 3114, and the lateral support regions 3108 are shown further laterally outward. Thus, in some examples and depending on the size and shape of the patient's nose, the alae may not contact the medial region 3114 at all if the nose is wide enough. In patients with narrower noses, a portion of their alae may contact the medial region 3114.

The medial region 3114 may also extend around to the anterior side of the seal-forming structure 3100 such that the patient's pronasale contacts a superior portion of the medial region 3114. The patient's lip superior and/or subnasale may also contact an inferior portion of the medial region 3114. The pronasale, lip superior, and subnasale may also be particularly sensitive regions and, therefore, it may be beneficial for the increased compliance of the medial region 3114 to engage these sensitive regions and reduce discomfort. As can be seen in the views of these examples, Depending on the shape and size of the patient's facial structures (e.g., nose, alae, lip superior, and cheeks), the medial region 3114 may contact the patient's lip superior, subnasale, and/or pronasale in use. The medial region 3114, in some examples, may be shaped and dimensioned such that they avoid the patient's pronasale and/or subnasale.

Within the medial region 3114, there may be a pronasale region 3117 where the patient's pronasale may contact the seal-forming structure 3100. However, it should be understood that shorter noses may not reach the pronasale region 3117 and longer noses may extend beyond the pronasale region 3117 such that the pronasale in either case does not contact the pronasale region 3117. The pronasale region 3117 in the examples of FIGS. 16-28 and 67 and FIGS. 29-36 and 68 may extend over to an anterior side of the seal-forming structure, i.e., away from the patient such that a portion of the pronasale region 3117 does not contact the patient's face. This arrangement may also allow the engagement of the pronasale to pull the lateral sides of the seal-forming structure 3100 medially to engage the alae. The pronasale region 3117 in the examples of FIGS. 37-44 and 69 and FIGS. 45-52 and 70 may not extend so far forward as to have a portion that is not able to be contacted by the patient's nose because these shapes are intended for wider noses that may already be able to adequately engage lateral portions of the seal-forming structure 3100.

Within the medial region 3114, there may be a lip superior region 3116 where the patient's lip superior may contact the seal-forming structure 3100. The patient's subnasale may also contact the seal-forming structure 3100 at the lip superior region 3116. In some examples, the lip superior region 3116 may be adjacent to but not in direct contact with the patient's subnasale. Thus, there may be a gap between the patient's face and the seal-forming structure 3100 within the boundary of the seal formed against the patient's face.

Additionally, since the medial region 3114 is relatively thin, the pressure of the air within the seal-forming structure 3100 may cause the seal-forming structure 3100 to inflate during use. By inflating the seal-forming structure 3100 during use, the medial region 3114 is readily urged against the contours of the patient's face and nose, e.g., at the underside, at the alae, at lip superior, at the subnasale, and/or at the pronasale, to ensure an adequate seal.

While a relatively low material thickness may have benefits described above and below for the medial region 3114, making the medial region 3114 too thin may result in excessive creasing, which in turn can form leak paths for gas to escape to atmosphere past the sealing boundary. Also, the medial region 3114 may benefit from being thick enough to maintain a stable seal that is not readily displace by movement of the patient or contact with objects such as pillows. Creasing may be of particular concern at the pronasale region 3117, particularly along the centerline of the seal-forming structure 3100 (i.e., along a plane parallel to the patient's sagittal plane in use). Thus, in some examples the medial region 3114 may be thickened at the pronasale region 3117 relative to other portions of the medial region 3114.

Within the medial region 3114, there may also be a bridge portion 3104 positioned between the naris openings 3102. The bridge portion 3104 may be long enough to be slack in an undeformed state such that when the patient's nose contacts the medial region 3114 the bridge portion 3104 can accommodate deformation of the seal-forming structure 3100 without stretching. The bridge portion 3104 may be thicker than the medial region 3114 or may be the same thickness. In an example, the bridge portion has a thickness of approximately 0.35 mm. An alternative way to resist tearing is for the bridge portion 3104 to be wider. Constructing the bridge portion 3104 with relatively greater thickness than the adjacent medial region 3114 may help to prevent tearing when the bridge portion 3104 is elongated by engagement of the seal-forming structure 3100 with the patient's nose. The bridge portion 3104 may be S-shaped to permit straightening to tolerate movement of the superior part of the medial region 3114 away from the inferior lip superior part. The bridge portion 3104 may be bowed, curved, and/or somewhat folded in its undeformed state.

The bridge portion 3104 may be longer or have more material than is necessary to bridge the gap between the top and bottom portions of the medial region 3114. This extra material allows for extension while the bridge portion 3104 straightens, before becoming taut. If there was no extra material, the bridge portion 3104 could become taut upon a force applied to the top portion of the medial region 3114, and the bridge portion 3104 would not tolerate any movement of the top portion of the medial region 3114 (and therefore may not achieve the effect of tolerating longer noses). Since the bridge portion 3104 may not necessarily engage and seal to the columella in order to fully seal around to the patient's nose, an adequate seal can be made to a small nose even if the bridge portion 3104 remains slack.

The bridge portion 3104 may maintain the integrity of the seal-forming structure 3100 in the medial region 3114. If there were no bridge portion 3104 and instead a single air opening, due to the relatively thin wall thickness of the medial region 3114, if the seal-forming structure 3100 is refitted (e.g., via pulling of the face and reseating) or receives aggressive dynamic loading whilst under pressure, there may be a risk that the pronasale region 3117 of the seal-forming structure 3100 would blow out (i.e., pressure from the gas would blow the sealing surface away from the nose and prevent sealing engagement). The bridge portion 3104 may prevent blow out by tying the pronasale region 3117 to the lip superior region 3116.

Additionally, the bridge portion 3104 may prevent user set up error by preventing the patient's nose from being inserted into what would otherwise be a single hole.

5.3.1.7.3 Mid-Lateral Region

The mid-lateral regions 3110 may be provided laterally inward or in the medial direction relative to the lateral support regions 3108. The mid-lateral regions 3110 may be laterally outward relative to the medial region 3114. The exemplary seal-forming structures 3100 may include two mid-lateral regions 3110, each spaced distal from a plane bisecting the seal-forming structure 3100 that would be parallel to the patient's sagittal plane in use. The mid-lateral regions 3110 may be positioned such that each mid-lateral region 3110 is adjacent to a corresponding lateral support region 3108 on one side and on the other side is adjacent to a corresponding side of the medial region 3114.

Depending on the shape and size of the patient's facial structures (e.g., nose, alae, lip superior, and cheeks), the mid-lateral regions 3110 may contact the patient's alae in use. The mid-lateral regions 3110, in some examples, may be shaped and dimensioned such that they avoid the patient's lip superior, cheeks, pronasale, and/or subnasale. FIGS. 67-70 show examples of the alae contacting the mid-lateral regions 3110 as the nose base outline 1002 extends to the mid-lateral regions 3110 at its widest point, which is the lateral boundary of the base of the alae. In other examples, where the patient has a relatively narrow nose, the nose base outline 1002 may remain within the boundary of the medial region 3114 such that the mid-lateral regions 3110 and the lateral support regions 3108 contact the lateral portions of the alae but not the underside. In other examples where the patient's nose is relatively wide, the base of the alae may extend beyond the mid-lateral regions 3110 to the lateral support regions 3108.

The mid-lateral regions 3110 may be thicker than the medial region 3110 and thinner than the lateral support regions 3108 in some examples. The mid-lateral regions 3110 may have a thickness of approximately 0.5 mm to approximately 0.7 mm or approximately 0.6 mm or approximately 0.75 mm.

5.3.1.7.4 Anterior Region

Further examples of the seal-forming structure 3100 may include an anterior region 3109. The anterior region 3109 may face away from the patient in use and in some examples the patient's face may not contact the anterior region 3109. The anterior region 3109 may be thinner than the lateral support regions 3108 and thicker than medial region 3114 in some examples. In some examples, the anterior region 3109 may have a thickness of approximately 0.5 mm to approximately 0.7 mm or approximately 0.6 mm or approximately 0.75 mm.

The anterior region 3109 may support the seal-forming structure 3100 by resisting compression of the seal-forming structure 3100 in the anterior direction during use.

5.3.1.7.5 Corner Region

The exemplary seal-forming structures 3100 may also include two corner regions 3115 formed at approximately the region where the medial region 3114, the lateral support regions 3108, and the mid-lateral regions 3110 converge. The corner regions 3115 may be located medially relative to the lateral support regions 3108 or relative to the lateral support regions 3108 and the mid-lateral regions 3110.

As can be seen in FIGS. 67-70, the corner regions 3115 may engage the patient's nose and face at approximately the region where the nose base outline 1002 terminates (i.e., at the subalare region). The corner regions 3115 may be shaped and dimensioned to extend into and seal with the subalare region of the patient's face. As explained above, the relatively thick lateral support regions 3108 may be effective at ensuring that an adequate seal is maintained at regions of relatively complex facial geometry, such as the subalare region. Thus, by extending the corner regions 3115 medially the lateral support regions 3108 or the lateral support regions 3108 and the mid-lateral regions 3110 extend into the subalare region to provide an effective seal in the complex and concave geometry of this region.

The alae in some patients may be significantly curved, and many patients may have very concave pockets or cavities where the ala meets the face, i.e., the subalare region. The pockets can result from alae that curve medially towards the sagittal plane between the widest part of the nose (i.e., along a line drawn from alar crest point to alar crest point across the sagittal plane) and the junction of the ala and the face (i.e., the subalare region). Providing thin material (i.e., the medial region 3114 component of the corner regions 3115) to engage these corners of the patient's facial geometry may enable the seal-forming structure 3100 to deform to match the curvature of the ala and at least partially, if not completely, filling the concavities which may exist at the inferior corners of the patient's nose. The seal-forming structure 3100 may be configured so that the edge of the lateral support regions 3108 may be located on the patient's face laterally outward of the alae, but close enough to the alae so that the regions of the cushion contacting the patient's face on either inferior side of the nose are within the lateral support regions 3108 to support and stabilize to the seal-forming structure 3100. The medial region 3114 component of the corner regions 3115 may deform to the extent that shelves are formed on which the patient's alae (at least the portions thereof proximate the lip superior) may lie in use, enabling the seal-forming structure 3100 to conform to the inferior periphery of the patient's nose in use, especially proximate the lip superior.

5.3.1.7.6 Crease Resistance

Providing the medial region 3114 to the seal-forming structure 3100 to seal to the underside of a patient's nose and providing the mid-lateral region 3110 and/or the lateral support portions 3108 around some or all of the medial region 3114 approximately at the periphery of the patient's nose may prevent propagation of creases formed on the relatively flexible and thin medial region 3114.

As the medial region 3114 has a thin wall thickness and, therefore, may be relatively flexible, the medial region 3114 may be prone to creasing. The mid-lateral region 3110 may be thicker than the medial region 3114 and, therefore, may be less prone to creasing, particularly at the alar regions that may be more susceptible to creasing due to complex geometry. If a crease begins at a surface of the seal-forming structure 3100 that seals with the patient's skin and continues outside of the boundary of the seal, the crease may create a leak path through which gas can leak through the crease to ambient, past the patient's face. This may generate noise due to jetting and/or disruption due to the sensation of the gas flowing along the skin.

The mid-lateral regions 3110, by virtue of the increased wall thickness, may resist creasing. If a crease occurs in the medial region 3114, the mid-lateral region 3110 may be able to limit the size of the crease to prevent it from continuing up the sides of the seal-forming structure 3100 and past the surface forming a seal against the skin. Accordingly, the mid-lateral regions 3110 may act as a barrier to creases that closely follow the shape of the patient's nose, by being configured to lie at or proximate the edges of the patient's alae around the base of the nose.

Additionally, the mid-lateral regions 3110 may provide some medial preload to the lateral sides of the seal-forming structure 3100. The patient's nose may act against this preload when the patient dons the mask, and in turn the lateral sides of the seal-forming structure 3100 are pushed into the alae to form a stable and robust seal. The preload may be designed to be large enough that the seal-forming structure 3100 can fit to and create a robust seal with a narrow nose, but not so large that it would be uncomfortable or resist sealing for a wider nose. Additionally, the preload on the sides of the nose may provide suspension between the nose and the rest of the seal-forming structure 3100, providing a decoupling effect and allowing some lateral movement of the cushion in use without disrupting the seal.

5.3.1.7.7 Sealing and Comfort of the Seal-Forming Structure of the Present Technology Preferred by Patients In an external clinical study, 19/23 patients rated the seal-forming structures 3100 of the present technology as having comfort above 7 on a scale of 1-10, 10 being the highest. In an external clinical study, 15/23 patients rated the seal-forming structures 3100 of the present technology as having comfort of a 9 or 10.

In a fitting study, the majority of patients (30/33) preferred the initial fit of the seal-forming structures 3100 of the present technology to that of a competitor product (Respironics DreamWear), praising its ease of fit, adjustment and seal. 30 of 33 patients (90%) found the seal-forming structures 3100 of the present technology very easy to fit and adjust. 31 out of 36 people rated the seal of the seal-forming structures 3100 of the present technology at a 9 or a 10 on a scale of 1-10, 10 being the highest. In this engineer-observed study, patients found that the seal of the seal-forming structures 3100 of the present technology was better at tolerating movement in a bed than the competitor product (Respironics DreamWear).

The majority of patients (31 out of 36 patients) who tested the seal-forming structures 3100 of the present technology loved them and would take them home as their mask of choice when compared with the competitor product (Respironics DreamWear).

The comfort preferences described in the preceding paragraphs may be associated with the comfort provided to the patient by the medial region 3114, which provides compliant and conforming engagement with sensitive areas of the patient's face. The overall shape of the exemplary seal-forming structures 3100 may also contribute to the comfort.

The sealing preferences described in the preceding paragraphs may be associated with the medial region's 3114 ability to conform to the patient's nose to form an adequate seal. Also, the mid-lateral regions 3110, the lateral support regions 3108, and the corner regions 3115 may also contribute to the preference for the seal of the seal-forming structure 3100 of the present technology because of the way that these structures engage complex facial geometries to maintain an effective seal.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

FIGS. 22-28, 35, 36, 43, 44, 51, and 52 show examples of the seal-forming structure 3100 with the plenum chamber 3200. The seal-forming structure 3100, as described above, may be formed from a single, homogeneous piece of material (e.g., liquid silicone rubber), and may include a plenum chamber connection opening 3106 where the seal-forming structure 3100 is joined to the plenum chamber 3200. The connection between the seal-forming structure 3100 and the plenum chamber 3200 at the plenum chamber connection opening 3106 may be a permanent bond. The connection between the seal-forming structure 3100 and the plenum chamber 3200 at the plenum chamber connection opening 3106 may be a chemical bond. The seal-forming structure 3100 may be joined to the plenum chamber 3200 at the plenum chamber connection opening 3106 without a mechanical interlock.

At each lateral side of the plenum chamber 3200 there may be a plenum chamber lateral end 3202 in the form of a hollow passageway. A plenum chamber connector 3204 may also be provided at each lateral side of the plenum chamber 3200 laterally outward of the plenum chamber lateral end 3202. The plenum chamber connectors 3204 may connect to respective ends 3314 of the positioning and stabilising structure 3300. The connection between the plenum chamber connectors 3204 and respective ends 3314 of the positioning and stabilising structure 3300 may be releasable at both sides. In other examples, one side may have a permanent connection while the other side has a releasable connection. In still further examples, both connections between the plenum chamber connectors 3204 and respective ends 3314 of the positioning and stabilising structure 3300 may be permanent.

The plenum chamber lateral ends 3202 may receive the flow of pressurised gas from the positioning and stabilising structure 3300. The flow of pressurised gas may then pass through the plenum chamber 3200, then through the seal-forming structure 3100, and into the patient's airways for inhalation.

FIGS. 55-61 show examples of how the ends 3114 of the positioning and stabilising structure 3300 may be connected to the plenum chamber lateral ends 3202. Each plenum chamber connector 3204 in these examples may include a notch 3206 that is connected to a clip projection 3322 of a clip 3320 with a snap-fit. Each plenum chamber connector 3204 may be split to allow deformation within the clip 3320 during connection. Each clip 3320 may be joined to a clip overmold 3318, which is an intermediate component between the end 3314 of the positioning and stabilising structure 3300. Surrounding the ends 3314 of the positioning and stabilising structure 3300 may be a lip 3324 that seals with the plenum chamber connector 3204. The lip 3324 may surround the entire opening at the end 3314 of the positioning and stabilising structure 3300 to ensure a complete and gas tight seal against the plenum chamber connector end 3204 so that the entire flow of pressurised gas passing through the positioning and stabilising structure 3330 reaches the patient via the plenum chamber 3200 and the seal-forming structure 3100.

The plenum chamber connectors 3204 may each include a chamfered edge 3208 and a slot 3209. The chamfered edge 3208 may form a surface to engage the clip projections 3322 of the clip 3320, e.g., as shown in FIG. 57. The slots 3209 may allow the plenum chamber connectors 3204 to be deformed to a reduced cross-section when inserted into corresponding clips 3320.

The clip overmold 3318 may be a thin layer of silicone material between the clip 3320 (e.g., constructed of polycarbonate) and the positioning and stabilising structure 3300. The clip overmold 3318 may be constructed of silicone to improve bonding between the positioning and stabilising structure 3300 and the clip 3320. Bonding between compression grade silicone (e.g., used for the positioning and stabilising structure 3300) and plastic (such as the polycarbonate used for the clip 332) may be poor. Thus, a layer of LSR (Liquid Silicone Rubber), in the form of the clip overmold 3318, may be overmoulded between the clip 3320 and the compression grade silicone positioning and stabilising structure 3300 to improve bonding.

FIG. 56 also shows an alignment feature whereby two arrowheads, one on the plenum chamber 3200 and one on the positioning and stabilising structure 3300, indicate proper engagement of the plenum chamber 3200 with the positioning and stabilising structure 3300.

The plenum chamber connectors 3204 may be chamfered at their ends to provide lead-in angles for connection to the positioning and stabilising structure 3300. These lead-in features may reduce the force needed to insert the plenum chamber connectors 3204 into the ends 3314 of the positioning and stabilising structure 3300, specifically the clips 3320. Additionally, the lead-in chamfers on the plenum chamber connectors 3204 may aid in self-alignment with the clips 3320 during assembly. The clips 3320 may also have lead-in chamfers to further assist in deforming the plenum chamber connectors 3204 for connection.

Notches 3206 may be provided to the plenum chamber connectors 3204 to for the clips 3320 to fit into during assembly for a snap-fit connection. Once the clip 3320 fits into the corresponding notch 3206, the plenum chamber 3200 and the positioning and stabilising structure 3300 are removably joined together. These components can be disconnected by applying enough force for the clip projections 3322 to escape the corresponding notches 3206. The edge of each of the notches 3206 distal relative to the end of the plenum chamber connector 3204 is provided with a surface at an angle with respect to the direction in which the plenum chamber 3200 pulled away from the clip 3320 during disassembly of the plenum chamber 3200 from the positioning and stabilising structure 3300. The retention angle may provide optimum force for retaining the positioning and stabilising structure 3300 during use while allowing an easy disconnection of the plenum chamber 3200 and the positioning and stabilising structure 3300. A steeper angle would make the connection more secure and avoid unintentional disassembly, but it would be more difficult for the patient to disassemble the system. The retention angle depicted strikes a balance resulting in secure assembly and ease of disassembly.

The plenum chamber connectors 3204 may be curved to match the curve of the inner profile of the positioning and stabilising structure 3300. The upper one of the plenum chamber connectors 3204 in FIG. 57 is curved and does not flex during connection and disconnection. The lower one of the plenum chamber connectors 3204 in FIG. 57 is not curved and is able to flex during connection and disconnection in order to allow the plenum chamber connectors 3204 to fit into the clip 3320 inside the positioning and stabilising structure 3300.

Providing a sufficient radius of curvature at the base of the split between the plenum chamber connectors 3204 may avoid stress concentrations. The rigid material (e.g., polycarbonate) could otherwise fail at this location due to the stress created when the bottom one of the plenum chamber connectors 3204 flexes to receive the clip 3320.

The cross-sectional profile of the plenum chamber connectors 3204 may not follow the cross-section profile of the clip 3320 exactly. There may be more clearance at sides of the plenum chamber connectors 3204 than at the top and bottom, which may allow the clip 3320 to flex during assembly and disassembly without interfering with the plenum chamber connectors 3204. When the plenum chamber connectors 3204 are pulled from the clip 3320, the plenum chamber connectors 3204 may exert force on the clip 3320 in the up and down directions of FIG. 57, which may cause the sides of the clip 3320 to be drawn inwards as the clip deforms. Providing some clearance between the sides of the clip 3320 and the plenum chamber connectors 3204 may allow some room for the sides of the clip 3320 to move inwards without interfering with the plenum chamber connectors 3204. The clip 3320 thickness may be chosen to allow both flexibility and the retention forces required to maintain a secure connection.

The end 3314 of the positioning and stabilising structure 3300 may be small enough to form an interference fit with the plenum chamber connectors 3204 to seal between the plenum chamber 3200 and the positioning and stabilising structure 3300. The lip 3324 cross-section may be tapered to prevent rolling in of lip 3324 during assembly, which could adversely affect the seal.

FIGS. 60 and 61 show that the internal opening 3201 between the plenum chamber connectors 3204 and the interior of the plenum chamber 3200 may have a very similar geometry to the positioning and stabilising structure 3300, avoiding changes that could adversely affect the flow dynamics and cause excessive pressure drop. The transition geometry from the inside of the plenum chamber connectors 3204 to the interior of the plenum chamber 3200 and the seal-forming structure 3100 may also minimize pressure drop and impedance.

5.3.2.1 Alternative Plenum Chamber Design

FIGS. 64-66 depict variations of the plenum chamber 3200. In one example, the plenum chamber 3200 may be formed of a flexible material such as silicone rather than a rigid material such as polycarbonate. Thus, the plenum chamber 3200 may be more flexible and may better tolerate or decouple lateral forces on the positioning and stabilising structure 3300, which may reduce the forces transmitted to the seal-forming structure 3100 that could disrupt the seal. A plenum chamber 3200 made from a more flexible material such as silicone may also be easier to remove from the tooling during manufacturing. In such an example, the connections to the gas-transporting positioning and stabilising structure 3300 may still be formed from a rigid material, e.g. polycarbonate.

In such an example, the seal-forming structure 3100 may be constructed of a very soft silicone, such as in the range of 30-40 Durometer. The plenum chamber 3200 may not be as soft (but still softer than a rigid material like polycarbonate), with a hardness in the range of 70-90 Durometer, for example. The plenum chamber connectors 3204 may formed from a hard, plastic material, such as polycarbonate or nylon. Vent holes 3400, if the holes are large enough (or the silicone is stiff enough) could be provided as vent holes in the flexible material, e.g., silicone, of the plenum chamber 3200. The holes in such examples should be sufficiently large or the material sufficiently to avoid occlusion. Alternatively, the plenum chamber 3200 could be provided with larger openings into which an inserts (e.g., a rigid material such as polycarbonate) having the vent holes could be fitted or overmoulded. This alternative is depicted in FIGS. 62-63. A diffuser may also be provided with or in addition to the vent insert 3242.

FIGS. 64-66 depict an example wherein the plenum chamber 3200 is split into two plenum chamber portions 3260 which are separated by a flexible material like silicone. Thus, the plenum chamber 3200 may flex at the center. This may provide some decoupling of forces between the positioning and stabilising structure 3300 and the seal-forming structure 3100, and may also enable the seal-forming structure 3100 to deform and wrap around the patient's face. Each of the plenum chamber portions 3260 may be connected to the positioning and stabilising structure 3300 to direct gas into the plenum chamber 3200. The plenum chamber portions 3260 may also include vents 3400.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.3.1 Positioning and Stabilising Structure of the Present Technology

FIGS. 7-15 depict examples of the present technology, including a positioning and stabilising structure 3300. In these examples, the positioning and stabilising structure 3300 includes lateral portions 3302 and superior portions 3304 in the form of conduits or tubes that direct a flow pressurised gas from a hub 3306 to ends 3314. The positioning and stabilising structure 3300 may be arranged such that the hub 3306 and the decoupling structure 3500 are positioned superior to the patient's head in use. As described below, the decoupling structure 3500 may be rotatable within the hub 3306 and when the patient is wearing the patient interface 3000, e.g., during therapy, the location of the hub 3306 and the decoupling structure 3500 superior to the patient's head allows the patient to move more freely without becoming entangled with the air circuit 4170.

The positioning and stabilising structure 3300 may be constructed of silicone. For example, the lateral portions 3302, the superior portions 3304, the hub 3306, and the lateral ends 3314 may able constructed or molded from a single piece of silicone.

The superior portions 3304 of the positioning and stabilising structure 3300 have ridges and valleys (or concertina sections) that allow the superior portions 3304 to conform to the shape of the corresponding portion of the patient's head in use. The ridges and valleys of the superior portions 3304 allow the superior portions 3304 to be extended and contracted along the longitudinal axis to accommodate larger or smaller heads. The ridges and valleys of the superior portions 3304 allow the superior portions 3304 to be flexed to different radii of curvature to accommodate patient heads of different shapes and sizes.

The lateral portions 3302 portions of the positioning and stabilising structure 3300 may not be formed with the ridges and valleys of the superior portions 3304. Therefore, the lateral portions 3302 may be less extensible and flexible than the superior portions 3304, which may be advantageous because there is less variability in the shape and size of the lateral sides of a patient's head.

The ends 3314 may connect to respective plenum chamber lateral ends 3202. As described above, the plenum chamber lateral ends 3202 receive the flow of pressurised gas from the positioning and stabilising structure 3300, which passes through the plenum chamber 3200, through the seal-forming structure 3100, and on to the patient's airways. As described above, the ends 3314 may include clip overmolds 3318 and clips 3320 that facilitate connection of the ends 3314 to the plenum chamber connectors 3204 of a respective plenum chamber lateral end 3202.

The lateral portions 3302 may also each include a tab 3308 that receives a posterior strap end portion 3311 of a posterior strap 3310. The posterior strap 3310 may be length-adjustable, e.g., with a hook and loop material arrangement whereby one of the posterior strap end portion 3311 and the remainder of the posterior strap 3310 includes hook material on its exterior while the other includes loop material on its exterior. The length adjustability of the posterior strap 3310 allows tension on the lateral portions 3302 to be increased to pull the seal-forming structure 3100 into sealing engagement with the patient's face at a desired amount of pressure (i.e., sufficiently tight to avoid leaks while not so tight as to cause discomfort).

The lateral portions 3302 may also be provided with sleeves 3312 that cushion the patient's face against the lateral portions 3302. The sleeves 3312 may be constructed of a breathable textile material that has a soft feel.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. The plenum chamber vent 3400 may comprise a plurality of holes, as described above. The holes of the plenum chamber vent 3400 may be divided into two groups spaced apart laterally. The axis of the flow path through each of the holes of the plenum chamber vent 3400 may be parallel such that cross-flow is avoided to prevent generation of additional noise. The vent holes may be circular.

FIG. 54 also shows that the holes of the plenum chamber vent 3400 may decrease in radius from the interior of the plenum chamber 3200 to the exterior. As shown, each vent hole is provided with a draft angle. Each hole has a smaller diameter at its anterior end than at its posterior end. The draft angle means that the holes do not have a small cross section across the entire chassis thickness, which helps to provide effective carbon dioxide wash out at high levels of humidification. Additionally, a larger draft angle may result in a plenum chamber 3200 that is easier to manufacture, especially when the plenum chamber 3200 is formed from an injection moulded plastics material. The draft angle enables relatively thick vent pins to be used in the mould and easier ejection.

The holes of the plenum chamber vent 3400 may be provided in two sets towards the middle of the plenum chamber 3200 and the sets may be symmetrical across the centreline of the plenum chamber 3200. Providing a pattern of multiple vent holes may reduce noise and diffuse the flow concentration.

The holes of the plenum chamber vent 3400 may be placed at an optimum distance away from the centreline of the plenum chamber 3200. Placing the holes of the plenum chamber vent 3400 towards the centreline may advantageously reduce the chance that the vent holes are blocked when the patient is sleeping on their side. However, placing the vent holes too close to the middle of the plenum chamber 3200 may result in excessive weakening of the plenum chamber 3200 at the centre, especially since the cross-section of the plenum chamber 3200 in the depicted examples is smallest at the centre due to the overall shape of the plenum chamber 3200. The location of the holes of the plenum chamber vent 3400 may avoid hole blockage during side sleep while leaving the middle section of the chassis sufficiently strong.

The size of each vent hole and the number of vent holes may be optimised to achieve a balance between noise reduction while achieving the necessary carbon dioxide washout, even at extreme humidification. In the depicted examples, the vent holes of the plenum chamber vent 3400 may not provide the total amount of venting for the system. The decoupling structure 3500 may include a decoupling structure vent 3402. The decoupling structure vent 3402 may include one hole or a plurality of holes through the decoupling structure 3500. The decoupling structure vent 3402 may function to bleed off excess pressure generated by the RPT device 4000 before reaching the patient, while the plenum chamber vent 3400 may function to washout carbon dioxide exhaled by the patient during therapy.

FIGS. 62 and 63 show an alternative example of the plenum chamber vent 3400 in which holes are provided to a vent insert 3242 that attaches, removably or permanently, to the plenum chamber 3200 at a vent insert opening 3240. The vent insert 3242 may be constructed from a material that is more flexible than the material of the plenum chamber 3200.

5.3.5 Decoupling Structure(s)

In one form the patient interface 3000 includes at least one decoupling structure, for example, a swivel or a ball and socket.

The hub 3306, described above, is connected to a decoupling structure 3500, which is a rotatable elbow in these examples. The decoupling structure 3500 may be rotatable 360° within the hub 3306 in use. The decoupling structure 3500 may be removable from the hub 3306 by manually depressing buttons 3504 to release catches (not shown) from within the hub 3306.

The decoupling structure 3500 may also include a swivel 3502 that allows for rotatable connection to an air circuit 4170.

The rotatability of the decoupling structure 3500, the decoupling structure 3500 being in the form of an elbow, and the rotatability of the swivel 3502 on the decoupling structure 3500 may all increased the degrees of freedom, which in turn reduce tube drag and torque on the patient interface 3000 caused by the connection to the air circuit 4170.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10 $cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components

5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.6.2.5.1 Pressure Transducer

One or more pressure transducers 5212 may be provided to the humidifier 5000 in addition to, or instead of, a pressure sensor 4272 provided in the RPT device 4000.

5.6.2.5.2 Flow Rate Transducer

One or more flow rate transducers 5214 may be provided to the humidifier 5000 in addition to, or instead of, a flow rate sensor 4274 provided in the RPT device 4000.

5.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.6.2.7 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.7 Breathing Waveform

FIG. 6 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
- (i) a 30% reduction in patient breathing for at least 10 seconds plus an associated 4% desaturation; or
- (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.8.4 Anatomy 5.8.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

*Glabella*: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.8.4.2 Anatomy of the Skull Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.8.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.9 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 5.10 REFERENCE SIGNS LIST | |
|---|---|
| Patient | 1000 |
| naris outline | 1001 |
| nose base outline | 1002 |
| bed partner | 1100 |
| patient interface | 3000 |
| seal - forming structure | 3100 |
| naris opening | 3102 |
| bridge portion | 3104 |
| plenum chamber connection opening | 3106 |
| lateral support region | 3108 |
| anterior region | 3109 |
| mid-lateral region | 3110 |
| nose base region | 3112 |
| medial region | 3114 |
| corner region | 3115 |
| lip superior region | 3116 |
| pronasale region | 3117 |
| flexible region | 3150 |
| plenum chamber | 3200 |
| internal opening | 3201 |
| plenum chamber lateral end | 3202 |
| plenum chamber connector | 3204 |
| notch | 3206 |
| chamfered edge | 3208 |
| slot | 3209 |
| chord | 3210 |
| superior point | 3220 |
| inferior point | 3230 |
| vent insert opening | 3240 |
| vent insert | 3242 |
| plenum chamber portion | 3260 |
| positioning and stabilising structure | 3300 |
| lateral portion | 3302 |
| superior portion | 3304 |
| hub | 3306 |
| tab | 3308 |
| posterior strap | 3310 |
| posterior strap end portion | 3311 |
| sleeve | 3312 |
| end | 3314 |
| receiver | 3316 |
| clip overmold | 3318 |
| clip | 3320 |
| clip projection | 3322 |
| lip | 3324 |
| plenum chamber vent | 3400 |
| decoupling structure vent | 3402 |
| decoupling structure | 3500 |
| swivel connector | 3502 |
| button | 3504 |
| connection port | 3600 |
| forehead support | 3700 |
| RPT device | 4000 |
| external housing | 4010 |

5.10 REFERENCE SIGNS LIST

| | |
|---|---|
| upper portion | 4012 |
| lower portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| heated air circuit | 4171 |
| supplemental oxygen | 4180 |
| electrical components | 4200 |
| Printed Circuit Board Assembly (PCBA) | 4202 |
| power supply | 4210 |
| input device | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithms | 4300 |
| therapy control module | 4330 |
| humidifier | 5000 |
| humidifier inlet | 5002 |
| humidifier outlet | 5004 |
| humidifier base | 5006 |
| reservoir | 5110 |
| conductive portion | 5120 |
| humidifier reservoir dock | 5130 |
| locking lever | 5135 |
| water level indicator | 5150 |
| humidifier transducer | 5210 |
| pressure transducer | 5212 |
| flow rate transducer | 5214 |
| temperature transducer | 5216 |
| humidity sensor | 5218 |
| heating element | 5240 |
| humidifier controller | 5250 |
| central humidifier controller | 5251 |
| heating element controller | 5252 |
| air circuit controller | 5254 |

The invention claimed is:

1. A patient interface comprising:
a plenum chamber pressurisable to a therapeutic pressure of at least 6 cmH$_2$O above ambient air pressure, said plenum chamber including a first plenum chamber inlet port sized and structured to receive a flow of air at the therapeutic pressure for breathing by a patient;
a seal-forming structure constructed and arranged to seal with a region of the patient's face surrounding an entrance to the patient's airways, said seal-forming structure having two naris openings separated by a bridge portion and configured such that the flow of air at said therapeutic pressure is delivered to the patient's nares through the naris openings, and the seal-forming structure being constructed and arranged to maintain said therapeutic pressure in the plenum chamber throughout the patient's respiratory cycle in use;
a positioning and stabilising structure configured to hold the seal-forming structure in a therapeutically effective position on the patient's head, the positioning and stabilising structure comprising a tie, and the tie being constructed and arranged so that at least a portion overlies a region of the patient's head superior to an otobasion superior of the patient's head in use; and
a vent structure comprising a plurality of vent holes formed in the plenum chamber and configured to allow a continuous flow of gases exhaled by the patient from an interior of the plenum chamber to ambient, said vent structure being sized and shaped to maintain the therapeutic pressure in the plenum chamber in use;
wherein the patient interface is configured to leave the patient's mouth uncovered during therapy,
wherein the seal-forming structure is shaped and dimensioned such that no portion of the seal-forming structure enters into the patient's nares during use,
wherein the seal-forming structure is shaped and dimensioned so as not to engage the patient's nose superior to the pronasale,
wherein the seal-forming structure comprises:
a medial region having a first thickness, the naris openings passing through the seal-forming structure at the medial region,
two mid-lateral regions, each of the mid-lateral regions having a second thickness, and each of the mid-lateral regions being positioned laterally outward from and adjacent to a corresponding lateral side of the medial region across a first boundary, and
two lateral support regions, each of the lateral support regions having a third thickness, each of the lateral support regions being positioned laterally outward from and adjacent to a corresponding one of the mid-lateral regions across a second boundary, and each of the lateral support regions being positioned laterally outward from and adjacent to a corresponding lateral side of the medial region across a third boundary,
wherein the mid-lateral regions are thicker than the medial region and thinner than the lateral support regions.

2. The patient interface of claim 1, wherein the seal-forming structure further comprises two corner regions, each of the corner regions being configured to engage the patient's face at a corresponding subalare region, and
wherein the first boundary, the second boundary, and the third boundary on each lateral side of the seal-forming structure converge at a point located in a corresponding one of the corner regions.

3. The patient interface of claim 1, wherein the bridge portion is slack in an undeformed state.

4. The patient interface of claim 3, wherein the bridge portion is thicker than the medial region.

5. The patient interface of claim 4, wherein each of the naris openings is surrounded by the medial region and the bridge portion.

6. The patient interface of claim 1, wherein the seal-forming structure is constructed of a flexible material.

7. The patient interface of claim 6, wherein the flexible material is silicone.

8. The patient interface of claim 1, wherein the plenum chamber comprises an inside surface and an outside surface, and wherein the inside surface is arranged to be at said therapeutic pressure in use, and the outside surface is arranged to be at ambient pressure in use.

9. The patient interface of claim 1, wherein the plenum chamber is structured to be rigid when subject to an internal pressure of less than about 30cmH2O above ambient pressure.

10. The patient interface of claim 1, wherein the plenum chamber is constructed from a hard plastic material.

11. The patient interface of claim 1, wherein the plenum chamber is constructed from a transparent material.

12. The patient interface of claim 1, wherein the medial region extends to an anterior side of the seal-forming structure that does not contact the patient during use.

13. The patient interface of claim 12, wherein the medial region extends to the anterior side of the seal-forming structure on a superior portion of the seal-forming structure.

14. The patient interface of claim 12, wherein the medial region extends to the anterior side of the seal-forming structure on an inferior portion of the seal-forming structure.

15. The patient interface of claim 1, wherein the mid-lateral regions extend to an anterior side of the seal-forming structure that does not contact the patient during use.

16. The patient interface of claim 15, wherein the mid-lateral regions extend to the anterior side of the seal-forming structure on a superior portion of the seal-forming structure.

17. The patient interface of claim 15, wherein the mid-lateral regions extend to the anterior side of the seal-forming structure on an inferior portion of the seal-forming structure.

18. The patient interface of claim 1, wherein the bridge portion is curved towards the plenum chamber to avoid contact with the patient's columella during use.

19. The patient interface of claim 1, wherein the medial region is positioned between the mid-lateral regions such that the mid-lateral regions are separate from one another.

20. The patient interface of claim 1, wherein the medial region and the mid-lateral regions are positioned between the lateral support regions such that the lateral support regions are separate from one another.

21. The patient interface of claim 1, wherein the mid-lateral regions are configured to avoid the patient's lip superior, cheeks, pronasale, and/or subnasale in use.

22. The patient interface of claim 1, wherein the the plenum chamber and the seal-forming structure are formed from a single homogeneous piece of material.

23. The patient interface of claim 22, wherein the single homogeneous piece of material is silicone.

24. The patient interface of claim 1, wherein the plenum chamber comprises a second plenum chamber inlet port, the first plenum chamber inlet port and the second plenum chamber inlet port being positioned on corresponding lateral sides of the plenum chamber, and
wherein the positioning and stabilising structure comprises a pair of conduits, each of the conduits being configured to be positioned on a corresponding lateral side of the patient's head in use, each of the conduits having a first end removably connected to a corresponding one of the first plenum chamber inlet port and the second plenum chamber inlet port to direct the flow of air at the therapeutic pressure into the plenum chamber.

25. The patient interface of claim 24, wherein the tie is connected to each of the conduits.

26. The patient interface of claim 24, wherein the positioning and stabilising structure comprises a hub, each of the conduits having a second end connected to the hub, and
wherein a decoupling structure having additional vent holes is rotatably connected to the hub and is configured to be connected to an air delivery circuit to receive the flow of air at the therapeutic pressure.

27. The patient interface of claim 1, wherein the first thickness of the medial region is constant across the entirety of the medial region,
wherein the second thickness of each of the mid-lateral regions is constant across the entirety of each of the mid-lateral regions, and
wherein the third thickness each of the lateral support regions is constant across the entirety of each of the lateral support regions.

28. The patient interface of claim 1, wherein the medial region further comprises a lip superior region that is at least partially bounded by each third boundary and configured to contact the patient's lip superior in use, and
wherein the shortest distance between each third boundary across the lip superior region is equal to or less than the shortest distance between each second boundary across the lip superior region.

29. The patient interface of claim 1, wherein the medial region further comprises a lip superior region that is at least partially bounded by each third boundary and configured to contact the patient's lip superior in use, and
wherein a lateral distance between each third boundary across the lip superior region is equal to or less than a lateral distance between each second boundary across the lip superior region.

30. The patient interface of claim 1, wherein the first thickness of the medial region at each first boundary is discrete from the second thickness of each of the mid-lateral regions at the corresponding first boundary,
wherein the second thickness of each of the mid-lateral regions at the corresponding second boundary is discrete from the third thickness of each of the lateral support regions at the corresponding second boundary, and
wherein the first thickness of the medial region at each third boundary is discrete from the third thickness of each of the lateral support regions at the corresponding third boundary.

* * * * *